(12) United States Patent
Talbert et al.

(10) Patent No.: US 11,624,830 B2
(45) Date of Patent: Apr. 11, 2023

(54) WIDE DYNAMIC RANGE USING A MONOCHROME IMAGE SENSOR FOR LASER MAPPING IMAGING

(71) Applicant: Cilag GmbH International, Zug (CH)

(72) Inventors: Joshua D. Talbert, Salt Lake City, UT (US); Donald M. Wichern, Ogden, UT (US)

(73) Assignee: Cilag GmbH International

( * ) Notice: Subject to any disclaimer, the term of this patent is extended or adjusted under 35 U.S.C. 154(b) by 590 days.

(21) Appl. No.: 16/696,972

(22) Filed: Nov. 26, 2019

(65) Prior Publication Data

US 2020/0400823 A1 Dec. 24, 2020

Related U.S. Application Data

(60) Provisional application No. 62/864,207, filed on Jun. 20, 2019.

(51) Int. Cl.
*G01S 17/89* (2020.01)
*H04N 1/107* (2006.01)
(Continued)

(52) U.S. Cl.
CPC ........ *G01S 17/89* (2013.01); *A61B 1/000095* (2022.02); *H04N 1/107* (2013.01); *G01S 7/4804* (2013.01)

(58) Field of Classification Search
CPC ....... G01S 17/89; G01S 7/4804; H04N 1/107; H04N 5/2256; H04N 5/37457;
(Continued)

(56) References Cited

U.S. PATENT DOCUMENTS 3,844,047 A 10/1974 Carson
4,556,057 A 12/1985 Hiruma et al.
(Continued)

FOREIGN PATENT DOCUMENTS

CN 111526775 A 8/2020
CN 111565620 A 8/2020
(Continued)

OTHER PUBLICATIONS

English Translation of CN111526775A prepared by Google Patents (https://patents.google.com/patent/CN111526775A/en?oq=CN111526775).
(Continued)

*Primary Examiner* — Jonathan M Hansen
(74) *Attorney, Agent, or Firm* — Terrence J. Edwards; TechLaw Ventures, PLLC

(57) ABSTRACT

Systems, methods, and devices for laser mapping and color imaging with increased dynamic range are disclosed. A system includes an emitter for emitting pulses of electromagnetic radiation and an image sensor comprising a pixel array for sensing reflected electromagnetic radiation, wherein the pixel array comprises a plurality of pixels each configurable as a short exposure pixel or a long exposure pixel. The system includes a controller comprising a processor in electrical communication with the image sensor and the emitter. The system is such that at least a portion of the pulses of electromagnetic radiation emitted by the emitter comprises a laser mapping pattern.

30 Claims, 39 Drawing Sheets

(51) Int. Cl.
*A61B 1/00* (2006.01)
*G01S 7/48* (2006.01)

(58) Field of Classification Search
CPC ....... H04N 2005/2255; H04N 5/35554; H04N 9/04521; A61B 1/000095; A61B 1/00165; A61B 1/045; A61B 1/05; A61B 1/0638; A61B 1/043; G01B 11/2513
See application file for complete search history.

(56) References Cited

U.S. PATENT DOCUMENTS

| | | | |
|---|---|---|---|
| 5,318,024 A | 6/1994 | Kittrell et al. |
| 5,363,387 A | 11/1994 | Sinofsky |
| 5,515,449 A | 5/1996 | Tsuruoka et al. |
| 5,749,830 A | 5/1998 | Kaneko et al. |
| 5,784,162 A | 7/1998 | Cabib et al. |
| 6,061,591 A | 5/2000 | Freitag et al. |
| 6,110,106 A | 8/2000 | MacKinnon et al. |
| 6,236,879 B1 | 5/2001 | Konings |
| 6,300,638 B1 | 10/2001 | Groger et al. |
| 6,537,211 B1 | 5/2003 | Wang et al. |
| 6,975,898 B2 | 12/2005 | Seibel |
| 9,509,917 B2 | 11/2016 | Blanquart et al. |
| 11,006,093 B1 | 5/2021 | Hegyi |
| 11,294,062 B2 * | 4/2022 | Talbert .................. G01S 7/4815 |
| 2001/0000317 A1 | 4/2001 | Yoneya et al. |
| 2002/0016533 A1 | 2/2002 | Marchitto et al. |
| 2002/0065468 A1 | 5/2002 | Utzinger et al. |
| 2002/0123666 A1 | 9/2002 | Matsumoto |
| 2002/0138008 A1 | 9/2002 | Tsujita et al. |
| 2002/0139920 A1 | 10/2002 | Seibel et al. |
| 2002/0161282 A1 | 10/2002 | Fulghum |
| 2003/0058440 A1 | 3/2003 | Scott et al. |
| 2003/0059108 A1 | 3/2003 | Hubel |
| 2003/0100824 A1 | 5/2003 | Warren et al. |
| 2003/0153825 A1 | 8/2003 | Mooradian et al. |
| 2003/0223248 A1 | 12/2003 | Cronin et al. |
| 2004/0010192 A1 | 1/2004 | Benaron et al. |
| 2004/0076319 A1 | 4/2004 | Fauver et al. |
| 2004/0116800 A1 | 6/2004 | Helfer et al. |
| 2004/0186351 A1 | 9/2004 | Imaizumi et al. |
| 2004/0234152 A1 | 11/2004 | Liege et al. |
| 2005/0020926 A1 | 1/2005 | Wilkof et al. |
| 2005/0107808 A1 | 5/2005 | Evans et al. |
| 2005/0165279 A1 | 7/2005 | Adler et al. |
| 2005/0205758 A1 | 9/2005 | Almeida |
| 2006/0052710 A1 | 3/2006 | Miura et al. |
| 2006/0069314 A1 | 3/2006 | Farr |
| 2006/0239723 A1 | 10/2006 | Okuda et al. |
| 2006/0276966 A1 | 12/2006 | Cotton et al. |
| 2007/0016077 A1 | 1/2007 | Nakaoka et al. |
| 2007/0046778 A1 | 3/2007 | Ishihara et al. |
| 2007/0057211 A1 | 3/2007 | Bahlman et al. |
| 2007/0081168 A1 | 4/2007 | Johnston |
| 2007/0086495 A1 | 4/2007 | Sprague et al. |
| 2007/0161854 A1 | 7/2007 | Alamaro et al. |
| 2007/0177009 A1 | 8/2007 | Bayer et al. |
| 2007/0242330 A1 | 10/2007 | Rosman et al. |
| 2007/0276234 A1 | 11/2007 | Shahidi |
| 2008/0058629 A1 | 3/2008 | Seibel et al. |
| 2008/0081950 A1 | 4/2008 | Koenig et al. |
| 2008/0090220 A1 | 4/2008 | Freeman et al. |
| 2008/0177139 A1 | 7/2008 | Courtney et al. |
| 2008/0177140 A1 | 7/2008 | Cline et al. |
| 2008/0192231 A1 | 8/2008 | Jureller et al. |
| 2009/0067458 A1 | 3/2009 | Ji et al. |
| 2009/0244260 A1 * | 10/2009 | Takahashi ............. A61B 5/0064 348/E13.001 |
| 2009/0289200 A1 | 11/2009 | Ishii |
| 2009/0306478 A1 | 12/2009 | Mizuyoshi |
| 2010/0049180 A1 | 2/2010 | Wells et al. |
| 2010/0056928 A1 | 3/2010 | Zuzak et al. |
| 2010/0128109 A1 | 5/2010 | Banks |
| 2010/0157039 A1 | 6/2010 | Sugai |
| 2010/0160917 A1 | 6/2010 | Fitz et al. |
| 2010/0168585 A1 | 7/2010 | Fuji et al. |
| 2010/0261958 A1 | 10/2010 | Webb et al. |
| 2010/0277087 A1 | 11/2010 | Ikeda |
| 2010/0297659 A1 | 11/2010 | Yoo |
| 2011/0087212 A1 | 4/2011 | Aldridge et al. |
| 2011/0169984 A1 | 7/2011 | Noguchi |
| 2011/0196355 A1 | 8/2011 | Mitchell et al. |
| 2011/0213252 A1 | 9/2011 | Fulghum |
| 2011/0280810 A1 | 11/2011 | Hauger et al. |
| 2012/0010465 A1 | 1/2012 | Erikawa et al. |
| 2012/0062722 A1 | 3/2012 | Sase |
| 2012/0123205 A1 | 5/2012 | Nie et al. |
| 2012/0265014 A1 | 10/2012 | Matsubara et al. |
| 2012/0273470 A1 | 11/2012 | Zediker et al. |
| 2012/0294498 A1 | 11/2012 | Popovic |
| 2013/0085484 A1 | 4/2013 | Van Valen et al. |
| 2013/0176395 A1 | 7/2013 | Kazakevich |
| 2013/0211246 A1 | 8/2013 | Parasher |
| 2013/0324797 A1 | 12/2013 | Igarashi et al. |
| 2014/0073885 A1 | 3/2014 | Frangioni |
| 2014/0111623 A1 | 4/2014 | Zhao et al. |
| 2014/0160259 A1 | 6/2014 | Blanquart et al. |
| 2014/0160260 A1 * | 6/2014 | Blanquart .............. H04N 5/369 348/68 |
| 2014/0163318 A1 | 6/2014 | Swanstrom |
| 2014/0163319 A1 * | 6/2014 | Blanquart .............. A61B 1/051 600/109 |
| 2014/0187967 A1 | 7/2014 | Wood et al. |
| 2014/0276093 A1 | 9/2014 | Zeien |
| 2014/0300718 A1 | 10/2014 | Krattiger et al. |
| 2014/0300750 A1 | 10/2014 | Nagamune |
| 2014/0336501 A1 | 11/2014 | Masumoto |
| 2015/0073209 A1 | 3/2015 | Ikeda |
| 2015/0223733 A1 | 8/2015 | Al-Alusi |
| 2015/0272694 A1 | 10/2015 | Charles |
| 2015/0305604 A1 | 10/2015 | Melsky |
| 2015/0309284 A1 | 10/2015 | Kagawa et al. |
| 2016/0006914 A1 | 1/2016 | Neumann |
| 2016/0042513 A1 | 2/2016 | Yudovsky |
| 2016/0062103 A1 | 3/2016 | Yang et al. |
| 2016/0183775 A1 | 6/2016 | Blanquart et al. |
| 2016/0195706 A1 | 7/2016 | Fujii |
| 2016/0335778 A1 | 11/2016 | Smits |
| 2017/0059305 A1 | 3/2017 | Nonn et al. |
| 2017/0078548 A1 | 3/2017 | Blanquart et al. |
| 2017/0086940 A1 | 3/2017 | Nakamura |
| 2017/0163971 A1 | 6/2017 | Wang et al. |
| 2017/0167980 A1 | 6/2017 | Dimitriadis et al. |
| 2017/0205198 A1 | 7/2017 | Roncone et al. |
| 2017/0209050 A1 | 7/2017 | Fengler et al. |
| 2017/0214841 A1 | 7/2017 | Blanquart et al. |
| 2017/0232269 A1 | 8/2017 | Luttrull et al. |
| 2017/0266323 A1 | 9/2017 | Tao et al. |
| 2017/0280029 A1 | 9/2017 | Steiner |
| 2017/0280970 A1 | 10/2017 | Sartor et al. |
| 2017/0339327 A1 * | 11/2017 | Koshkin ............ H04N 9/04557 |
| 2017/0347043 A1 | 11/2017 | Rephaeli et al. |
| 2017/0360275 A1 | 12/2017 | Yoshizaki |
| 2018/0000401 A1 | 1/2018 | Kang et al. |
| 2018/0008138 A1 | 1/2018 | Thommen et al. |
| 2018/0014000 A1 | 1/2018 | Blanquart et al. |
| 2018/0020920 A1 | 1/2018 | Ermilov et al. |
| 2018/0038845 A1 | 2/2018 | Zimmermann et al. |
| 2018/0234603 A1 | 7/2018 | Moore et al. |
| 2018/0217262 A1 | 8/2018 | Albelo et al. |
| 2018/0220920 A1 | 8/2018 | Loh et al. |
| 2018/0246313 A1 | 8/2018 | Eshel et al. |
| 2018/0310828 A1 | 11/2018 | DiMaio et al. |
| 2019/0124247 A1 | 4/2019 | Behrooz et al. |
| 2019/0129037 A1 | 5/2019 | Fujita et al. |
| 2019/0149713 A1 | 5/2019 | Blanquart et al. |
| 2019/0191974 A1 | 6/2019 | Talbert et al. |
| 2019/0191975 A1 | 6/2019 | Talbert et al. |
| 2019/0191976 A1 | 6/2019 | Talbert et al. |
| 2019/0191977 A1 | 6/2019 | Talbert et al. |
| 2019/0191978 A1 | 6/2019 | Talbert et al. |
| 2019/0197712 A1 | 6/2019 | Talbert et al. |
| 2019/0200848 A1 | 7/2019 | McDowall et al. |

(56) References Cited

U.S. PATENT DOCUMENTS

| | | |
|---|---|---|
| 2019/0204577 A1 | 7/2019 | Faris et al. |
| 2020/0315439 A1 | 10/2020 | Mizoguchi et al. |
| 2020/0367818 A1 | 11/2020 | DaCosta et al. |
| 2020/0400498 A1 | 12/2020 | Talbert et al. |
| 2020/0400824 A1 | 12/2020 | Talbert et al. |
| 2020/0400936 A1 | 12/2020 | Talbert et al. |
| 2020/0404151 A1 | 12/2020 | Talbert et al. |
| 2020/0404152 A1 | 12/2020 | Talbert et al. |
| 2022/0236421 A1 | 7/2022 | Talbert et al. |

FOREIGN PATENT DOCUMENTS

| | | |
|---|---|---|
| CN | 111601536 A | 8/2020 |
| JP | 2008259595 A | 10/2008 |
| WO | 2014018951 A1 | 1/2014 |
| WO | 2014134314 A1 | 9/2014 |
| WO | 2015077493 A1 | 5/2015 |
| WO | 2016049215 A2 | 3/2016 |
| WO | 2016203572 A1 | 12/2016 |
| WO | 2017201093 A1 | 11/2017 |
| WO | 2017223206 A1 | 12/2017 |
| WO | 2019133736 A1 | 7/2019 |
| WO | 2019133737 A1 | 7/2019 |
| WO | 2019133739 A1 | 7/2019 |
| WO | 2019133741 A1 | 7/2019 |
| WO | 2019133750 A1 | 7/2019 |
| WO | 2019133753 A1 | 7/2019 |
| WO | 2020256935 A1 | 12/2020 |
| WO | 2020256936 A1 | 12/2020 |
| WO | 2020256937 A1 | 12/2020 |
| WO | 2020256939 A1 | 12/2020 |
| WO | 2020256940 A1 | 12/2020 |

OTHER PUBLICATIONS

English Translation of CN111565620A Prepared by Google Patents (https://patents.google.com/patent/CN111565620A/en?oq=CN111565620).

English Translation of CN111601536A Prepared by Google Patents (https://patents.google.com/patent/CN111601536A/en?oq=CN111601536A).

Google Patents Translation of JP2008259595A (https://patents google.com/patent/JP2008259595A/en?oq=JP+2008259595).

Google Patents Translation of WO2016203572 (https://patents.google.com/patent/JPWO2016203572A1/en?oq=WO2016203572).

* cited by examiner

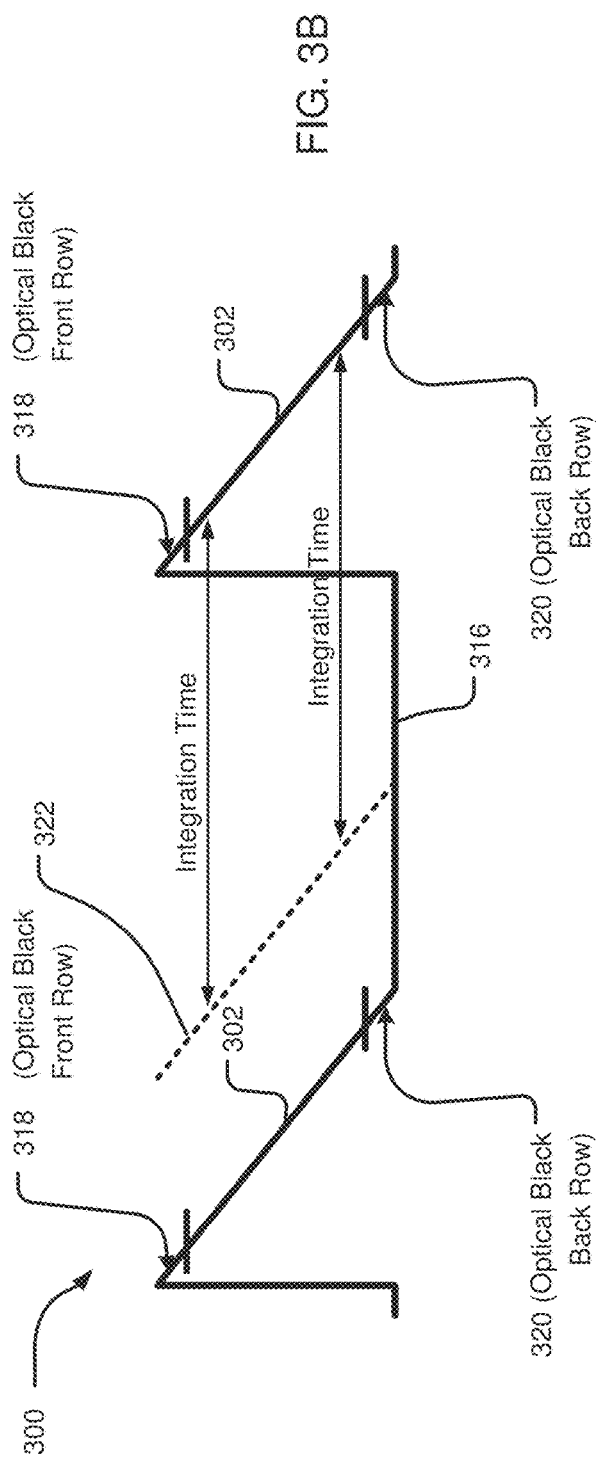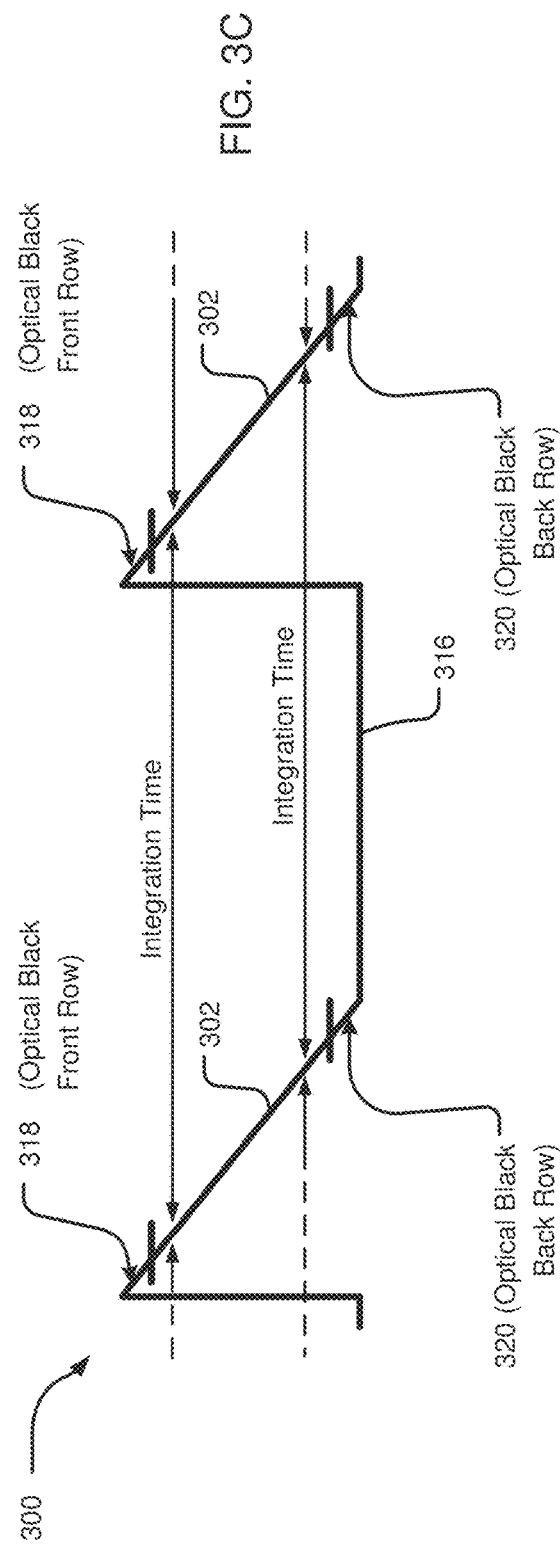

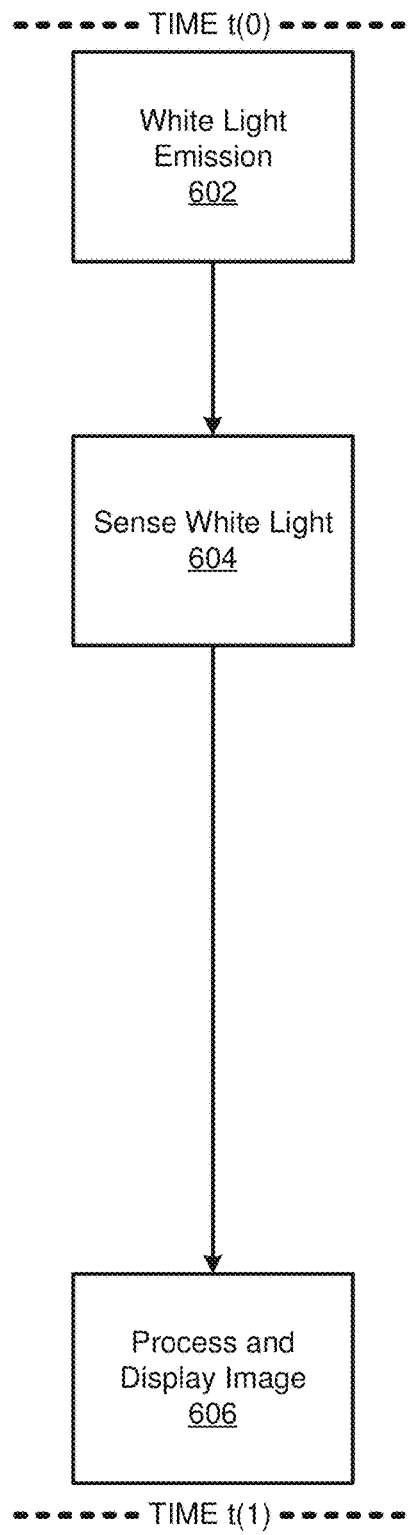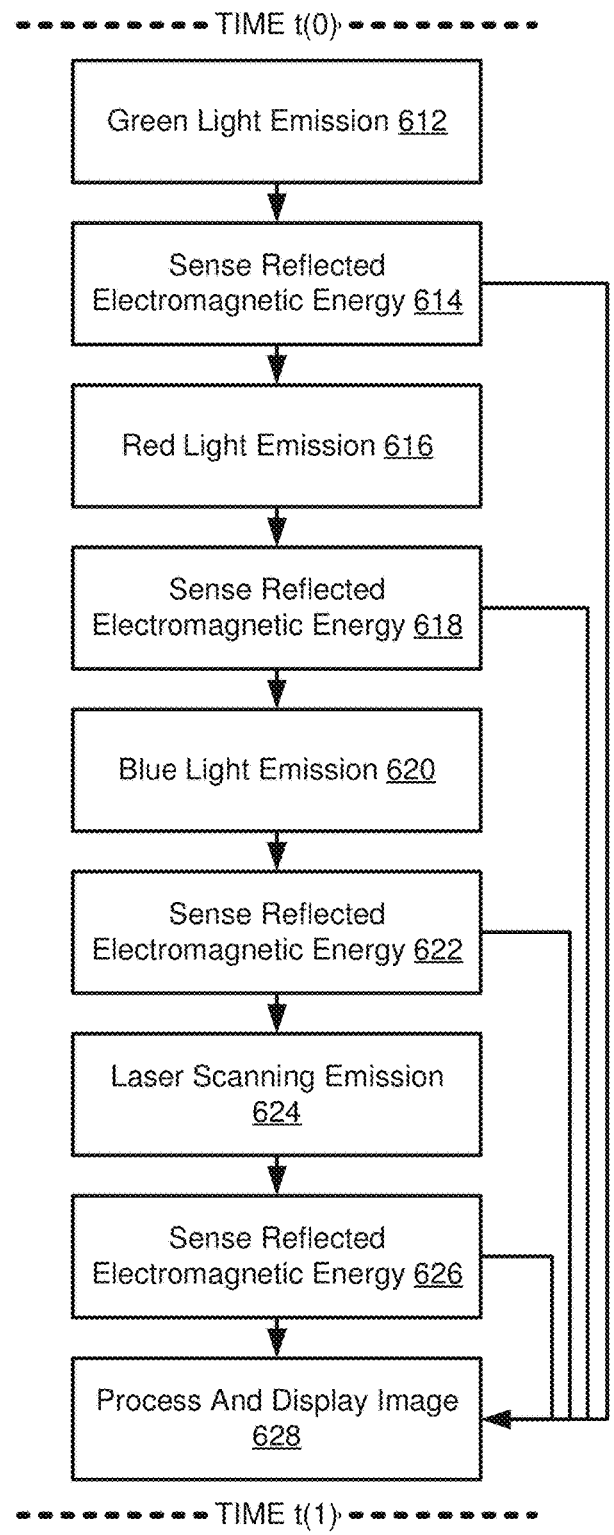
FIG. 6A
(Prior Art)
FIG. 6B

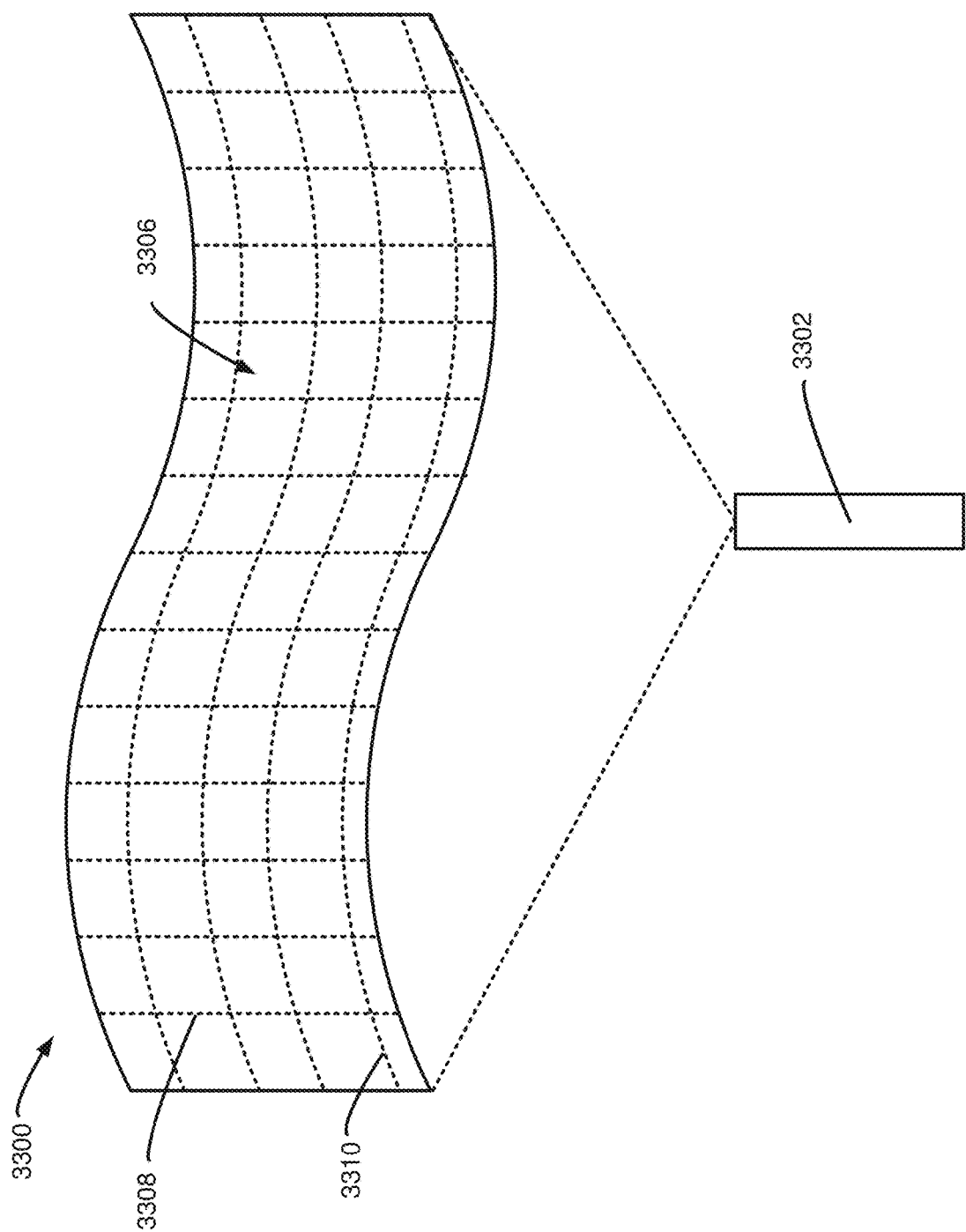

3D with double pixel array

WIDE DYNAMIC RANGE USING A MONOCHROME IMAGE SENSOR FOR LASER MAPPING IMAGING

CROSS-REFERENCE TO RELATED APPLICATIONS

This application claims the benefit of U.S. Provisional Patent Application No. 62/864,207, filed Jun. 20, 2019, titled "WIDE DYNAMIC RANGE USING A MONOCHROME IMAGE SENSOR FOR HYPERSPECTRAL AND FLUORESCENCE IMAGING," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

This application is directed to digital imaging and is particularly directed to laser mapping imaging in a light deficient environment.

BACKGROUND

Advances in technology have provided advances in imaging capabilities for medical use. An endoscope may be used to look inside a body and examine the interior of an organ or cavity of the body. Endoscopes are used for investigating a patient's symptoms, confirming a diagnosis, or providing medical treatment. A medical endoscope may be used for viewing a variety of body systems and parts such as the gastrointestinal tract, the respiratory tract, the urinary tract, the abdominal cavity, and so forth. Endoscopes may further be used for surgical procedures such as plastic surgery procedures, procedures performed on joints or bones, procedures performed on the neurological system, procedures performed within the abdominal cavity, and so forth.

In some instances of endoscopic imaging, it may be beneficial or necessary to view a space in color. A digital color image includes at least three layers, or "color channels," that cumulatively form an image with a range of hues. Each of the color channels measures the intensity and chrominance of light for a spectral band. Commonly, a digital color image includes a color channel for red, green, and blue spectral bands of light (this may be referred to as a Red Green Blue or RGB image). Each of the red, green, and blue color channels include brightness information for the red, green, or blue spectral band of light. The brightness information for the separate red, green, and blue layers are combined to create the color image. Because a color image is made up of separate layers, a conventional digital camera image sensor includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image. The at least three distinct types of pixel sensors consume significant physical space such that the complete pixel array cannot fit in the small distal end of an endoscope.

Because a traditional image sensor cannot fit in the distal end of an endoscope, the image sensor is traditionally located in a handpiece unit of an endoscope that is held by an endoscope operator and is not placed within the body cavity. In such an endoscope, light is transmitted along the length of the endoscope from the handpiece unit to the distal end of the endoscope. This configuration has significant limitations. Endoscopes with this configuration are delicate and can be easily misaligned or damaged when bumped or impacted during regular use. This can significantly degrade the quality of the images and necessitate that the endoscope be frequently repaired or replaced.

The traditional endoscope with the image sensor placed in the handpiece unit is further limited to capturing only color images. However, in some implementations, it may be desirable to capture images with laser mapping image data in addition to color image data. Laser mapping imaging can capture the surface shape of objects and landscapes and measure distances between objects within a scene. In some implementations, it may be desirable to measure distances and surface shapes within a body cavity during an endoscopic imaging procedure.

However, applications of laser mapping technology known in the art typically require highly specialized equipment that may not be useful for multiple applications. Further, laser mapping technology provides a limited view of an environment and typically must be used in conjunction with multiple separate systems. In the context of endoscopic medical imaging procedures, all sensors must fit within a small physical area within a body cavity. In some instances, the geographic area is exceptionally small and may only accommodate a very small tip of an endoscope. As such, medical endoscopes known in the art are necessarily small and cannot accommodate multiple distinct imaging and ranging systems. It is therefore desirable to develop an endoscopic imaging system that is capable of generating laser mapping data in a small space such as a body cavity.

In light of the foregoing, described herein are systems, methods, and devices for laser mapping imaging in a light deficient environment. Such systems, methods, and devices may provide multiple datasets for identifying critical structures in a body and providing precise and valuable information about a body cavity.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIGS. 3A to 3D are illustrations of the operational cycles of a sensor used to construct an exposure frame;

FIG. 6A is a schematic diagram of a process for recording a video with full spectrum light over a period of time from t(0) to t(1);

FIG. 6B is a schematic diagram of a process for recording a video by pulsing portioned spectrum light over a period of time from t(0) to t(1);

FIG. 33 illustrates an example laser mapping pattern that may be pulsed by an imaging system;

DETAILED DESCRIPTION

Figure 1:
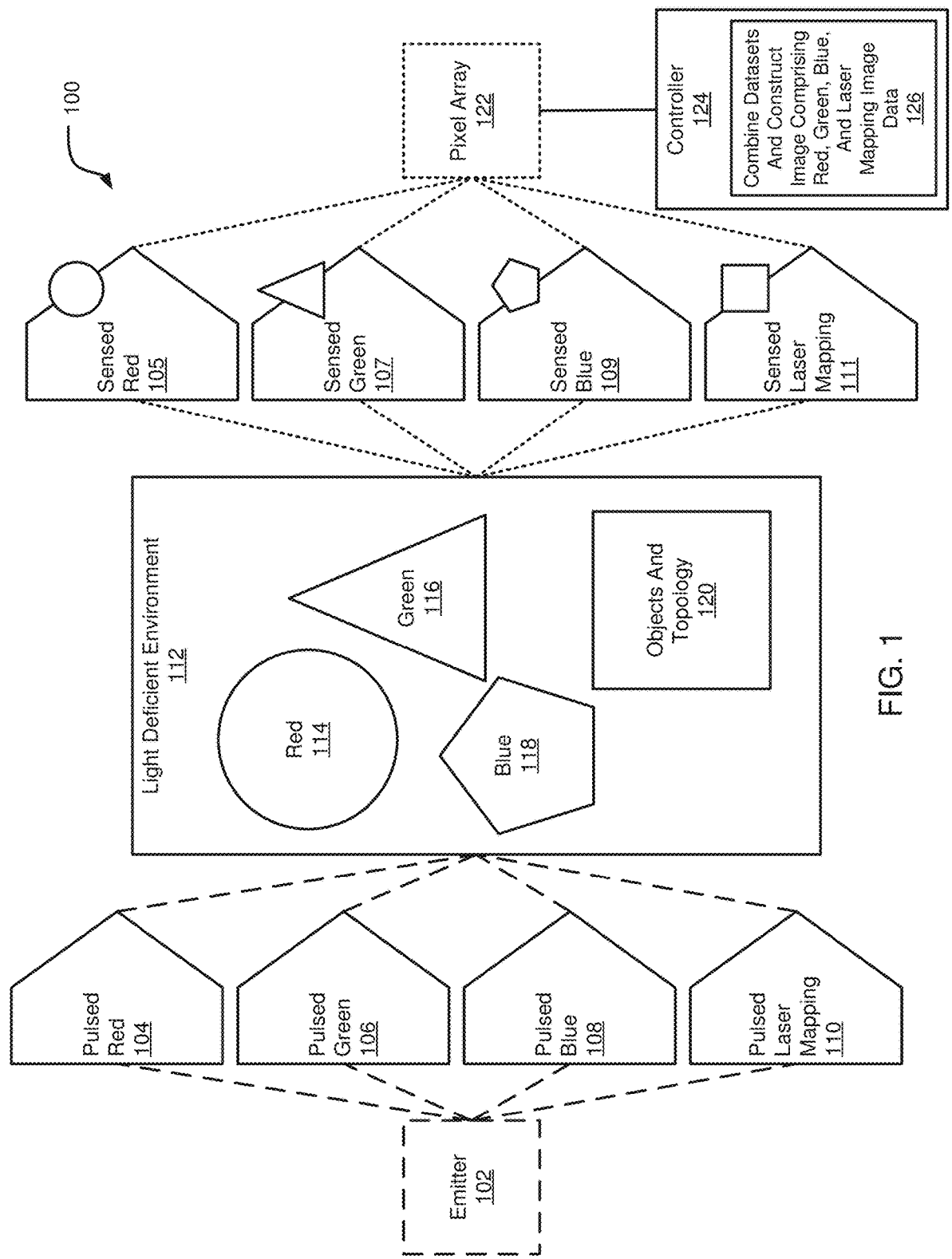
FIG. 1 is a schematic view of a system for digital imaging in a light deficient environment with a paired emitter and pixel array.

Disclosed herein are systems, methods, and devices for digital imaging that may be primarily suited to medical applications such as medical endoscopic imaging. An embodiment of the disclosure is an endoscopic system for laser mapping and/or color imaging in a light deficient environment.

The imaging systems disclosed herein place aggressive constraints on the size of the image sensor. This enables the image sensor to be placed in a distal end of an endoscope and thereby enables the corresponding benefits of improved optical simplicity and increased mechanical robustness for the endoscope. However, placing these aggressive constraints on the image sensor area results in fewer and/or smaller pixels and can degrade image quality. An embodiment of the disclosure overcomes this challenge by incorporating a monochrome image sensor with minimal peripheral circuitry, connection pads, and logic. The imaging systems disclosed herein provide means for extending the dynamic range, sensor sensitivity, and spatial resolution of resultant images while still decreasing the overall size of the image sensor.

In an embodiment, a system includes an image sensor comprising a pixel array. The dynamic range and spatial resolution of the image sensor are improved by segmenting the pixels of the pixel array in a checkerboard pattern. The pixel array has only monochrome pixels that are "color agnostic" and can sense reflected electromagnetic radiation with a wide range of wavelengths. The checkerboard pattern of the pixels may be configured to include long exposure pixel and short exposure pixels arranged in a checkerboard pattern with respect to one another. The pixel array may then return two exposure frames for each reading of the pixel array, including a short exposure frame and a long exposure frame. The short exposure frame and the long exposure frame may be combined to generate a combined exposure frame with increased dynamic range. The checkerboard pattern of the pixels enables granular spatial segmentation for generating multiple exposure frames for each reading of the pixel array.

Conventional endoscopes are designed such that the image sensor is placed at a proximal end of the device within a handpiece unit. This configuration requires that incident light travel the length of the endoscope by way of precisely coupled optical elements. The precise optical elements can easily be misaligned during regular use, and this can lead to image distortion or image loss. Embodiments of the disclosure place an image sensor within a distal end of the endoscope itself. This provides greater optical simplicity when compared with implementations known in the art. However, an acceptable solution to this approach is by no means trivial and introduces its own set of engineering challenges, not least of which that the image sensor must fit within a highly constrained area. Disclosed herein are systems, methods, and devices for digital imaging in a light deficient environment that employ minimal area image sensors and can be configured for laser mapping and color imaging.

In some instances, it is desirable to generate endoscopic imaging with multiple data types or multiple images overlaid on one another. For example, it may be desirable to generate a color ("RGB") image that further includes laser mapping imaging data overlaid on the RGB image. An overlaid image of this nature may enable a medical practitioner or computer program to identify highly accurate dimensions and three-dimensional topologies of critical body structures and further identify distances between tools and other structures within the light deficient environment based on the laser mapping data. Historically, this would require the use of multiple sensor systems including an image sensor for color imaging and one or more additional image sensors for laser mapping imaging. In such systems, the multiple image sensors would have multiple types of pixel sensors that are each sensitive to distinct ranges of electromagnetic radiation. In systems known in the art, this includes the three separate types of pixel sensors for generating an RGB color image along with additional sensors and systems for generating the laser mapping data. These multiple different sensors consume a prohibitively large physical space and cannot be located at a distal tip of the endoscope. In systems known in the art, the camera or cameras are not placed at the distal tip of the endoscope and are instead placed in an endoscope handpiece or robotic unit.

This introduces numerous disadvantages and causes the endoscope to be very delicate. The delicate endoscope may be damaged and image quality may be degraded when the endoscope is bumped or impacted during use. Considering the foregoing, disclosed herein are systems, methods, and devices for endoscopic imaging in a light deficient environment. The systems, methods, and devices disclosed herein provide means for employing multiple imaging techniques in a single imaging session while permitting one or more image sensors to be disposed in a distal tip of the endoscope.

Laser Mapping Imaging

In an embodiment, the systems, methods, and devices disclosed herein provide means for generating laser mapping data with an endoscopic imaging system. Laser mapping data can be used to determine precise measurements and topographical outlines of a scene. In one implementation, laser mapping data is used to determine precise measurements between, for example, structures or organs in a body cavity, devices or tools in the body cavity, and/or critical structures in the body cavity. As discussed herein, the term "laser mapping" may encompass technologies referred to as laser mapping, laser scanning, topographical scanning, three-dimensional scanning, laser tracking, tool tracking, and others.

Laser mapping generally includes the controlled deflection of laser beams. Within the field of three-dimensional object scanning, laser mapping combines controlled steering of laser beams with a laser rangefinder. By taking a distance measurement at every direction, the laser rangefinder can rapidly capture the surface shape of objects, tools, and landscapes. Construction of a full three-dimensional topology may include combining multiple surface models that are obtained from different viewing angles. Various measurement systems and methods exist in the art for applications in archaeology, geography, atmospheric physics, autonomous vehicles, and others. One such system includes light detection and ranging (LIDAR), which is a three-dimensional laser mapping system. LIDAR has been applied in navigation systems such as airplanes or satellites to determine position and orientation of a sensor in combination with other systems and sensors. LIDAR uses active sensors to illuminate an object and detect energy that is reflected off the object and back to a sensor.

As discussed herein, the term "laser mapping" includes laser tracking. Laser tracking, or the use of lasers for tool tracking, measures objects by determining the positions of optical targets held against those objects. Laser trackers can be accurate to the order of 0.025 mm over a distance of several meters. In an embodiment, an endoscopic imaging system pulses light for use in conjunction with a laser tracking system such that the position or tools within a scene can be tracked and measured. In such an embodiment, the endoscopic imaging system may pulse a laser tracking pattern on a tool, object, or other structure within a scene being imaged by the endoscopic imaging system. A target may be placed on the tool, object, or other structure within the scene. Measurements between the endoscopic imaging system and the target can be triggered and taken at selected points such that the position of the target (and the tool, object, or other structure to which the target is affixed) can be tracked by the endoscopic imaging system.

Pulsed Imaging

Some implementations of the disclosure include aspects of a combined sensor and system design that allows for high definition imaging with reduced pixel counts in a controlled illumination environment. This is accomplished with frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a hyperspectral or fluorescence image. The pixels may be color agnostic such that each pixel generates data for each pulse of electromagnetic radiation, including pulses for red, green, and blue visible light wavelengths along with other wavelengths used for hyperspectral imaging, fluorescence imaging, and laser mapping imaging.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

As used herein, monochromatic sensor refers to an unfiltered imaging sensor. Since the pixels are color agnostic, the effective spatial resolution is appreciably higher than for their color (typically Bayer-pattern filtered) counterparts in conventional single-sensor cameras. Monochromatic sensors may also have higher quantum efficiency because fewer incident photons are wasted between individual pixels.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert.

It should be noted that as used herein the term "light" is both a particle and a wavelength and is intended to denote electromagnetic radiation that is detectable by a pixel array and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

Referring now to the figures, FIG. 1 illustrates a schematic diagram of a system 100 for sequential pulsed imaging in a light deficient environment. The system 100 can be deployed to generate an RGB image with laser mapping data overlaid on the RGB image. The system 100 includes an emitter 102 and a pixel array 122. The emitter 102 pulses a partition of electromagnetic radiation in the light deficient environment 112 and the pixel array 122 senses instances of reflected electromagnetic radiation. The emitter 102 and the pixel array 122 work in sequence such that one or more pulses of a partition of electromagnetic radiation results in image data sensed by the pixel array 122.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

A pixel array 122 of an image sensor may be paired with the emitter 102 electronically, such that the emitter 102 and the pixel array 122 are synced during operation for both receiving the emissions and for the adjustments made within the system. The emitter 102 may be tuned to emit electromagnetic radiation in the form of a laser, which may be pulsed to illuminate a light deficient environment 112. The emitter 102 may pulse at an interval that corresponds to the operation and functionality of the pixel array 122. The emitter 102 may pulse light in a plurality of electromagnetic partitions such that the pixel array receives electromagnetic energy and produces a dataset that corresponds in time with each specific electromagnetic partition. For example, FIG. 1 illustrates an implementation wherein the emitter 102 emits four different partitions of electromagnetic radiation, including red 104, green 106, blue 108 wavelengths, and a laser mapping 110 pulsing scheme. The laser mapping 110 pulsing scheme may include a grid pattern for identifying a topology 120 of a scene in the light deficient environment 112 and further for measuring dimensions and distances within the scene. The laser mapping 110 pulsing scheme is any suitable pulsing scheme or pattern that may be used for generating laser mapping image data. The laser mapping imaging data includes data generated by technologies known as laser mapping, laser scanning, topographical scanning, three-dimensional scanning, laser tracking, tool tracking, and others.

The light deficient environment 112 includes structures, tissues, and other elements that reflect a combination of red 114, green 116, and/or blue 118 light. A structure that is perceived as being red 114 will reflect back pulsed red 104 light. The reflection off the red structure results in sensed red 105 by the pixel array 122 following the pulsed red 104 emission. The data sensed by the pixel array 122 results in a red exposure frame. A structure that is perceived as being green 116 will reflect back pulsed green 106 light. The reflection off the green structure results in sensed green 107 by the pixel array 122 following the pulsed green 106 emission. The data sensed by the pixel array 122 results in a green exposure frame. A structure that is perceived as being blue 118 will reflect back pulsed blue 108 light. The reflection off the blue structure results in sensed blue 109 by the pixel array 122 following the pulsed blue 108 emission. The data sensed by the pixel array 122 results in a blue exposure frame.

When a structure is a combination of colors, the structure will reflect back a combination of the pulsed red 104, pulsed green 106, and/or pulsed blue 108 emissions. For example, a structure that is perceived as being purple will reflect back light from the pulsed red 104 and pulsed blue 108 emissions. The resulting data sensed by the pixel array 122 will indicate that light was reflected in the same region following the pulsed red 104 and pulsed blue 108 emissions. When the resultant red exposure frame and blue exposure frames are combined to form the RGB image frame, the RGB image frame will indicate that the structure is purple.

In an embodiment where the light deficient environment 112 includes a fluorescent reagent or dye or includes one or more fluorescent structures, tissues, or other elements, the pulsing scheme may include the emission of a certain fluorescence excitation wavelength. The certain fluorescence excitation wavelength may be selected to fluoresce a known fluorescent reagent, dye, or other structure. The fluorescent structure will be sensitive to the fluorescence excitation wavelength and will emit a fluorescence relaxation wavelength. The fluorescence relaxation wavelength will be sensed by the pixel array 122 following the emission of the fluorescence excitation wavelength. The data sensed by the pixel array 122 results in a fluorescence exposure frame. The fluorescence exposure frame may be combined with multiple other exposure frames to form an image frame. The data in the fluorescence exposure frame may be overlaid on an RGB image frame that includes data from a red exposure frame, a green exposure frame, and a blue exposure frame.

In an embodiment where the light deficient environment 112 includes structures, tissues, or other materials that emit a spectral response to certain partitions of the electromagnetic spectrum, the pulsing scheme may further include the emission of a hyperspectral partition of electromagnetic radiation for the purpose of eliciting the spectral response from the structures, tissues, or other materials present in the light deficient environment 112. The spectral response includes the emission or reflection of certain wavelengths of electromagnetic radiation. The spectral response can be sensed by the pixel array 122 and result in a hyperspectral exposure frame. The hyperspectral exposure frame may be combined with multiple other exposure frames to form an image frame. The data in the hyperspectral exposure frame may be overlaid on an RGB image frame that includes data from a red exposure frame, a green exposure frame, and a blue exposure frame.

In an embodiment, the pulsing scheme includes the emission of a laser mapping 110 pattern. The reflected electromagnetic radiation sensed by the pixel array 122 following the emission of the laser mapping 110 pattern results in a laser mapping exposure frame that includes the sensed laser mapping 111 data. The data in the laser mapping exposure frame may be provided to a corresponding system to identify, for example, distances between tools present in the light deficient environment 112, a three-dimensional surface topology of a scene in the light deficient environment 112, distances, dimensions, or positions of structures or objects within the scene, distances dimensions, or positions of tools within the scene, and so forth. This data may be overlaid on an RGB image frame or otherwise provided to a user of the system.

The emitter 102 may be a laser emitter that is capable of emitting pulsed red 104 light for generating sensed red 105 data for identifying red 114 elements within the light deficient environment 112. The emitter 102 is further capable of emitting pulsed green 106 light for generating sensed green 107 data for identifying green 116 elements within the light deficient environment. The emitter 102 is further capable of emitting pulsed blue 108 light for generating sensed blue 109 data for identifying blue 118 elements within the light deficient environment. The emitter 102 is further capable of emitting a laser mapping 110 pulsing scheme for mapping the topology 120 of a scene within the light deficient environment 112. The emitter 102 is capable of emitting the pulsed red 104, pulsed green 106, pulsed blue 108, and pulsed laser mapping 110 pulsing schemes in any desired sequence.

The pixel array 122 senses reflected electromagnetic radiation. Each of the sensed red 105, the sensed green 107, the sensed blue 109, and the sensed laser mapping 111 data can be referred to as an "exposure frame." Each exposure frame is assigned a specific color or wavelength partition, wherein the assignment is based on the timing of the pulsed color or wavelength partition from the emitter 102. The exposure frame in combination with the assigned specific color or wavelength partition may be referred to as a dataset. Even though the pixels 122 are not color-dedicated, they can be assigned a color for any given dataset based on a priori information about the emitter.

For example, during operation, after pulsed red 104 light is pulsed in the light deficient environment 112, the pixel array 122 senses reflected electromagnetic radiation. The reflected electromagnetic radiation results in an exposure frame, and the exposure frame is catalogued as sensed red 105 data because it corresponds in time with the pulsed red 104 light. The exposure frame in combination with an indication that it corresponds in time with the pulsed red 104 light is the "dataset." This is repeated for each partition of electromagnetic radiation emitted by the emitter 102. The data created by the pixel array 122 includes the sensed red 105 exposure frame identifying red 114 components in the light deficient environment and corresponding in time with the pulsed red 104 light. The data further includes the sensed green 107 exposure frame identifying green 116 components in the light deficient environment and corresponding in time with the pulsed green 106 light. The data further includes the sensed blue 109 exposure frame identifying blue 118 components in the light deficient environment and corresponding in time with the pulsed blue 108 light. The data further includes the sensed laser mapping 111 exposure frame identifying the topology 120 and corresponding in time with the laser mapping 110 pulsing scheme.

In one embodiment, three datasets representing RED, GREEN and BLUE electromagnetic pulses are combined to form a single image frame. Thus, the information in a red exposure frame, a green exposure frame, and a blue exposure frame are combined to form a single RGB image frame. One or more additional datasets representing other wavelength partitions may be overlaid on the single RGB image frame. The one or more additional datasets may represent, for example, the laser mapping data, fluorescence imaging data, and/or hyperspectral imaging data.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infrared; any combination of the foregoing, or any other color combination, including all visible and non-visible wavelengths, without departing from the scope of the disclosure. In the figure, the light deficient environment 112 to be imaged includes red 114, green 116, and blue 118 portions, and further includes a topology 120 that can be sensed and mapped into a three-dimensional rendering. As illustrated in the figure, the reflected light from the electromagnetic pulses only contains the data for the portion of the object having the specific color that corresponds to the pulsed color partition. Those separate color (or color interval) datasets can then be used to reconstruct the image by combining the datasets at 126. The information in each of the multiple exposure frames (i.e., the multiple datasets) may be combined by a controller 124, a control unit, a camera control unit, the image sensor, an image signal processing pipeline, or some other computing resource that is configurable to process the multiple exposure frames and combine the datasets at 126. The datasets may be combined to generate the single image frame within the endoscope unit itself or offsite by some other processing resource.

Figure 2:
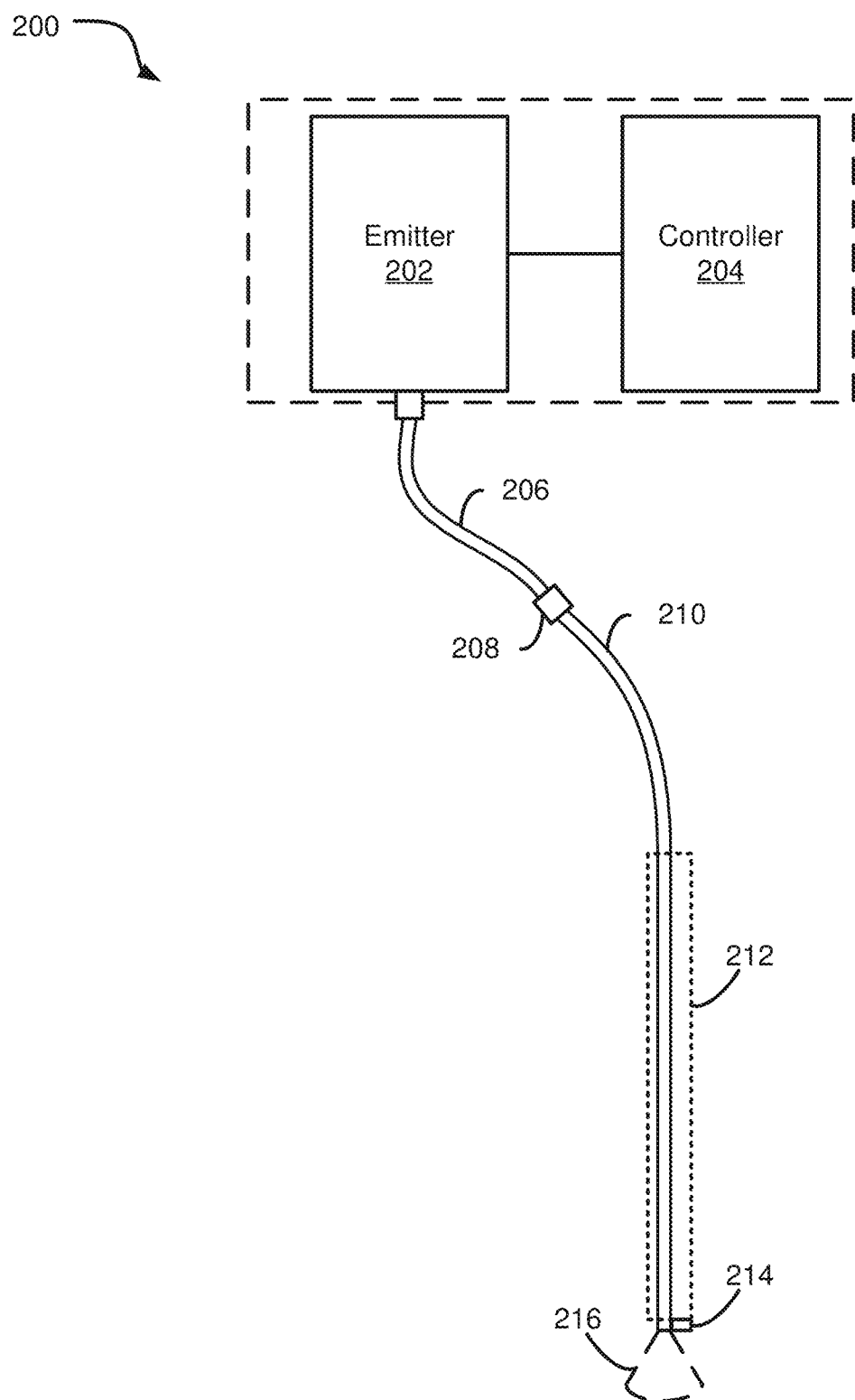
FIG. 2 is a system for providing illumination to a light deficient environment for endoscopic imaging.

FIG. 2 is a system 200 for providing illumination to a light deficient environment, such as for endoscopic imaging. The system 200 may be used in combination with any of the systems, methods, or devices disclosed herein. The system 200 includes an emitter 202, a controller 204, a jumper waveguide 206, a waveguide connector 208, a lumen waveguide 210, a lumen 212, and an image sensor 214 with accompanying optical components (such as a lens). The emitter 202 (may be generically referred to as a "light source") generates light that travels through the jumper waveguide 206 and the lumen waveguide 210 to illuminate a scene at a distal end of the lumen 212. The emitter 202 may be used to emit any wavelength of electromagnetic energy including visible wavelengths, infrared, ultraviolet, hyperspectral, fluorescence excitation, or other wavelengths. The lumen 212 may be inserted into a patient's body for imaging, such as during a procedure or examination. The light is output as illustrated by dashed lines 216. A scene illuminated by the light may be captured using the image sensor 214 and displayed for a doctor or some other medical personnel. The controller 204 may provide control signals to the emitter 202 to control when illumination is provided to a scene. In one embodiment, the emitter 202 and controller 204 are located within a camera control unit (CCU) or external console to which an endoscope is connected. If the image sensor 214 includes a CMOS sensor, light may be periodically provided to the scene in a series of illumination pulses between readout periods of the image sensor 214 during what is known as a blanking period. Thus, the light may be pulsed in a controlled manner to avoid overlapping into readout periods of the image pixels in a pixel array of the image sensor 214.

In one embodiment, the lumen waveguide 210 includes one or more optical fibers. The optical fibers may be made of a low-cost material, such as plastic to allow for disposal of the lumen waveguide 210 and/or other portions of an endoscope. In one embodiment, the lumen waveguide 210 is a single glass fiber having a diameter of 500 microns. The jumper waveguide 206 may be permanently attached to the emitter 202. For example, a jumper waveguide 206 may receive light from an emitter within the emitter 202 and provide that light to the lumen waveguide 210 at the location of the connector 208. In one embodiment, the jumper waveguide 106 includes one or more glass fibers. The jumper waveguide may include any other type of waveguide for guiding light to the lumen waveguide 210. The connector 208 may selectively couple the jumper waveguide 206 to the lumen waveguide 210 and allow light within the jumper waveguide 206 to pass to the lumen waveguide 210. In one embodiment, the lumen waveguide 210 is directly coupled to a light source without any intervening jumper waveguide 206.

The image sensor 214 includes a pixel array. In an embodiment, the image sensor 214 includes two or more pixel arrays for generating a three-dimensional image. The image sensor 214 may constitute two more image sensors that each have an independent pixel array and can operate independent of one another. The pixel array of the image sensor 214 includes active pixels and optical black ("OB") or optically blind pixels. The active pixels may be clear "color agnostic" pixels that are capable of sensing imaging data for any wavelength of electromagnetic radiation. The optical black pixels are read during a blanking period of the pixel array when the pixel array is "reset" or calibrated. In an embodiment, light is pulsed during the blanking period of the pixel array when the optical black pixels are being read. After the optical black pixels have been read, the active pixels are read during a readout period of the pixel array. The active pixels may be charged by the electromagnetic radiation that is pulsed during the blanking period such that the active pixels are ready to be read by the image sensor during the readout period of the pixel array.

Figure 2A:
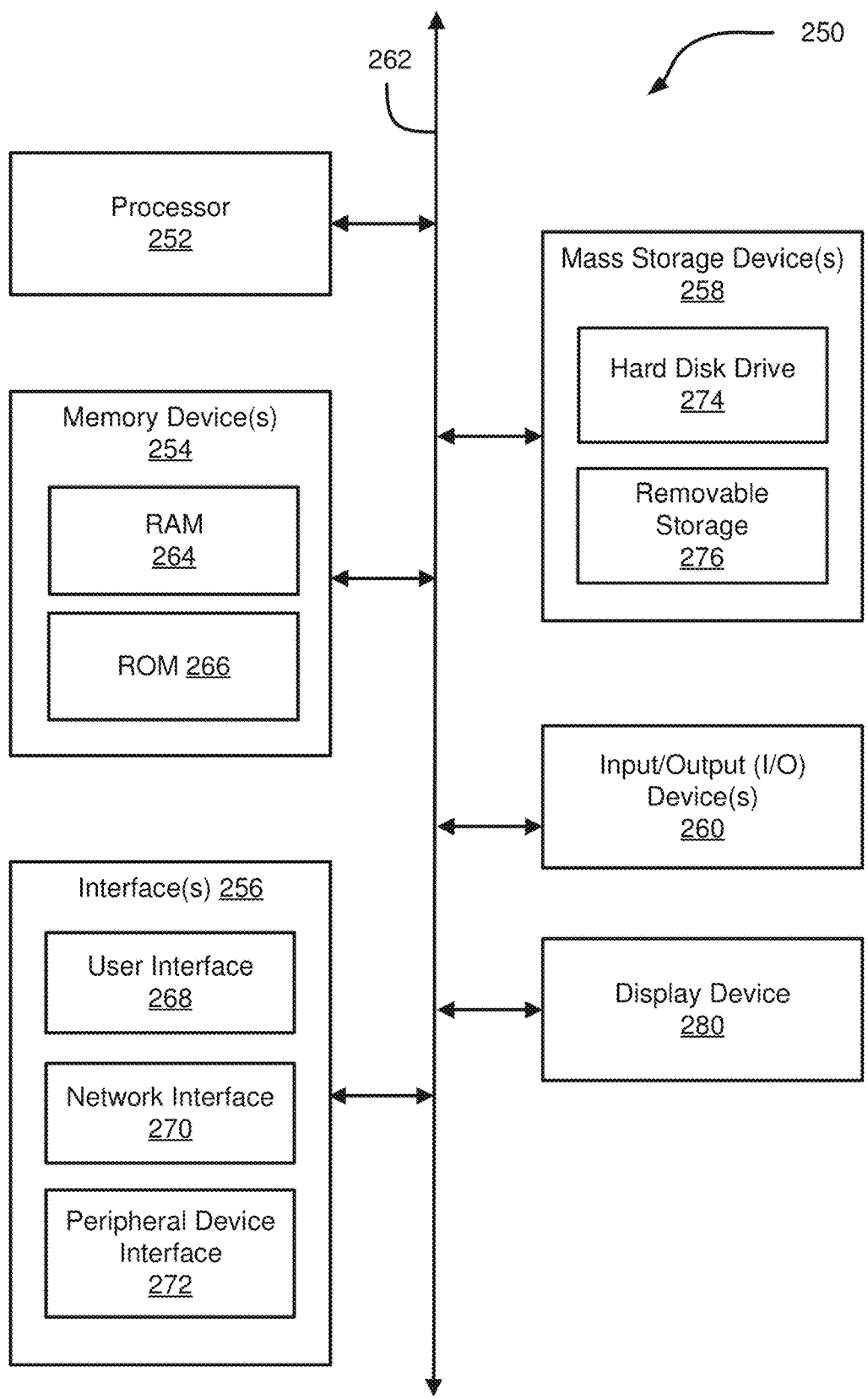
FIG. 2A is a schematic diagram of complementary system hardware.

FIG. 2A is a schematic diagram of complementary system hardware such as a special purpose or general-purpose computer. Implementations within the scope of the present disclosure may also include physical and other non-transitory computer readable media for carrying or storing computer executable instructions and/or data structures. Such computer readable media can be any available media that can be accessed by a general purpose or special purpose computer system. Computer readable media that stores computer executable instructions are computer storage media (devices). Computer readable media that carry computer executable instructions are transmission media. Thus, by way of example, and not limitation, implementations of the disclosure can comprise at least two distinctly different kinds of computer readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer executable instructions or data structures and which can be accessed by a general purpose or special purpose computer. Combinations of the above should also be included within the scope of computer readable media.

Further, upon reaching various computer system components, program code means in the form of computer executable instructions or data structures that can be transferred automatically from transmission media to computer storage media (devices) (or vice versa). For example, computer executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer executable instructions comprise, for example, instructions and data which, when executed by one or more processors, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2A is a block diagram illustrating an example computing device 250. Computing device 250 may be used to perform various procedures, such as those discussed herein. Computing device 250 can function as a server, a client, or any other computing entity. Computing device 250 can perform various monitoring functions as discussed herein, and can execute one or more application programs, such as the application programs described herein. Computing device 250 can be any of a wide variety of computing devices, such as a desktop computer, a notebook computer, a server computer, a handheld computer, camera control unit, tablet computer and the like.

Computing device 250 includes one or more processor(s) 252, one or more memory device(s) 254, one or more interface(s) 256, one or more mass storage device(s) 258, one or more Input/Output (I/O) device(s) 260, and a display device 280 all of which are coupled to a bus 262. Processor(s) 252 include one or more processors or controllers that execute instructions stored in memory device(s) 254 and/or mass storage device(s) 258. Processor(s) 252 may also include various types of computer readable media, such as cache memory.

Memory device(s) 254 include various computer readable media, such as volatile memory (e.g., random access memory (RAM) 264) and/or nonvolatile memory (e.g., read-only memory (ROM) 266). Memory device(s) 254 may also include rewritable ROM, such as Flash memory.

Mass storage device(s) 258 include various computer readable media, such as magnetic tapes, magnetic disks, optical disks, solid-state memory (e.g., Flash memory), and so forth. As shown in FIG. 2, a particular mass storage device is a hard disk drive 274. Various drives may also be included in mass storage device(s) 258 to enable reading from and/or writing to the various computer readable media. Mass storage device(s) 258 include removable media 276 and/or non-removable media.

I/O device(s) 260 include various devices that allow data and/or other information to be input to or retrieved from computing device 250. Example I/O device(s) 260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 280 includes any type of device capable of displaying information to one or more users of computing device 250. Examples of display device 280 include a monitor, display terminal, video projection device, and the like.

Interface(s) 256 include various interfaces that allow computing device 250 to interact with other systems, devices, or computing environments. Example interface(s) 256 may include any number of different network interfaces 270, such as interfaces to local area networks (LANs), wide area networks (WANs), wireless networks, and the Internet. Other interface(s) include user interface 268 and peripheral device interface 272. The interface(s) 256 may also include one or more user interface elements 268. The interface(s) 256 may also include one or more peripheral interfaces such as interfaces for printers, pointing devices (mice, track pad, etc.), keyboards, and the like.

Bus 262 allows processor(s) 252, memory device(s) 254, interface(s) 256, mass storage device(s) 258, and I/O device(s) 260 to communicate with one another, as well as other devices or components coupled to bus 262. Bus 262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 250 and are executed by processor(s) 252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 3A:
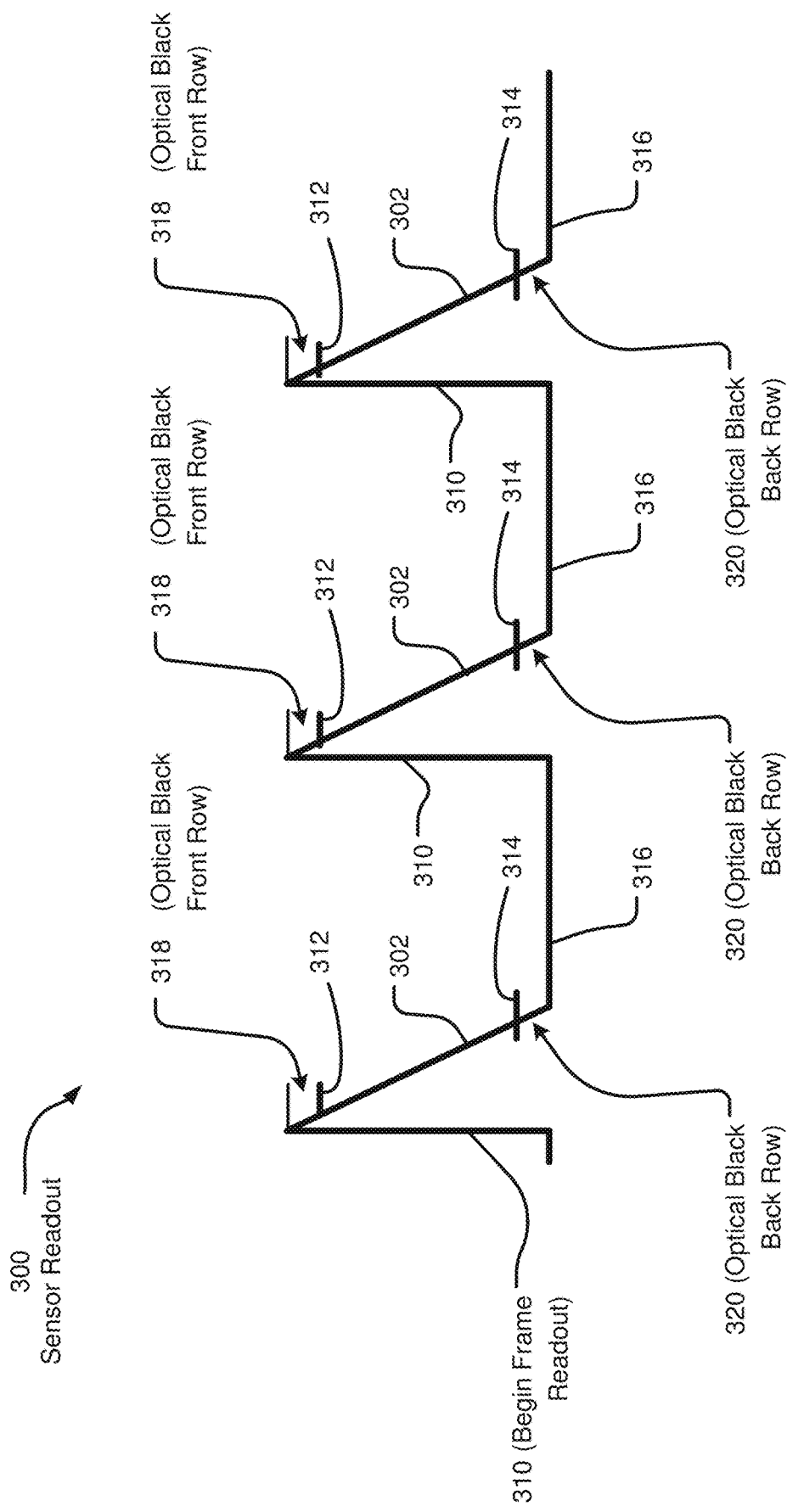

FIG. 3A illustrates the operational cycles of a sensor used in rolling readout mode or during the sensor readout 300. The frame readout may start at and may be represented by vertical line 310. The read-out period is represented by the diagonal or slanted line 302. The active pixels of the pixel array of the image sensor may be read out on a row by row basis, the top of the downwards slanted edge being the sensor top row 312 and the bottom of the downwards slanted edge being the sensor bottom row 314. The time between the last row readout and the next readout cycle may be called the blanking period 316. It should be noted that some of the sensor pixel rows might be covered with a light shield (e.g., a metal coating or any other substantially black layer of another material type). These covered pixel rows may be referred to as optical black rows 318 and 320. Optical black rows 318 and 320 may be used as input for correction algorithms. As shown in FIG. 3A, these optical black rows 318 and 320 may be located on the top of the pixel array or at the bottom of the pixel array or at the top and the bottom of the pixel array.

FIG. 3B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 322) may be used to start the integration time by resetting the pixel. The light will then integrate until the next readout phase. The position of the electronic shutter 322 can be moved between two readout cycles 302 to control the pixel saturation for a given amount of light. It should be noted that this technique allows for a constant integration time between two different lines but introduces a delay when moving from top to bottom rows.

FIG. 3C illustrates the case where the electronic shutter 322 has been removed. In this configuration, the integration of the incoming light may start during readout 302 and may end at the next readout cycle 302, which also defines the start of the next integration.

Figure 3D:
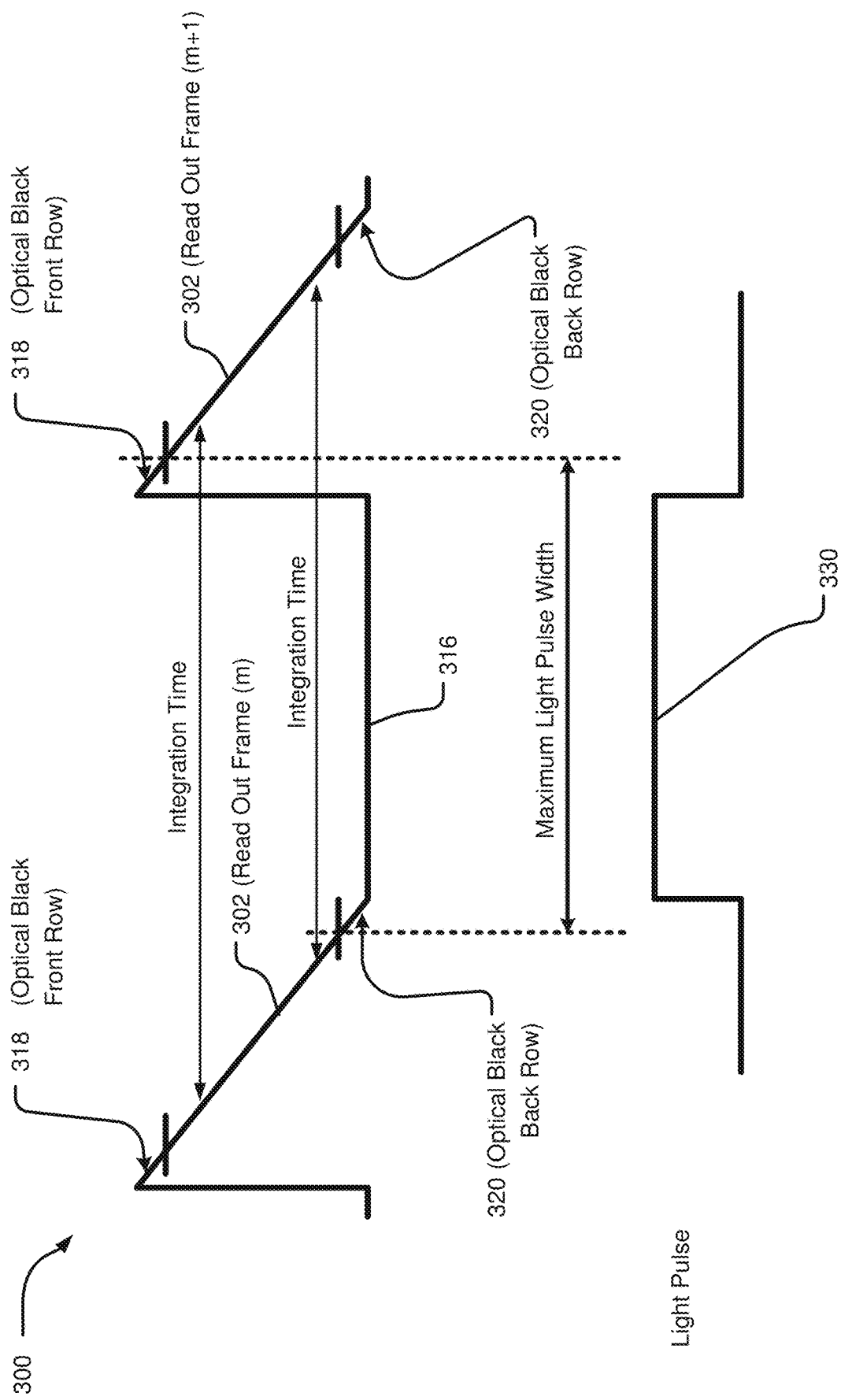

FIG. 3D shows a configuration without an electronic shutter 322, but with a controlled and pulsed light 330 during the blanking period 316. This ensures that all rows see the same light issued from the same light pulse 330. In other words, each row will start its integration in a dark environment, which may be at the optical black back row 320 of read out frame (m) for a maximum light pulse width, and will then receive a light strobe and will end its integration in a dark environment, which may be at the optical black front row 318 of the next succeeding read out frame (m+1) for a maximum light pulse width. In the FIG. 3D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking period 316. Because the optical black rows 318, 320 are insensitive to light, the optical black back rows 320 time of frame (m) and the optical black front rows 318 time of frame (m+1) can be added to the blanking period 316 to determine the maximum range of the firing time of the light pulse 330.

As illustrated in the FIG. 3A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 4A:
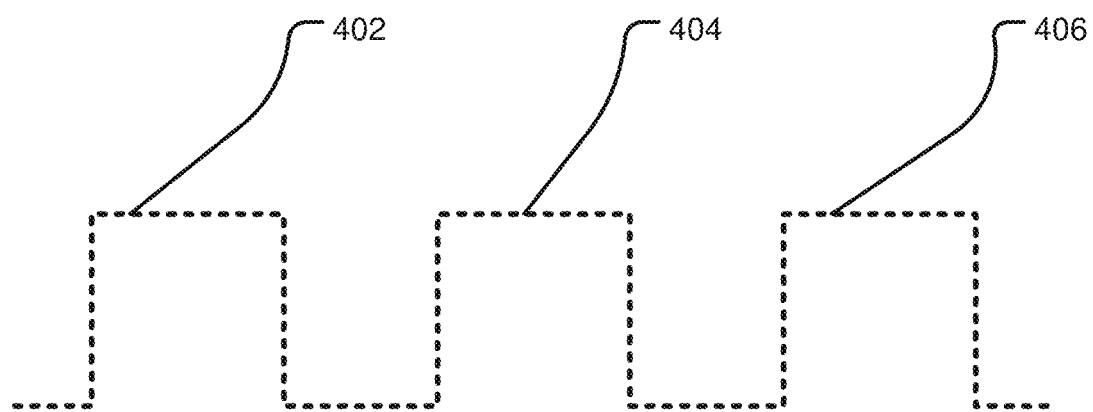
FIG. 4A is a graphical representation of the operation of an embodiment of an electromagnetic emitter.

FIG. 4A graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 4A illustrates Pulse 1 at 402, Pulse 2 at 404, and Pulse 3 at 406. In an embodiment, the emitter may pulse during the readout period 302 of the sensor operation cycle. In an embodiment, the emitter may pulse during the blanking portion 316 of the sensor operation cycle. In an embodiment, the emitter may pulse for a duration that is during portions of two or more sensor operational cycles. In an embodiment, the emitter may begin a pulse during the blanking portion 316, or during the optical black portion 320 of the readout period 302, and end the pulse during the readout period 302, or during the optical black portion 318 of the readout period 302 of the next succeeding cycle. It will be understood that any combination of the above is intended to fall within the scope of this disclosure as long as the pulse of the emitter and the cycle of the sensor correspond.

Figure 4B:
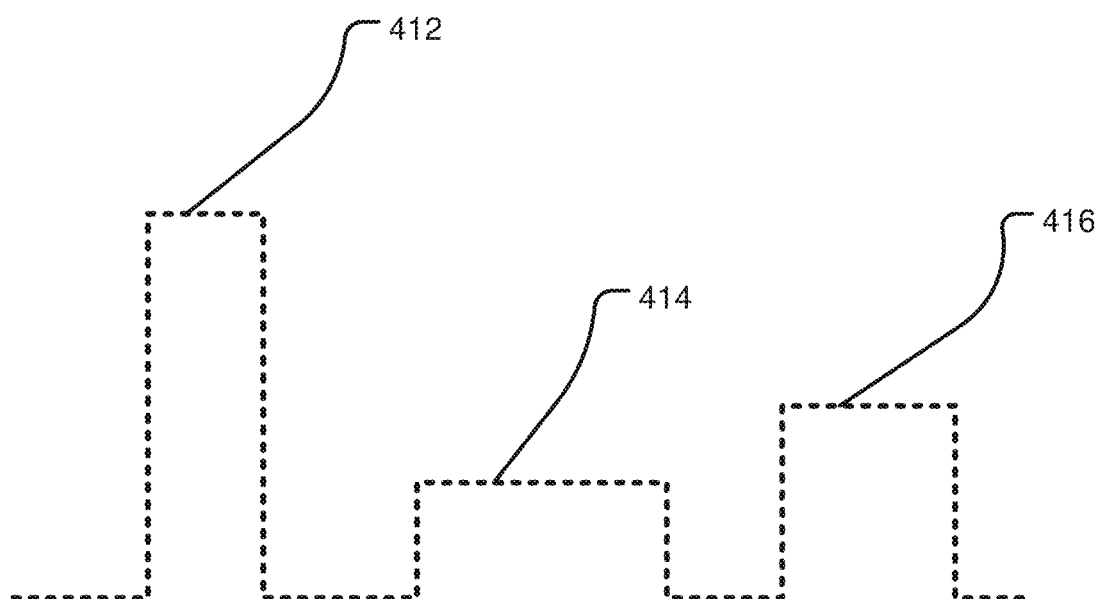
FIG. 4B is a graphical representation of varying the duration and magnitude of the emitted electromagnetic pulse to provide exposure control.

FIG. 4B graphically represents varying the duration and magnitude of the emitted electromagnetic pulse (e.g., Pulse 1 at 412, Pulse 2 at 414, and Pulse 3 at 416) to control exposure. An emitter having a fixed output magnitude may be pulsed during any of the cycles noted above in relation to FIGS. 3D and 4A for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4B illustrates varying the magnitude and duration of the pulses. In the illustration, Pulse 1 at 412 has a higher magnitude or intensity than either Pulse 2 at 414 or Pulse 3 at 416. Additionally, Pulse 1 at 412 has a shorter duration than Pulse 2 at 414 or Pulse 3 at 416, such that the electromagnetic energy provided by the pulse is illustrated by the area under the pulse shown in the illustration. In the illustration, Pulse 2 at 414 has a relatively low magnitude or intensity and a longer duration when compared to either Pulse 1 at 412 or Pulse 3 at 416. Finally, in the illustration, Pulse 3 at 416 has an intermediate magnitude or intensity and duration, when compared to Pulse 1 at 412 and Pulse 2 at 414.

Figure 5:
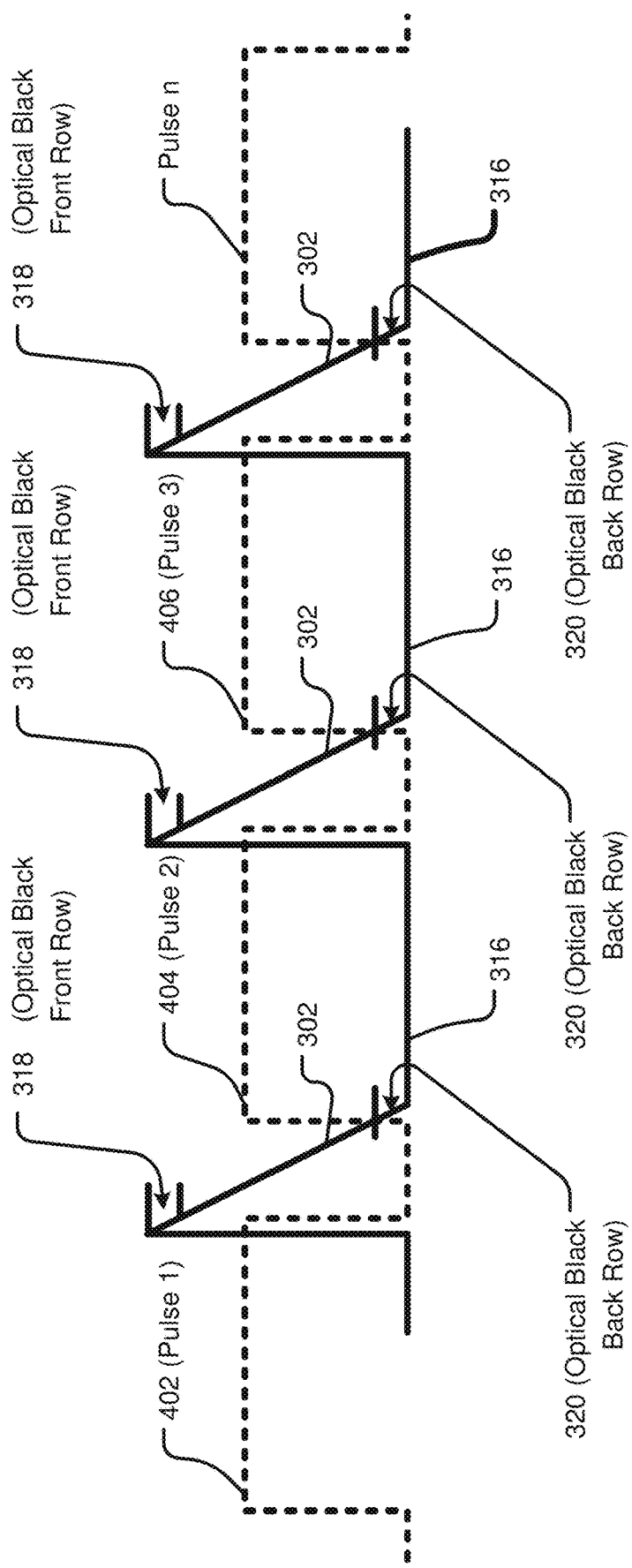
FIG. 5 is a graphical representation of an embodiment of the disclosure combining the operational cycles of a sensor, the electromagnetic emitter, and the emitted electromagnetic pulses of FIGS. 3A-4A, which demonstrate the imaging system during operation.

FIG. 5 is a graphical representation of an embodiment of the disclosure combining the operational cycles, the electromagnetic emitter, and the emitted electromagnetic pulses of FIGS. 3A-3D and 4A to demonstrate the imaging system during operation in accordance with the principles and teachings of the disclosure. As can be seen in the figure, the electromagnetic emitter pulses the emissions primarily during the blanking period 316 of the image sensor such that the pixels will be charged and ready to read during the readout period 302 of the image sensor cycle. The dashed lines in FIG. 5 represent the pulses of electromagnetic radiation (from FIG. 4A). The pulses of electromagnetic radiation are primarily emitted during the blanking period 316 of the image sensor but may overlap with the readout period 302 of the image sensor.

An exposure frame includes the data read by the pixel array of the image sensor during a readout period 302. The exposure frame may be combined with an indication of what type of pulse was emitted by the emitter prior to the readout period 302. The combination of the exposure frame and the indication of the pulse type may be referred to as a dataset. Multiple exposure frames may be combined to generate a black-and-white or RGB color image. Additionally, hyperspectral, fluorescence, and/or laser mapping imaging data may be overlaid on a black-and-white or RGB image.

In an embodiment, an exposure frame is the data sensed by the pixel array during the readout period 302 that occurs subsequent to a blanking period 316. The emission of electromagnetic radiation is emitted during the blanking period 316. In an embodiment, a portion of the emission of electromagnetic radiation overlaps the readout period 316. The blanking period 316 occurs when optical black pixels of the pixel array are being read and the readout period 302 occurs when active pixels of the pixel array are being read. The blanking period 316 may overlap the readout period 302.

FIGS. 6A and 6B illustrate processes for recording an image frame. Multiple image frames may be strung together to generate a video stream. A single image frame may include data from multiple exposure frames, wherein an exposure frame is the data sensed by a pixel array subsequent to an emission of electromagnetic radiation. FIG. 6A illustrates a traditional process that is typically implemented with a color image sensor having a color filter array (CFA) for filtering out certain wavelengths of light per pixel. FIG. 6B is a process that is disclosed herein and can be implemented with a monochromatic "color agnostic" image sensor that is receptive to all wavelengths of electromagnetic radiation.

The process illustrated in FIG. 6A occurs from time t(0) to time t(1). The process begins with a white light emission 602 and sensing white light 604. The image is processed and displayed at 606 based on the sensing at 604.

The process illustrated in FIG. 6B occurs from time t(0) to time t(1). The process begins with an emission of green light 612 and sensing reflected electromagnetic radiation 614 subsequent to the emission of green light 612. The process continues with an emission of red light 616 and sensing reflected electromagnetic radiation 618 subsequent to the emission of red light 616. The process continues with an emission of blue light 620 and sensing reflected electromagnetic radiation 622 subsequent to the emission of blue light 620. The process continues with one or more emissions of a laser mapping 624 pulsing scheme and sensing reflected electromagnetic energy 626 subsequent to each of the one or more emissions of the laser mapping 624 pulsing scheme. The image is processed and displayed at 628 based on each of the sensed reflected electromagnetic energy instances 614, 618, 622, and 626.

The process illustrated in FIG. 6B provides a higher resolution image and provides a means for generating an RGB image that further includes laser mapping data. When partitioned spectrums of light are used, (as in FIG. 6B) a sensor can be made sensitive to all wavelengths of electromagnetic energy. In the process illustrated in FIG. 6B, the monochromatic pixel array is instructed that it is sensing electromagnetic energy from a predetermined partition of the full spectrum of electromagnetic energy in each cycle. Therefore, to form an image the sensor need only be cycled with a plurality of differing partitions from within the full spectrum of light. The final image is assembled based on the multiple cycles. Because the image from each color partition frame cycle has a higher resolution (compared with a CFA pixel array), the resultant image created when the partitioned light frames are combined also has a higher resolution. In other words, because each and every pixel within the array (instead of, at most, every second pixel in a sensor with a CFA) is sensing the magnitudes of energy for a given pulse and a given scene, just fractions of time apart, a higher resolution image is created for each scene.

As can be seen graphically in the embodiments illustrated in FIGS. 6A and 6B between times t(0) and t(1), the sensor for the partitioned spectrum system in FIG. 6B has cycled at least four times for every one of the full spectrum system in FIG. 6A. In an embodiment, a display device (LCD panel) operates at 50-60 frames per second. In such an embodiment, the partitioned light system in FIG. 6B may operate at 200-240 frames per second to maintain the continuity and smoothness of the displayed video. In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
 i. Green pulse;
 ii. Red pulse;
 iii. Blue pulse;
 iv. Green pulse;
 v. Red pulse;
 vi. Blue pulse;
 vii. Laser mapping pulsing scheme;
 viii. (Repeat)

As can be seen in the example, a laser mapping partition may be pulsed at a rate differing from the rates of the other partition pulses. This may be done to emphasize a certain aspect of the scene, with the laser mapping data simply being overlaid with the other data in the video output to make the desired emphasis. It should be noted that the addition of a laser mapping partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a partition pulse that is represented less in a pulse pattern (laser mapping in the above example), would result in an increase of less than 20% of the cycling speed of the sensor to accommodate the irregular partition sampling.

Figure 7A:
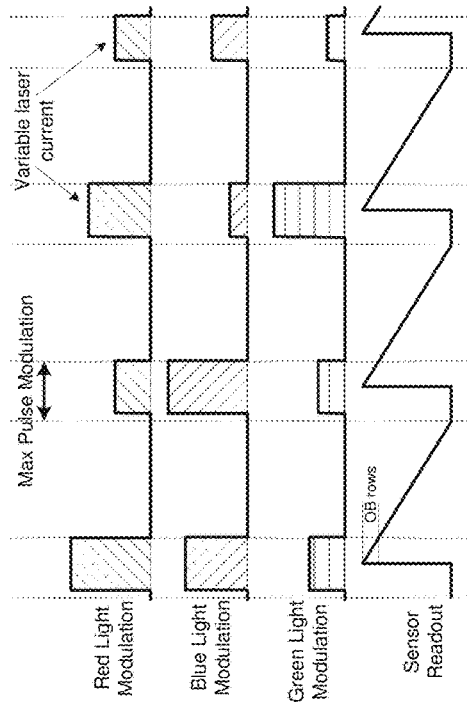
FIGS. 7A-7E illustrate schematic views of processes over an interval of time for recording a frame of video for both full spectrum light and partitioned spectrum light.
Figure 7B:
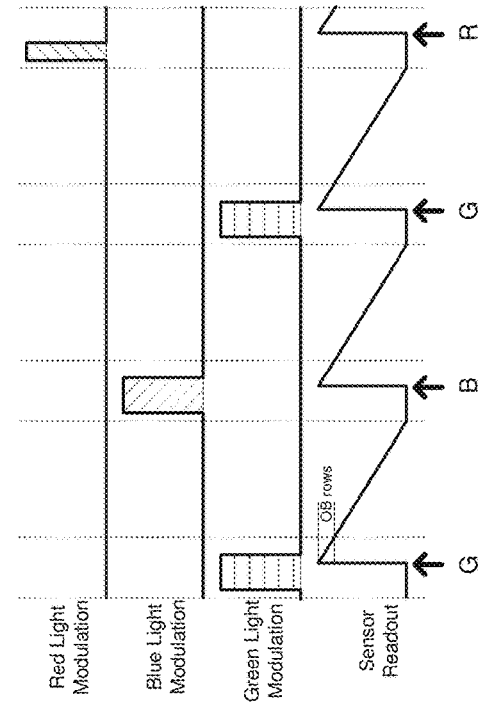
Figure 7C:
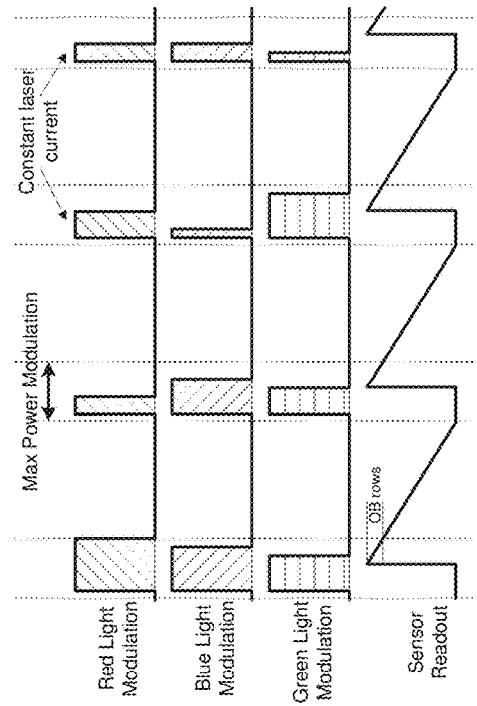

The partition cycles may be divided so as to accommodate or approximate various imaging and video standards. In an embodiment, the partition cycles may comprise pulses of electromagnetic energy in the Red, Green, and Blue spectrum as follows as illustrated best in FIGS. 7A-7D. In FIG. 7A, the different light intensities have been achieved by modulating the light pulse width or duration within the working range shown by the vertical grey dashed lines. In FIG. 7B, the different light intensities have been achieved by modulating the light power or the power of the electromagnetic emitter, which may be a laser or LED emitter, but keeping the pulse width or duration constant. FIG. 7C shows the case where both the light power and the light pulse width are being modulated, leading to greater flexibility. The partition cycles may use Cyan Magenta Yellow (CMY), infrared, ultraviolet, hyperspectral, and fluorescence using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

Figure 7D:
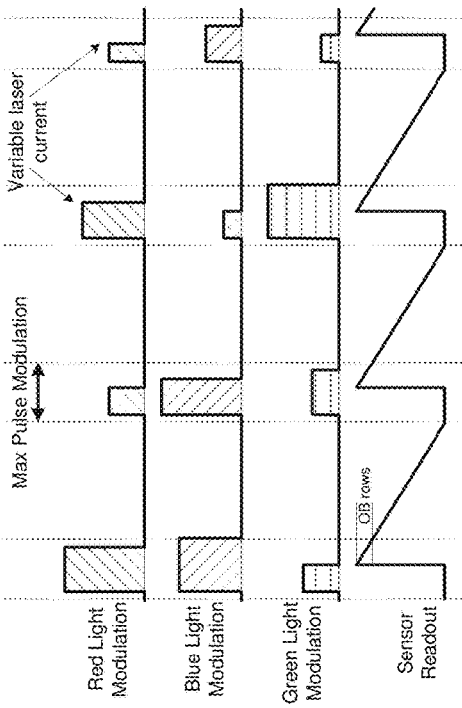

In an embodiment using color spaces Green-Blue-Green-Red (as seen in FIG. 7D) it may be desirous to pulse the luminance components more often than the chrominance components because users are generally more sensitive to light magnitude differences than to light color differences. This principle can be exploited using a mono-chromatic sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

Figure 7E:
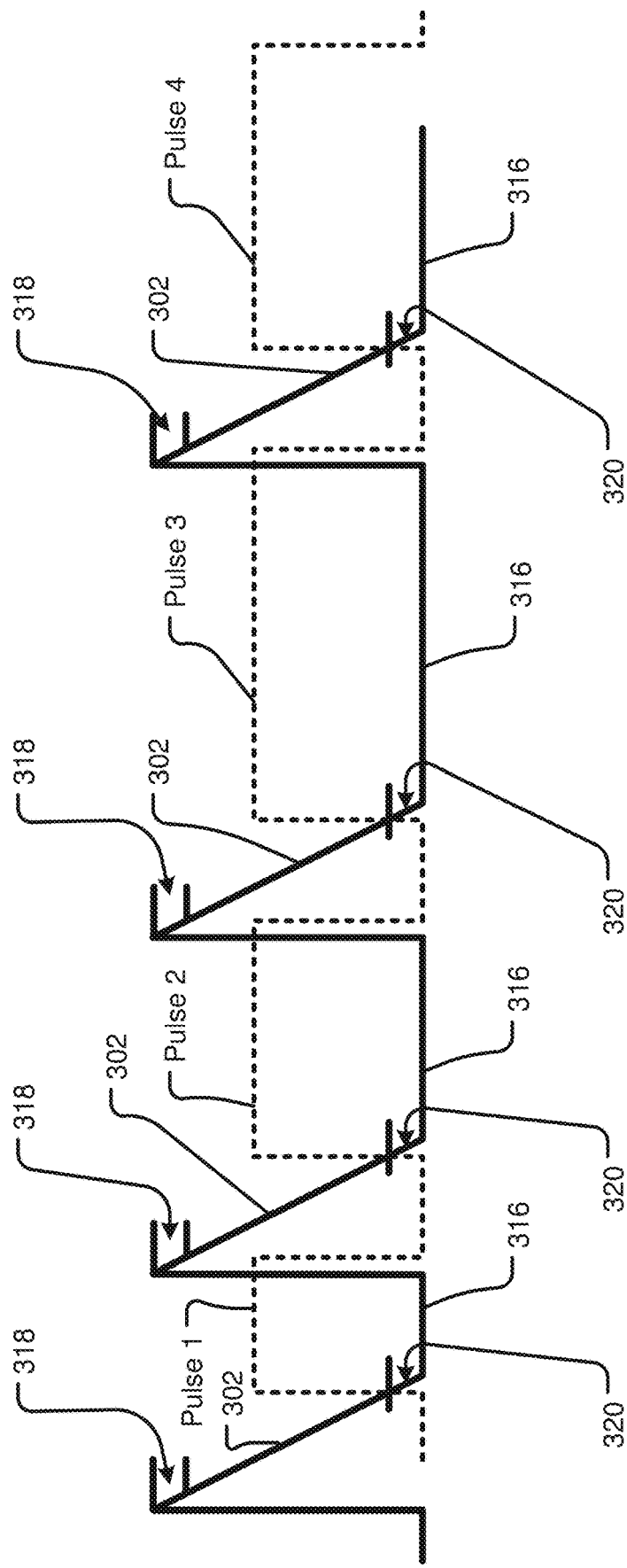

In an embodiment, duplicating the pulse of a weaker partition may be used to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E, where the light pulses are different from frame to frame. The sensor may be built to be able to program different blanking periods with a repeating pattern of two or three or four or n frames. In FIG. 7E, four different light pulses are illustrated, and Pulse 1 may repeat for example after Pulse 4 and may have a pattern of four frames with different blanking periods. This technique can be used to place the most powerful partition on the smallest blanking period and therefore allow the weakest partition to have wider pulse on one of the next frames without the need of increasing the readout speed. The reconstructed frame can still have a regular pattern from frame to frame as it is constituted of many pulsed frames.

FIGS. 8-11 illustrate example embodiments of a pixel array comprising a plurality of pixels, wherein the pixels are alternated from frame to frame.

Figure 8:
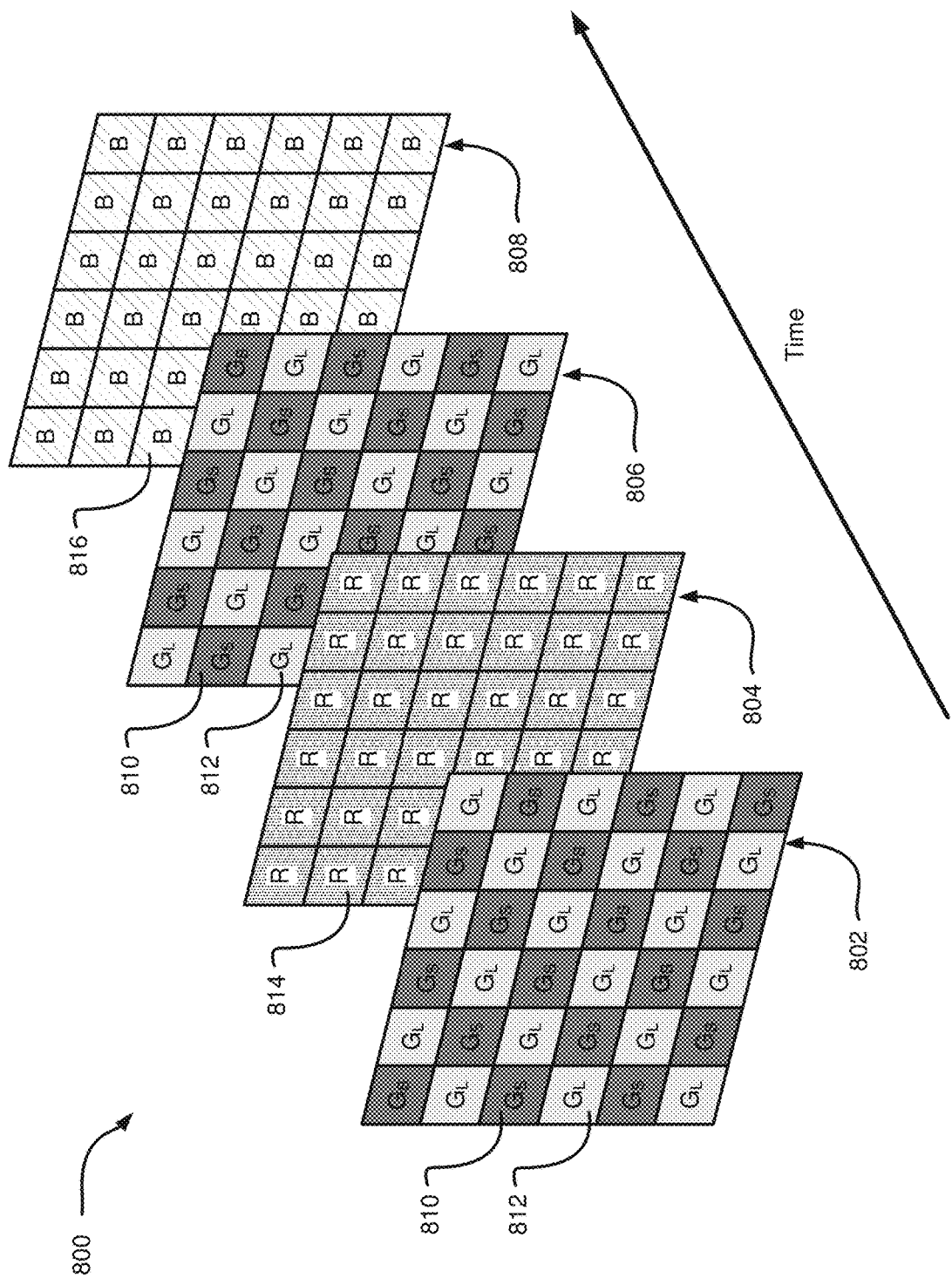
FIG. 8 is a graphical representation of a pixel array comprising a plurality of pixels in different orientations for capturing independent exposure frames over time for generating an RGB image frame.

FIG. 8 illustrates a pixel array 800 comprising a plurality of pixels. The pixels of the pixel array 800 are depicted as discrete squares. The pixel array 800 is configured for sensing reflected electromagnetic radiation for generating an RGB image frame based on a plurality of independent exposure frames. The pixel array 800 is illustrated with four different configurations over time, including configurations for a first exposure frame 802, a second exposure frame 804, a third exposure frame 806, and a fourth exposure frame 808. The first exposure frame 802, the second exposure frame 804, the third exposure frame 806, and the fourth exposure frame 808 may be combined to generate a single RGB image frame. One or more additional exposure frames may be combined with or overlaid on the RGB image frame, including for example, a hyperspectral exposure frame, a fluorescence exposure frame, and/or a laser mapping exposure frame.

When the pixel array 800 is configured for the first exposure frame 802, the pixels are configured as green short exposure pixels 810 (notated with $G_S$) and green long exposure pixels 812 (notated with $G_L$) arranged in a checkerboard pattern. The pixel array 800 configuration for the second exposure frame 804 includes red pixels 806 (notated with R). The configuration for the third exposure frame 806 includes pixels configured as green short exposure pixels 810 and green long exposure pixels 812 arranged in a checkerboard pattern in an opposite configuration with respect to the first exposure frame 802. The configuration for the fourth exposure frame 808 includes blue exposure frames 818 (notated with B). This approach of including long exposure pixels and short exposure pixels increases the perceived resolution of the resulting image. The interpolated locations of the long exposure pixels and the short exposure pixels may be swapped from exposure frame to exposure frame, for example as illustrated in the first exposure frame 802 and the third exposure frame 806.

Figure 9:
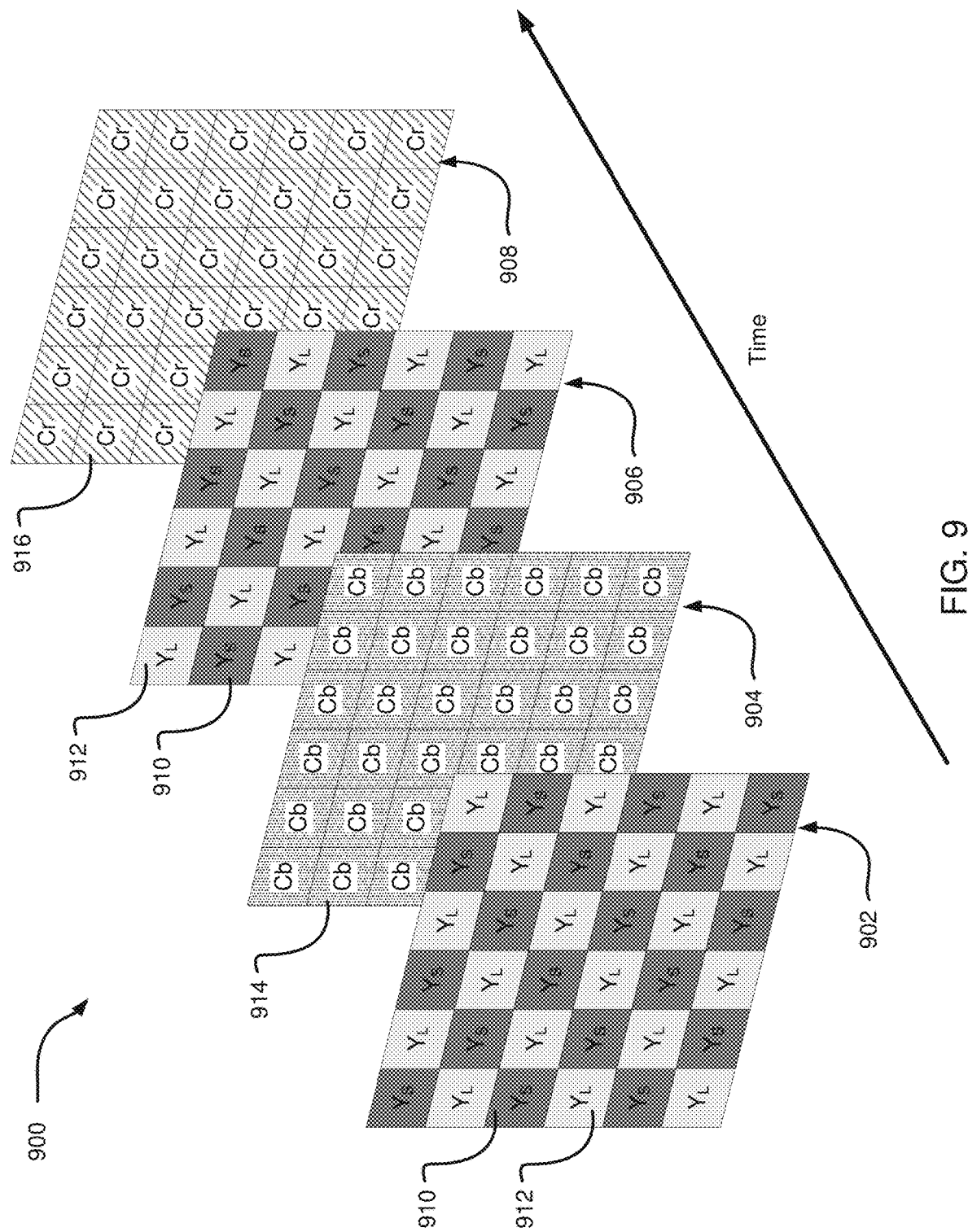
FIG. 9 is a graphical representation of a pixel array comprising a plurality of pixels in different orientations for capturing independent exposure frames over time for generating a YCbCr image frame.

FIG. 9 illustrates a pixel array 900 comprising a plurality of pixels. The pixel array 900 is configured for sensing reflected electromagnetic radiation for generating a YCbCr image frame based on a plurality of independent exposure frames. The pixel array 900 is illustrated with four different configurations over time, including configurations for a first exposure frame 902, a second exposure frame 904, a third exposure frame 906, and a fourth exposure frame 908. The data sensed by the pixel array 900 for the multiple exposure frames 902, 904, 906, 908 can be combined to generate a single YCbCr image frame. The configuration of the pixels for the first exposure frame 902 includes luminance short exposure pixels 910 (notated with $Y_S$) and luminance long exposure pixels 912 (notated with $Y_L$) arranged in a checkerboard pattern. The configuration for the second exposure frame 904 includes chrominance blue pixels 914 (notated with Cb). The configuration for the third exposure frame 906 includes luminance short exposure pixels 910 and luminance long exposure pixels 912 arranged in a checkerboard pattern in an opposite configuration with respect to the first exposure frame 902. The configuration for the fourth exposure frame 908 includes chrominance red pixels 916 (notated with Cr).

Figure 10:
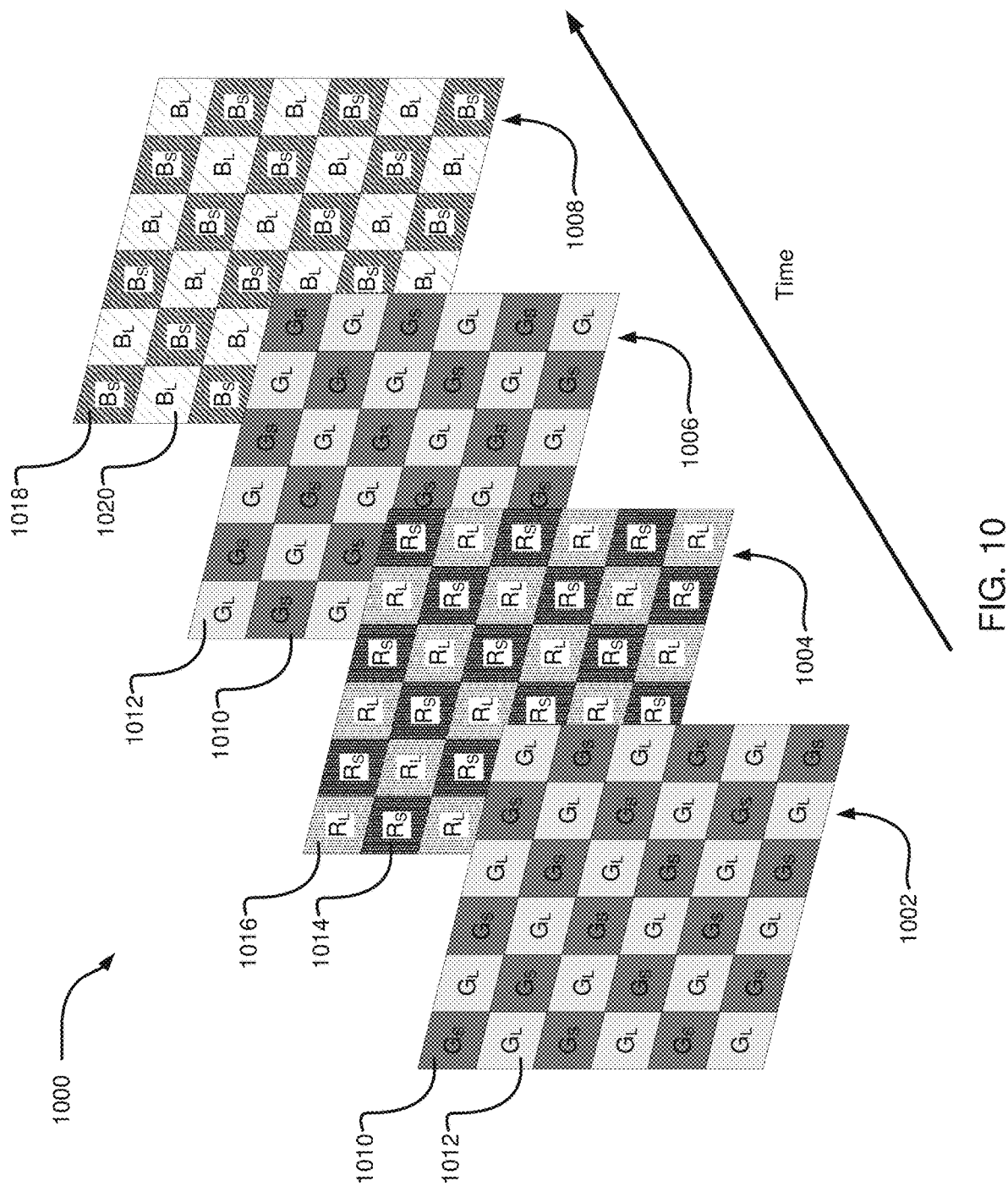
FIG. 10 is a graphical representation of a pixel array comprising a plurality of pixels in different orientations for capturing independent exposure frames over time for generating an RGB image frame.

FIG. 10 illustrates a pixel array 1000 comprising a plurality of pixels. The pixel array 1000 is configured for sensing reflected electromagnetic radiation for generating an RGB image based on a plurality of independent exposure frames. The pixel array 1000 is illustrated with four different configurations over time, including configurations for a first exposure frame 1002, a second exposure frame 1004, a third exposure frame 1006, and a fourth exposure frame 1008. The data sensed by the pixel array 1000 for the multiple exposure frames 1002, 1004, 1006, 1008 can be combined to generate a single RGB image frame. The configuration of the pixels for the first exposure frame 1002 includes green short exposure pixels 1010 (notated with $G_S$) and green long exposure pixels 1012 (notated with $G_L$) arranged in a checkerboard pattern. The configuration for the second exposure frame 1004 includes red short exposure pixels 1014 (notated with $R_S$) and red long exposure pixels 1016 (notated with $R_L$). The configuration for the third exposure frame 1006 includes green short exposure pixels 1010 and green long exposure pixels 1012 arranged in a checkerboard pattern with an opposite configuration with respect to the arrangement for the first exposure frame 1002. The configuration for the fourth exposure frame 1008 includes blue short exposure pixels 1018 (notated with $B_S$) and blue long exposure pixels 1020 (notated with $B_L$) arranged in a checkerboard pattern.

Figure 11:
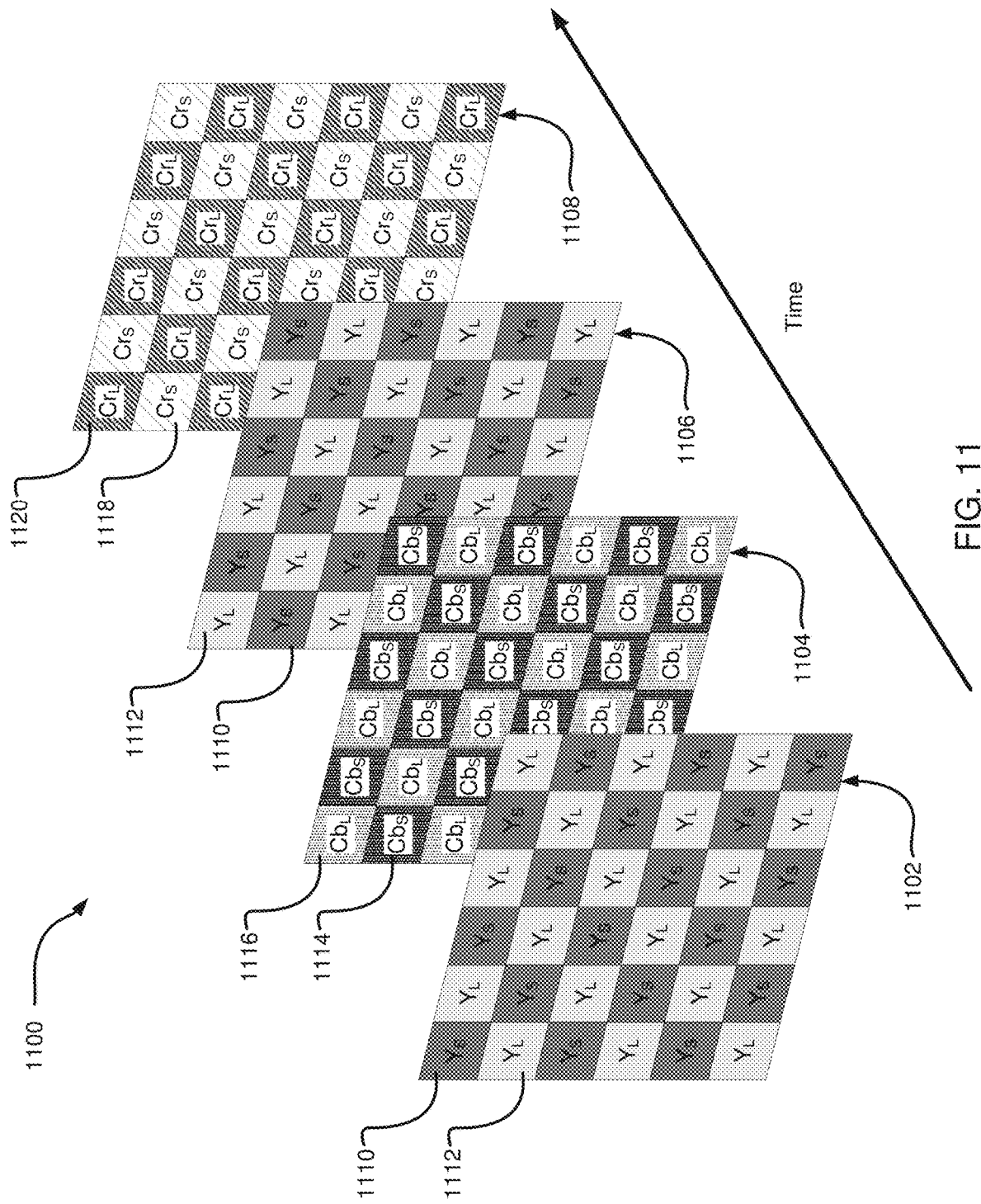
FIG. 11 is a graphical representation of a pixel array comprising a plurality of pixels in different orientations for capturing independent exposure frames over time for generating a YCbCr image frame.

FIG. 11 illustrates a pixel array 1100 comprising a plurality of pixels. The pixel array 900 is configured for sensing reflected electromagnetic radiation for generating a YCbCr image frame based on a plurality of independent exposure frames. The pixel array 1100 is illustrated with four different configurations over time, including configurations for a first exposure frame 1102, a second exposure frame 1104, a third exposure frame 1106, and a fourth exposure frame 1108. The data sensed by the pixel array 1100 for the multiple exposure frames 1102, 1104, 1106, 1108 can be combined to generate a single YCbCr image frame. The configuration of the pixels for the first exposure frame 1102 includes luminance short exposure pixels 1110 (notated with $Y_S$) and luminance long exposure pixels 1112 (notated with $Y_L$) arranged in a checkerboard pattern. The configuration for the second exposure frame 1104 includes chrominance blue short exposure pixels 1114 (notated with $Cb_S$) and chrominance blue long exposure pixels 1116 (notated with $Cb_L$) arranged in a checkerboard pattern. The configuration for the third exposure frame 1106 includes luminance short exposure pixels 1110 and luminance long exposure pixels 1112 arranged in a checkerboard pattern in an opposite configuration with respect to the first exposure frame 1102. The configuration for the fourth exposure frame 1108 includes chrominance red short exposure pixels 1118 (notated with $Cr_S$) and chrominance red long exposure pixels 1120 (notated with $Cr_L$) arranged in a checkerboard pattern.

As illustrated in FIGS. 10 and 11, the application of dual exposure exampling is not limited to green exposure frames or luminance exposure frames. In an embodiment, the pixels have independent dual exposure ratios applied for the red exposure frames, blue exposure frames, chrominance red exposure frames, and/or chrominance blue exposure frames as applicable.

FIGS. 12-15 illustrate different embodiments for a pixel array circuit arrangement. In some embodiments, the dynamic range of a resultant exposure frame is enhanced by spatially binning signals from the pixels within the pixel array. A pixel array may be configured in a two-way shared architecture that provides a means for two-way binning of pixels. This may be deployed in conjunction with simultaneous pulsing of the TX1 and TX2 signals and results in photo signals being transferred to the shard floating diffusion at the same time. When each row is subsequently read out, the row has two times the charge range with the same noise as compared with an un-binned case, and therefore has an additional 6 dB of dynamic range.

An advantage of the monochrome image sensor is that neighboring pixels within the pixel array can be binned together. Binning enables a greater reach of signal and thus greater dynamic range. The location of pixel binning dictates the effectiveness for increasing dynamic range of resultant exposure frames. For example, binning two adjacent pixels (may be referred to as two-way binning) may be done in the digital domain such that an additional factor two (6 dB) of signal is realized. However, there may be two analog samples each contributing an equal amount of read noise amounting to a factor $\sqrt{2}$ (3 dB) of noise enhancement. Therefore, the binning of data from two pixels at a point later in the chain than the source of read noise amounts to 3 dB of additional dynamic range. However, if binning is performed in the charge domain, i.e., at the pixel level, then the additional dynamic range may be 6 dB because the addition of readout noise occurs after the summation of signal.

Figure 12:
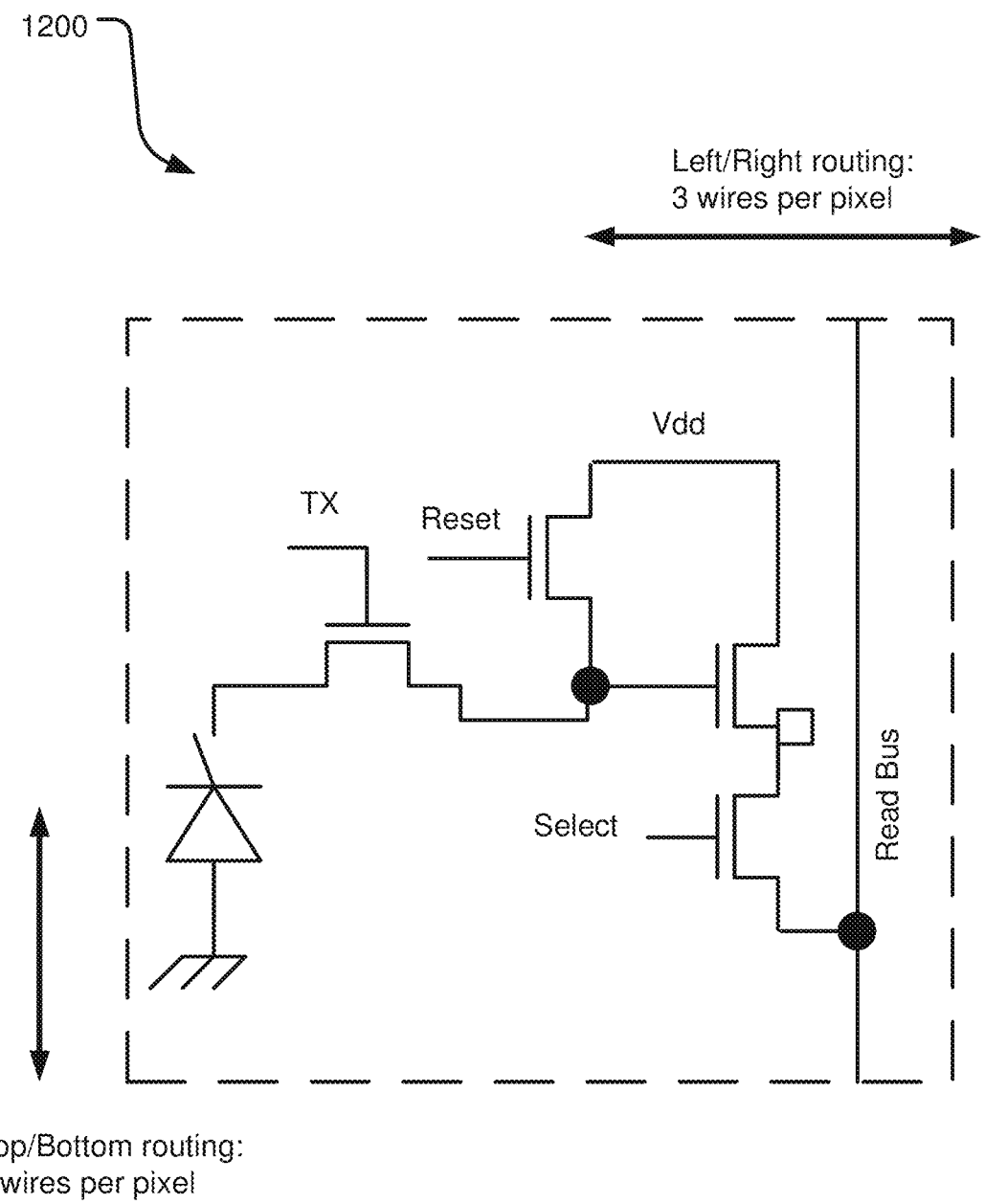
FIG. 12 is a circuit diagram for a pixel array that employs conventional unshared pixels.

FIG. 12 is a circuit diagram for a pixel array 1200 that employs conventional unshared pixels. The pixel array 1200 includes four transistors to facilitate low noise and to correlate double sampling. The pixel array 1200 may include five service wires as shown in the circuit diagram. Three of the four transistors may be shared between two or more neighboring pixels within the conventional unshared pixel array 1200, and this increases the available area for the photodiode. As pixel size is reduced, it becomes more challenging to maintain quantum efficiency because the photodiode occupies a smaller proportion of the area.

Figure 13:
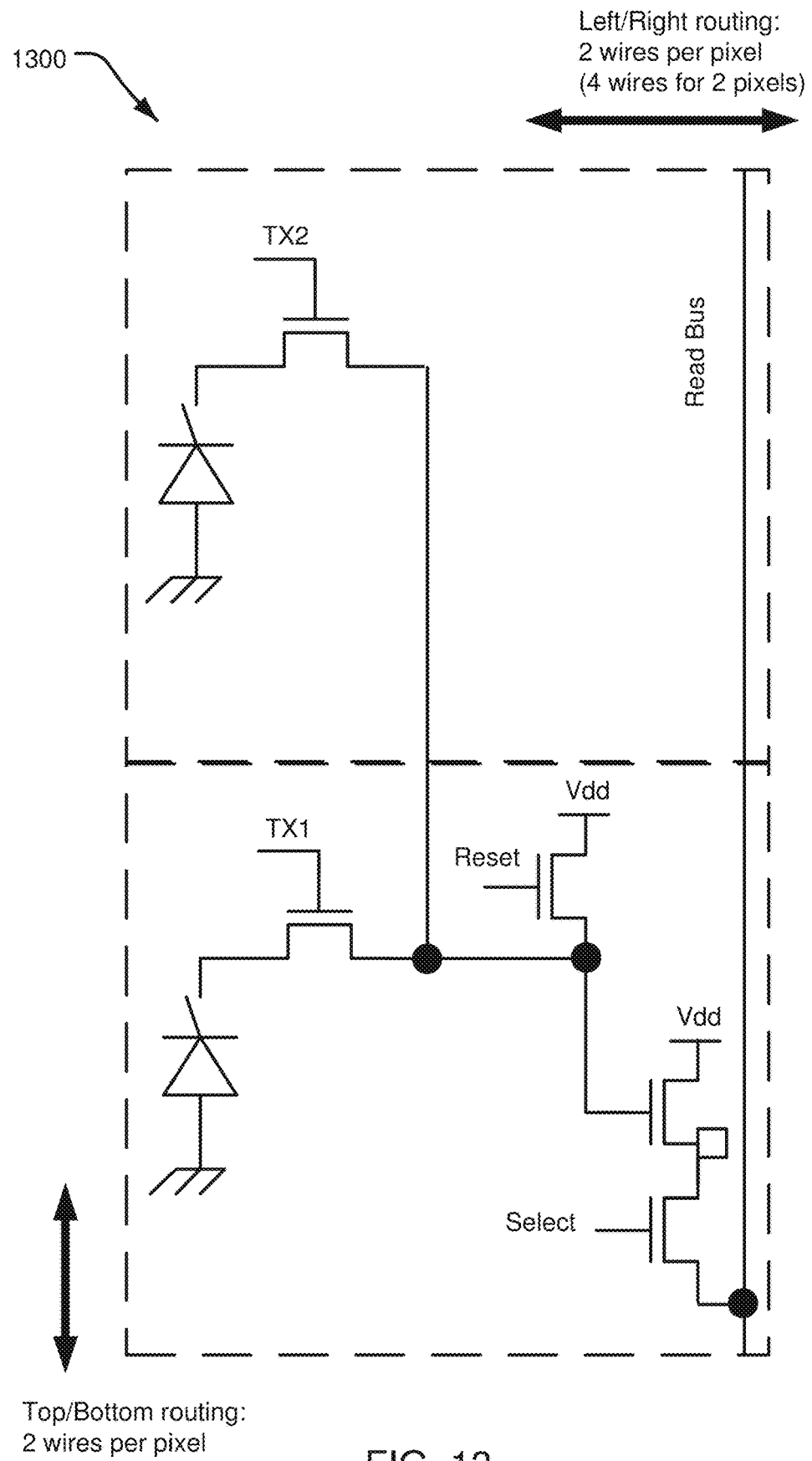
FIG. 13 is a unit cell for a pixel array that employs conventional two-way vertical sharing.

FIG. 13 is a unit cell for a pixel array 1300 with conventional two-way vertical sharing. The pixel array 1300 includes five transistors total for every two pixels such that there are 2.5 transistors per pixel. The pixel array 1300 may include six wires for each pixel pair such that four of the wires may be horizontally routed and two of the wires may be vertically routed as illustrated in FIG. 13. This results in two wires per pixel edge in each dimension, and this is in contrast with the unshared pixels having three horizontal and two vertical wires per pixel edge.

Figure 14:
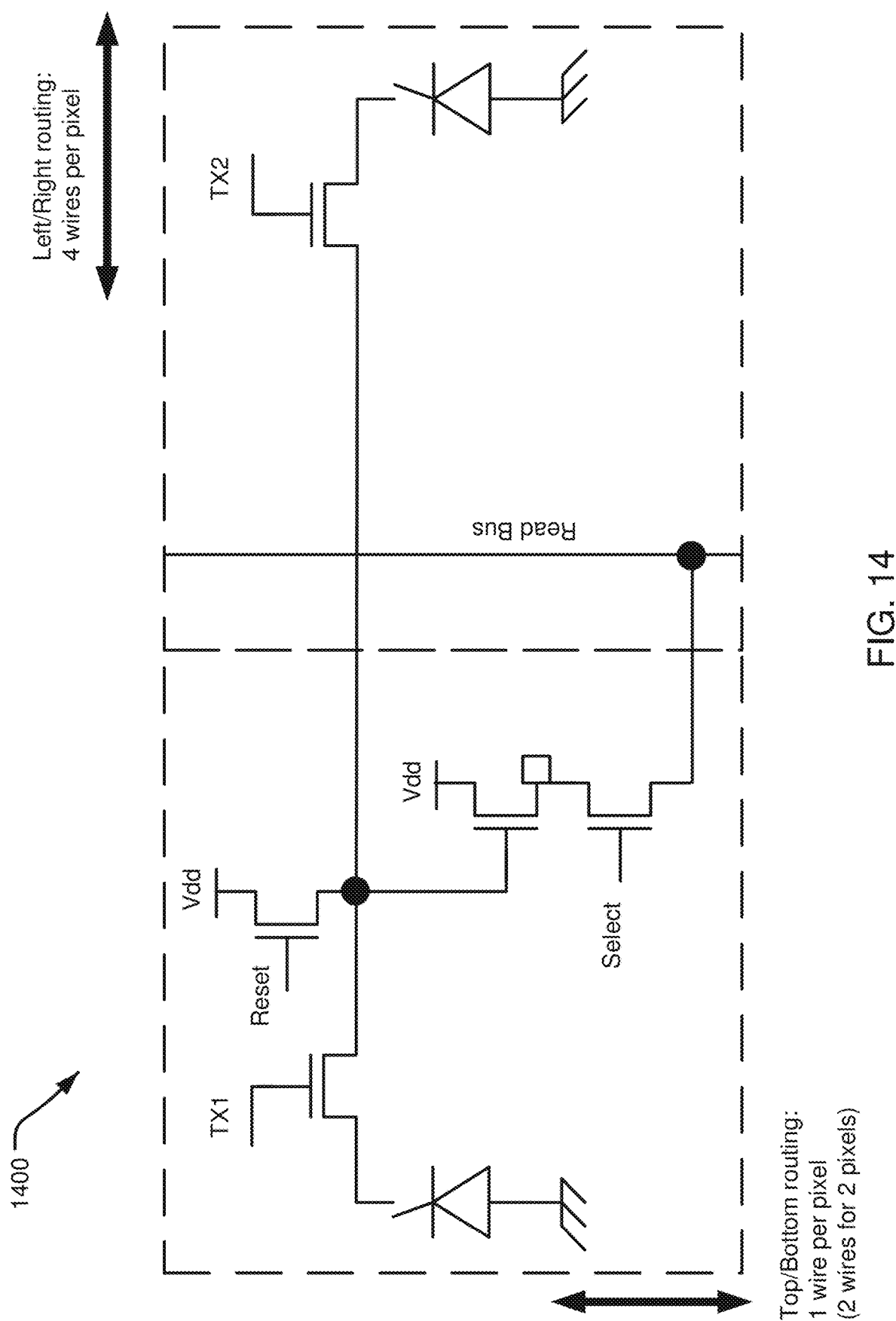
FIG. 14 is a circuit diagram for a pixel array in which pixels are paired horizontally rather than vertically.

FIG. 14 is a circuit diagram for a pixel array 1400 in which pixels are paired horizontally rather than vertically. The implementation illustrated in FIG. 14 may be less favorable with respect to wire routing simplicity because the four horizontal wires must now fit on a single pixel edge. However, in some implementations, the pixel array 1400 can offer benefits that outweigh this disadvantage. One benefit of the pixel array 1400 is that only half of the net circuitry is required to service each column of pixels. This reduces the overall chip area for the pixel array because the column circuitry can consume significant physical chip space.

An additional benefit of the pixel array 1400 illustrated in FIG. 14 is that sharing provides two independent transfer gate transistor (TX) signals per row. This opens the possibility to have two independent exposures within a single row. The two independent exposures per single row may alternate between odd columns and even columns (e.g., as illustrated in FIGS. 8-11 and 15). The checkerboard arrangement of dual exposures is made possible by switching the transfer gate transistor one (TX1) and transfer gate transistor two (TX2) odd/even column associations on alternate rows (see FIG. 15).

Figure 15:
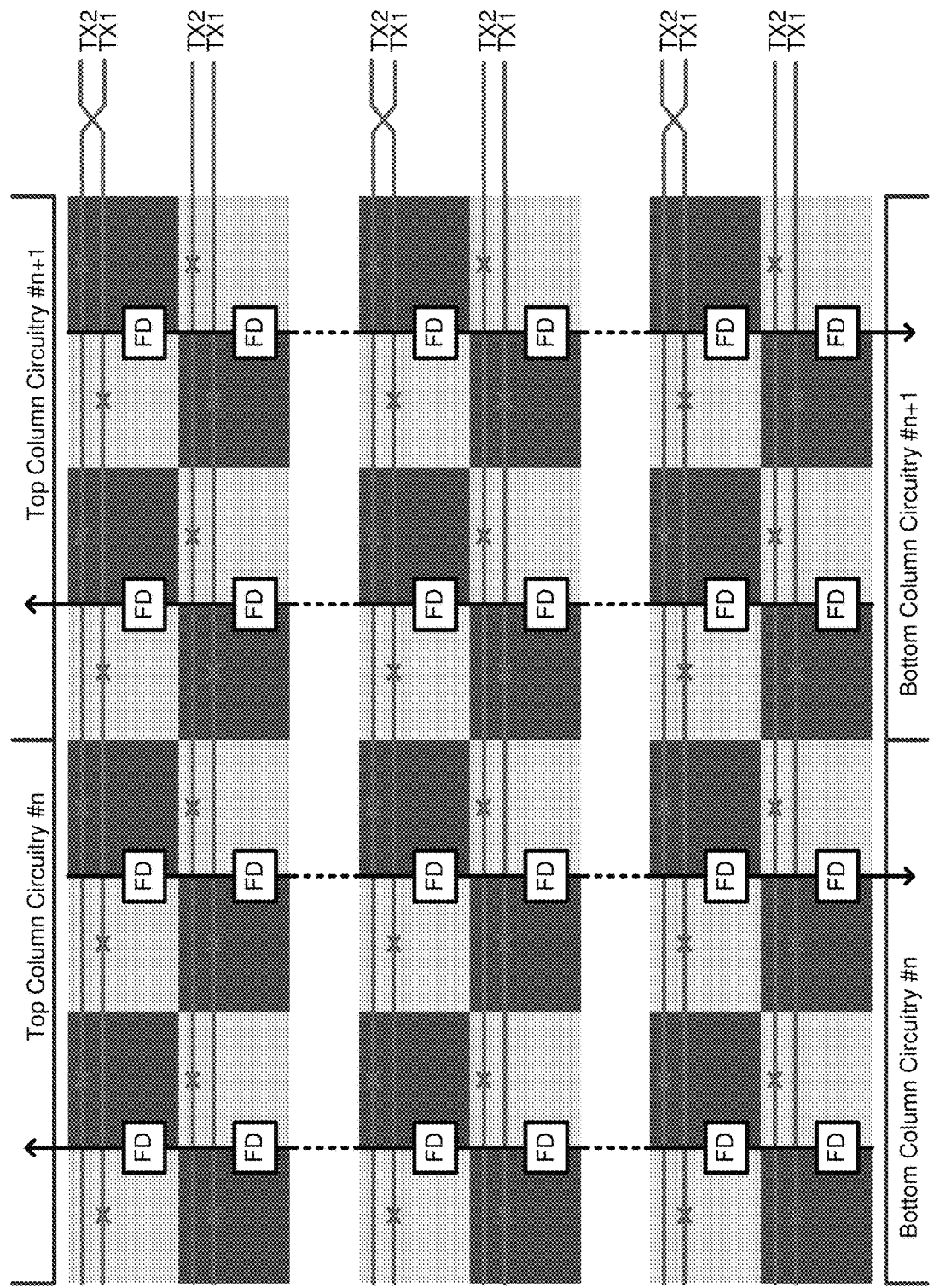
FIG. 15 is a graphical representation of a single column circuit for a pixel array that may be used for vertical two-way sharing of pixels.

FIG. 15 illustrates a single column circuit that may serve four columns of pixels rather than two columns of pixels. The single column circuit may be used for vertical two-way sharing of pixels. The embodiment illustrated in FIG. 15 enables a checkerboard arrangement of dual exposures by switching the TX1 and TX2 odd/even column associations on alternate rows. This is accomplished by including a "twist" in the TX1/TX2 routing for every second row. This odd-even exposure pattern may be particularly applicable for monochrome image sensors as discussed herein.

In other embodiments, the switching of the TX1/TX2 assignments from row to row may be accomplished by virtue of two alternating flavors of row driver circuitry at the side of the array, or by crafting the TX1/TX2 routing differently within the odd and even rows.

Figure 16A:
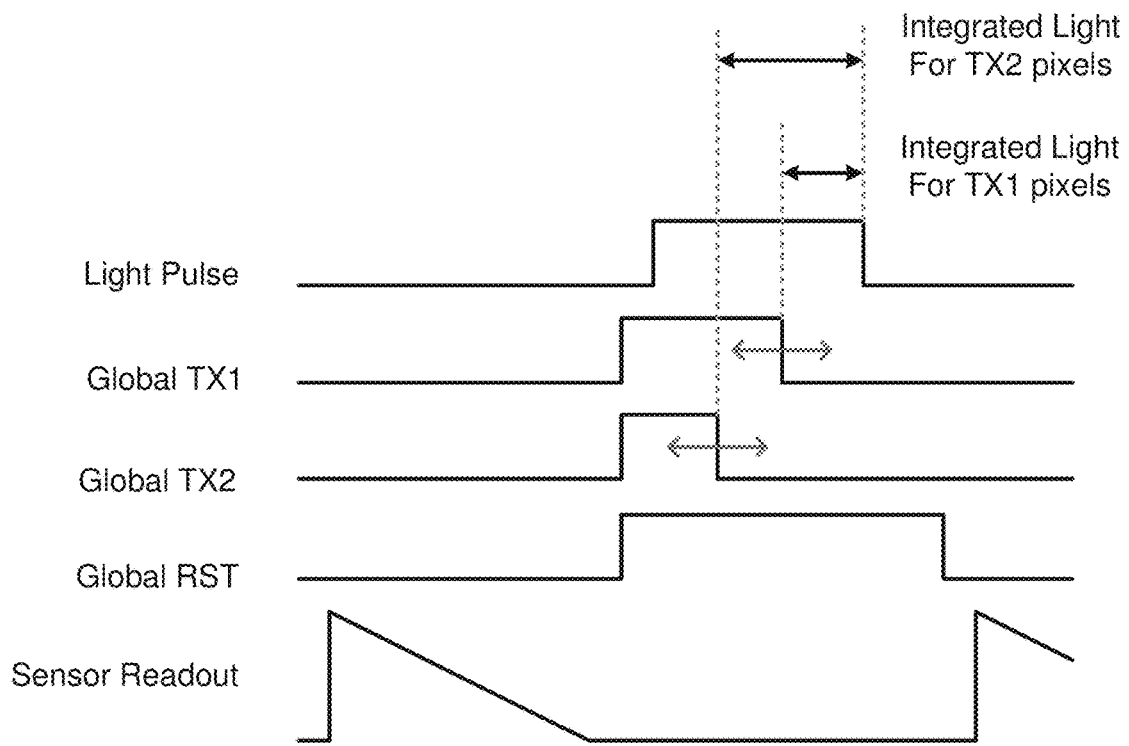
FIG. 16A is a timing diagram for a pixel array in which all pixels are held in reset mode when GlobalTX1, GlobalTX2, and GlobalRST are high.
Figure 16B:
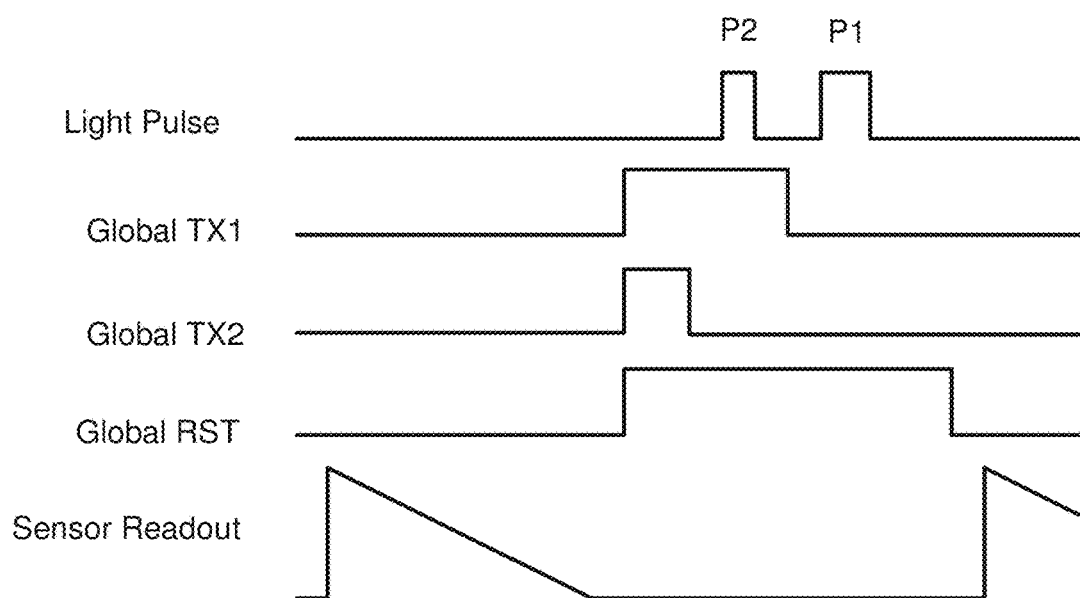
FIG. 16B is a timing diagram for a pixel array in a dual illumination environment.

FIGS. 16A and 16B illustrate timing for two alternative ways in which multiple sets of pixels in an array may integrate different degrees of light. The exposure modulation may be affected by virtue of two global TX pulses, GlobalTX1 and GlobalTX2. The two global TX pulses effectively create two global shutters when combined with the light pulse edge(s). At the end of the integration period, the rolling pointer provides another TX pulse in order to transfer the signal for readout. For descriptive purposes, the case of two sets of pixels of different exposures in the checkerboard pattern (see e.g., FIGS. 8-11 and 15), will mainly be emphasized. It should be noted however, that the scope of this disclosure is intended to cover cases with higher numbers of pixel types (i.e., exposures) and with alternative physical pixel type arrangements. The spatial pattern depends on the number of pixel sets, the pixel layout, the pixel array arrangement and the pixel array connections to the peripheral circuitry.

To avoid confusion, the rolling TX signals may be referred to herein as TX1 and TX2, whereas the global TX signals may be called GlobalTX1 and GlobalTX2. Global pulses affect all attached pixels in the array at the same time. The non-global pulses may be applied via the rolling pointer.

Now referring to FIG. 16A, all pixels may be held in reset mode (and may therefore be flushed) when GlobalTX1, GlobalTX2 and GlobalRST are high. When GlobalTX2 is low, all pixels in the array attached to TX2 begin to integrate. When the P2 light pulse occurs, the corresponding photo charge is integrated by the TX2 pixels. However, because the GlobalRST and GlobalTX1 signals may still be high, any photo charge created by the P2 pulse in the TX1 pixels may be drained off. When GlobalTX1 is low, the TX1 pixels begin to integrate. At that point, the TX2 pixels will have fully integrated the P2 pulse and the TX1 pixels will not have integrated. When the P1 light pulse occurs, it may be integrated by both the TX1 and the TX2 pixels. Therefore, at the end of the sequence, the TX1 pixels will have a net photo charge resulting from only the P1 light pulses whereas the TX2 pixels will have integrated both light pulses.

FIG. 16B is a similar timing diagram for an alternative dual illumination embodiment. In the embodiment illustrated in FIG. 16B, a single light pulse is emitted during the period both TX transistors are turned off. The integrated light may be proportional to the time between the TX falling edge and the light pulse falling edge. Therefore, different pixel responses may be achieved by staggering the GlobalTX1 and GlobalTX2 falling edges. In the example illustrated in FIG. 16B, the TX1 pixels integrate ~⅓ of the light generated by the light pulse and the TX2 pixels integrate ~⅔ of the total pulse energy.

In a further embodiment, dual illumination can be achieved by employing a mixture of the timing embodiments illustrated in FIGS. 16A and 16B. The GlobalTX2 signal would return to its low state before the rising edge of the single light pulse. This causes the TX2 pixels to integrate the whole energy of the light pulse.

Figure 17:
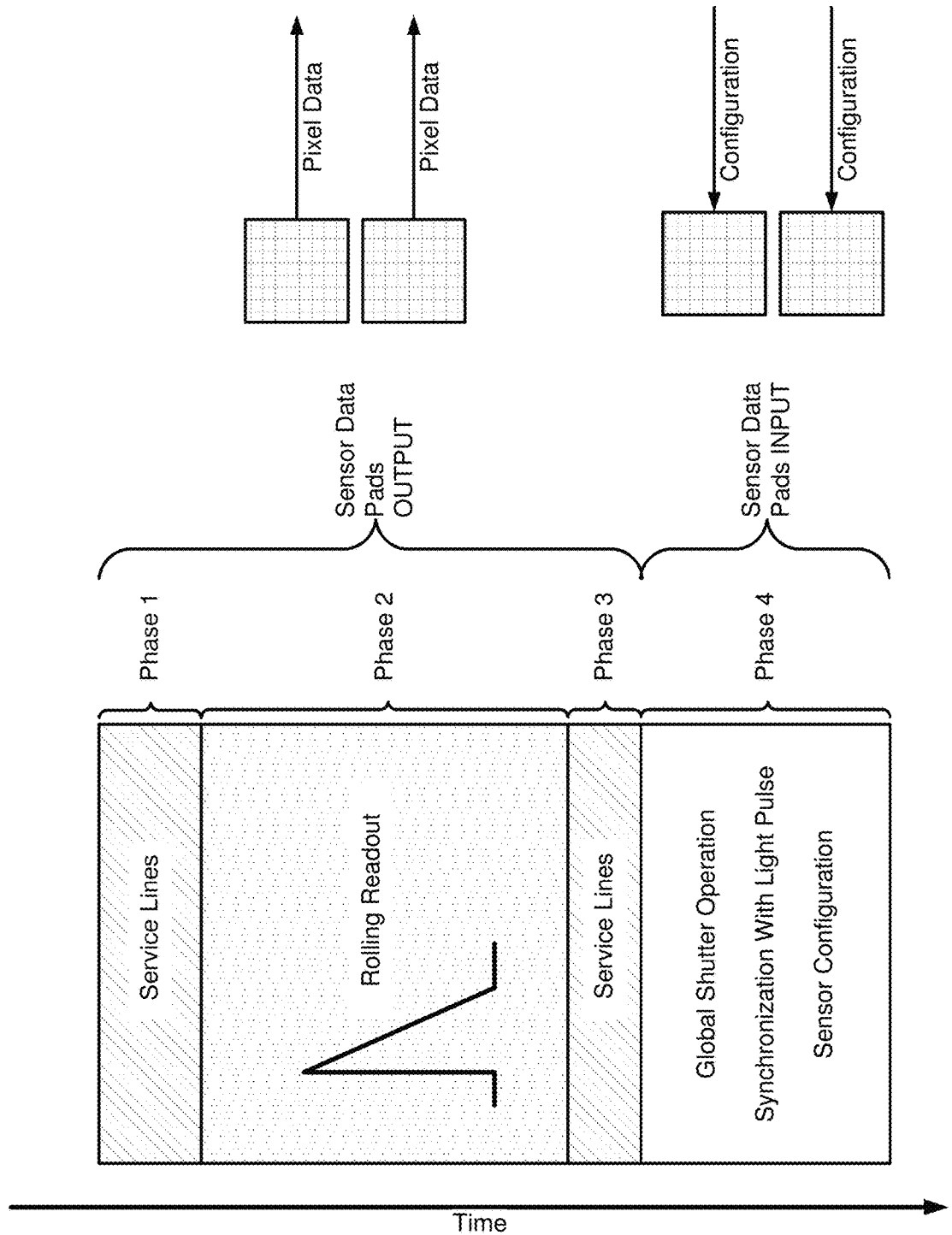
FIG. 17 is an internal timing diagram of a minimal area custom image sensor that may be implemented for endoscopic imaging in the presence of controlled, pulsed illumination.

FIG. 17 illustrates the internal timing of an embodiment of a minimal area custom image sensor. The timing may be implemented for the purpose of endoscopic imaging in the presence of controlled, pulsed illumination. Each frame period may comprise four distinct phases, which may be optimized for monochrome light pulsing and multiple pixel illuminations.

During phase 1 and phase 3, data may be issued from the image sensor. The data issued from the image sensor may not be signal samples from physical pixels but instead may be data concerned with the synchronization of the chip to the camera system and for data locking. These "service line" periods may also be used for internal monitoring and external monitoring, and further for encoding certain types of non-pixel data within the line. Internal monitoring may include the sensor temperature, certain voltages, currents, and so forth. External monitoring may include hand-piece button activity or, e.g., data from measurements of the angle of the endoscope. Phase 2 may be concerned with the sensor rolling readout (internal timing and synchronization) while phase 4 may be for the purpose of sensor configuration. During the configuration phase, the sensor output data lines may be reversed to accept incoming configuration commands. Therefore, the camera controller may be synchronized to the phase 4 period. Phase 4 also doubles as the global shutter phase. For this reason, phase 4 may be also synchronized with the light pulsing system.

Note that the pulse widths and timing of the global signals (GlobalTX1, GlobalTX2 and GlobalRST) may be fully programmable such that phase 4 is the only phase with variable length. This enables the available pulse time to be tuned in order to match the available light power, given the type of frame it is. Individual wavelength sources may vary significantly with respect to maximum available light power, quantum efficiency, response time, and so forth.

Figure 18:
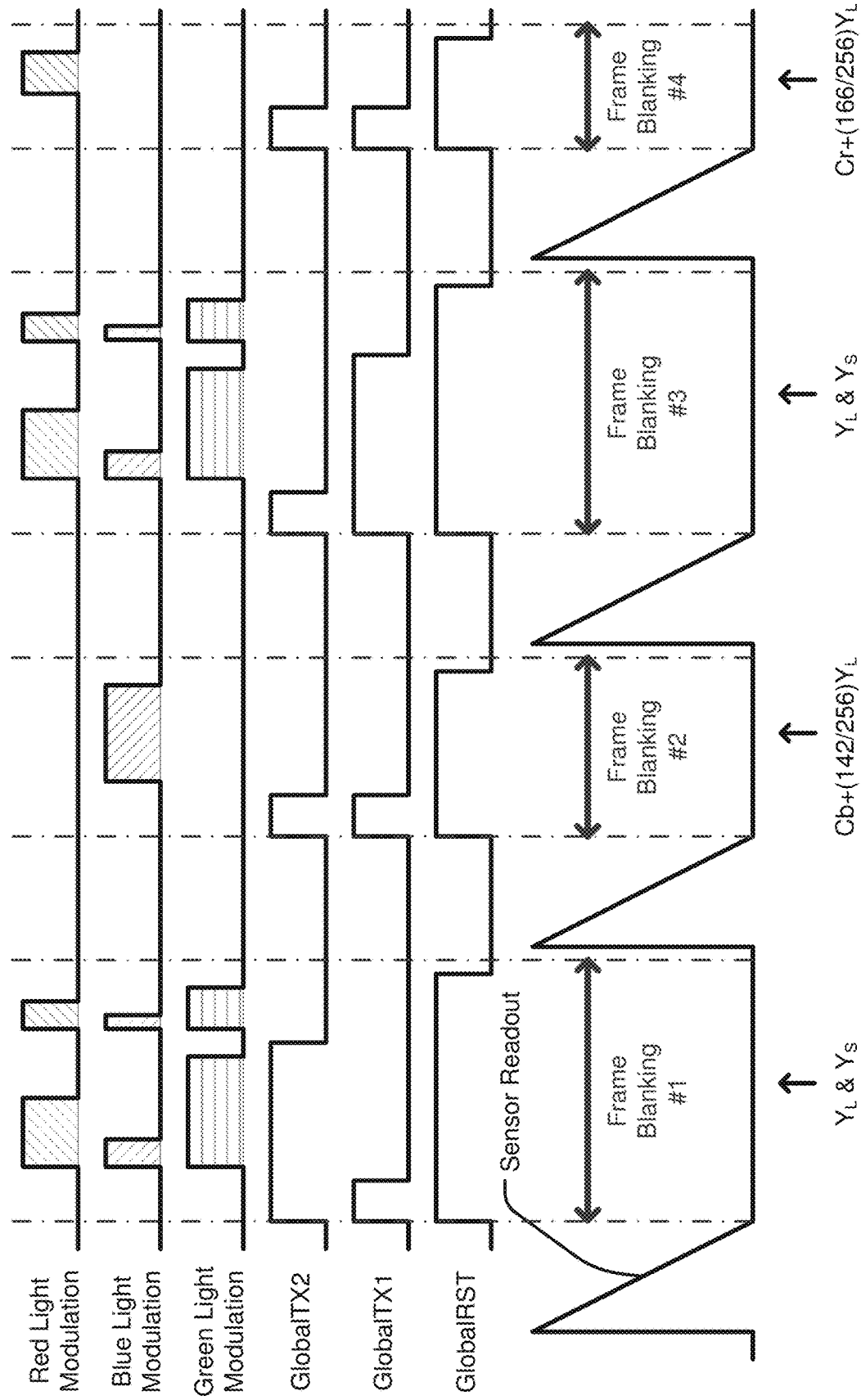
FIG. 18 is a timing diagram for a frame sequence of an image sensor that may be applied for the exposure frame sequence illustrated in FIG. 9 for generating a YCbCr image frame.

FIG. 18 illustrates a timing diagram for a frame sequence. The timing diagram may be applied for the exposure frame sequence illustrated in FIG. 9 and is based on a Y-Cb-Y-Cr (luminance, chrominance blue, luminance, chrominance red) pulsing pattern. Y is the luminance component, Cb is the blue-difference chrominance component, and Cr is the red-difference chrominance component. In an embodiment, all light sources may be pulsed during the luminance frames (the first exposure frame 902 and the third exposure frame 906). The second exposure frame 904 and the fourth exposure frame 908 are sensed in response to a single wavelength pulse of a critically tuned admixture of luminance.

The frame sequence may further include pulsing for one or more of a hyperspectral exposure frame, a fluorescence exposure frame, and/or a laser mapping exposure frame. In an embodiment, a YCbCr image frame is generated based on the pulsing scheme illustrated in FIG. 18, and one or more of a hyperspectral exposure frame, a fluorescence exposure frame and/or laser mapping data is overlaid on the YCbCr image frame. It should be appreciated that the additional exposure frame data may alternatively be overlaid on an RGB image frame. Alternatively, the YCbCr image frame may be combined with one or more of the hyperspectral exposure frame or the fluorescence exposure frame such that a single image frame includes luminance data, chrominance data, and one or more of hyperspectral data and fluorescence data.

Figure 19:
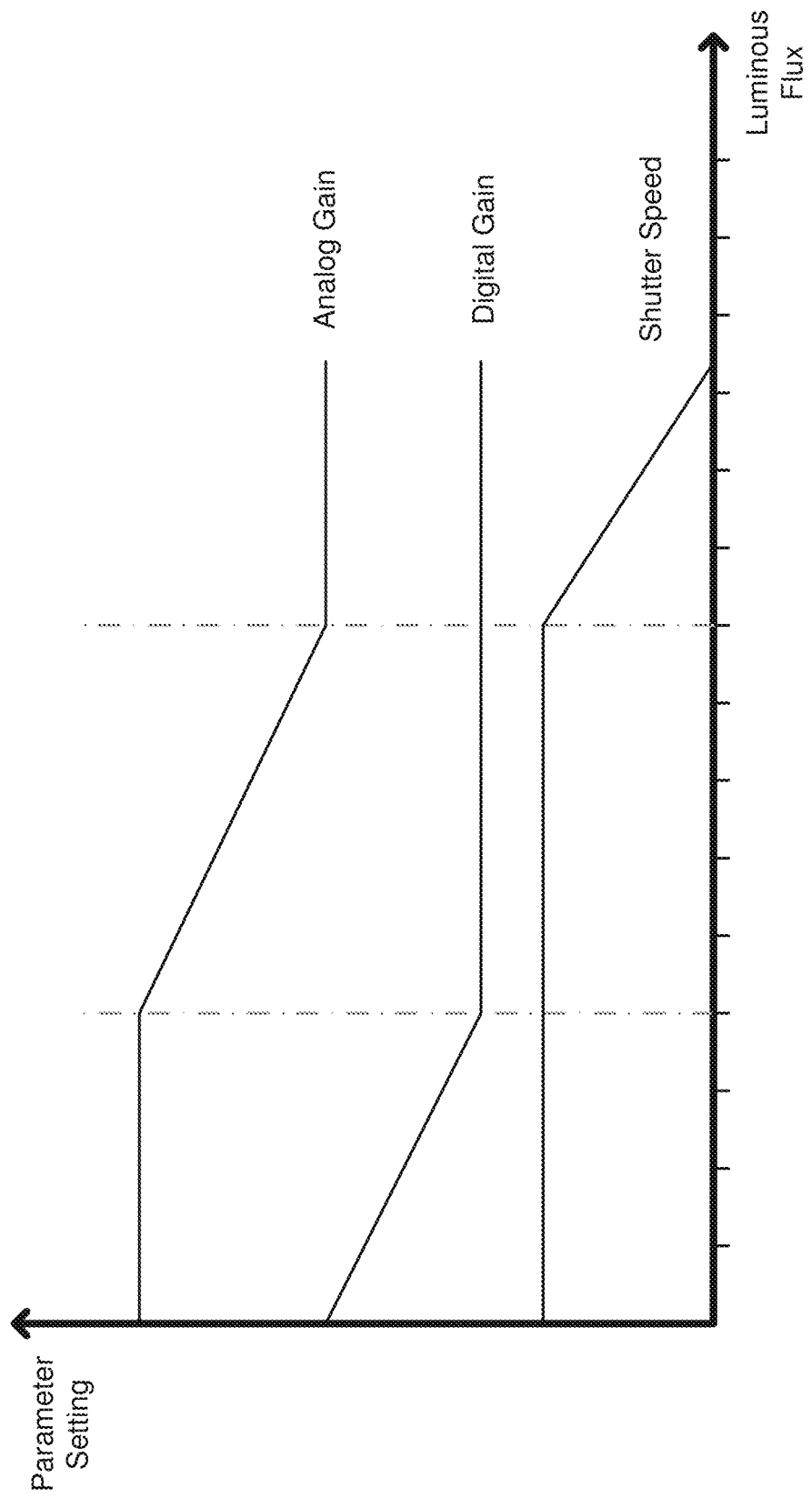
FIG. 19 is a line graph illustrating an example system that incorporates analog gain, digital gain, and shutter time into determining autoexposure for adjusting to an illumination scenario.

FIG. 19 is a line graph illustrating an example system that incorporates analog gain, digital gain, and shutter time into determining autoexposure for adjusting to an illumination scenario. Generally, digital cameras that experience randomly varying illumination scenarios incorporate a means of continually adjusting image sensor configurations to ensure the best use of available dynamic range. This process is referred to as autoexposure, and the example system illustrated in FIG. 19 determines autoexposure configurations based on analog gain, digital gain, and shutter speed.

The autoexposure line graph illustrated in FIG. 19 may be applied to video cameras and still cameras deployed in a varying illumination environment. Alternatively, the systems disclosed herein may be deployed in a light deficient environment in which the imaging system has full control over illumination of a scene. The imaging system may have complete control over the amount of pulsed red, pulsed green, pulsed blue, and pulsed laser mapping illumination. The pulsed illumination may be altered for each exposure frame for continuous video capture. The overall light pulse energy emitted by the imaging system may take the place of the shutter speed in terms of determining how much light energy is sensed by the image sensor.

Because more photo signal results in higher signal to noise ratio, the light energy may be increased until the desired digital signal level is reached within the Image Signal Processor (ISP). The analog gain may be held at its minimum setting which can be considered to be the gain at which the bottom of the distribution of pixel signal capacity is above the upper rail of the analog to digital converter. The maximum light pulse energy may be limited by the duration of the available portion of the exposure frame and by the maximum electromagnetic energy provided. For the R-G-B-G pulse sequence case, the best overall signal to noise ratio may be obtained by monitoring and controlling the three frame types independently and attenuating two of the colors digitally in the ISP for white balance purposes.

Figure 20:
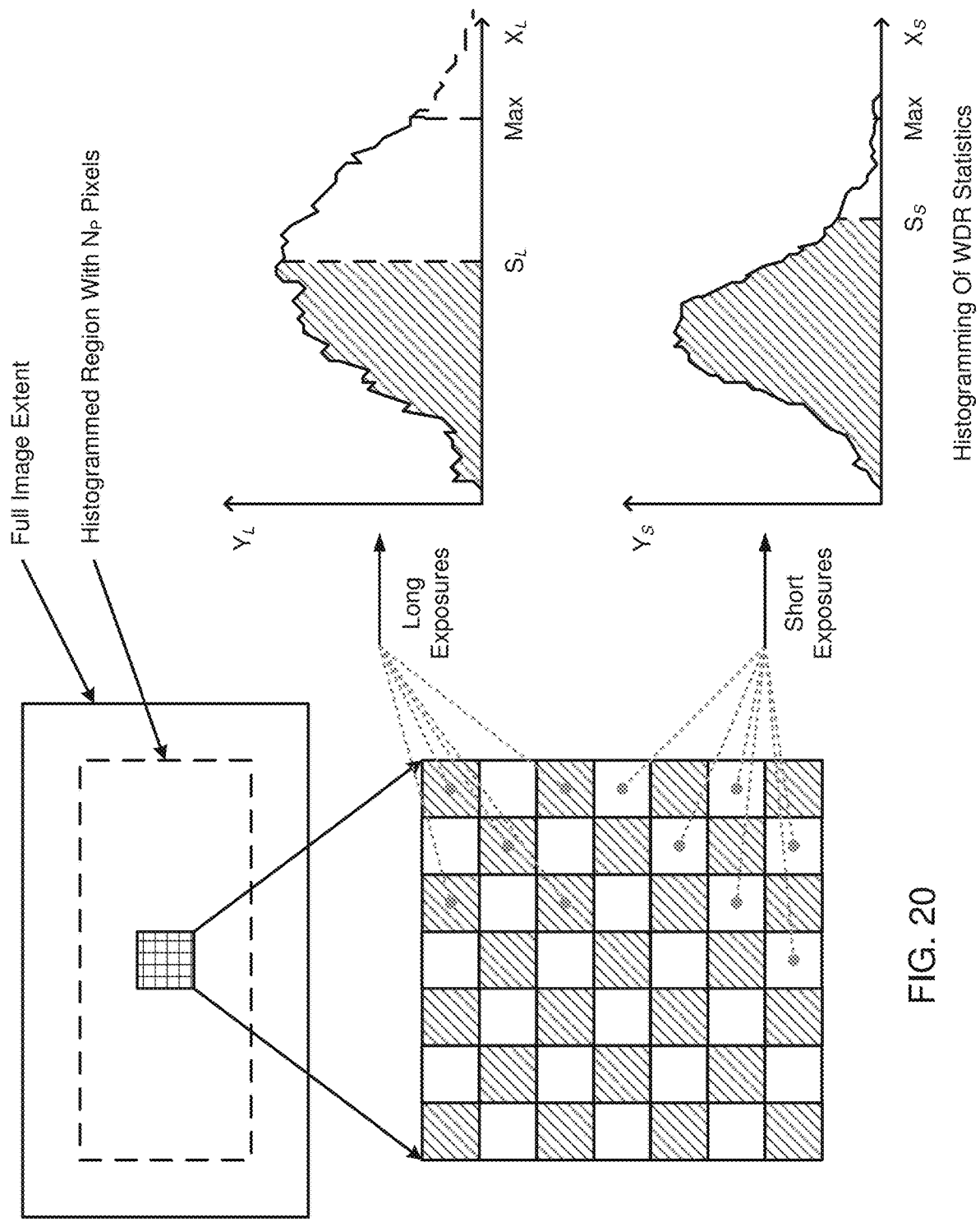
FIG. 20 is a schematic diagram illustrating how statistics for wide dynamic range may be gathered independently for short exposure pixels and for long exposure pixels.

FIG. 20 is a schematic diagram illustrating how statistics for wide dynamic range (WDR) may be gathered independently for short exposure pixels and for long exposure pixels of a pixel array. The WDR statistics may captured and analyzed independently for red, green, blue, and laser mapping exposure frames.

FIG. 20 illustrates two corresponding histograms of black-corrected signal for a region of an exposure frame. One of the histograms may be used, as mentioned earlier, to control the pulse energy level by comparing a chosen percentile ($P_L$) of the distribution to a target signal level ($S_L$, e.g. 50% of the digital dynamic range). The exposure time of these type-1 pixels, $T_L$, may be held at maximum. The subscript L here denotes the long exposure. The other histogram may be used to monitor the dynamic range of the scene by comparing another chosen percentile of the distribution, $P_S$, where $P_S > P_L$, and comparing that with a different signal level, $S_S$, where $S_S > S_L$. The subscript S denotes the short exposure. $S_S$ may be generally tuned close to the top of the digital dynamic range. If $P_S \leq S_S$, the exposure time for these type-2 pixels, $T_S$, may be also held at maximum. If $P_S > S_S$, then $T_S$ may be lowered until $P_S = S_S$. There may be a predefined limit (E) as to how much the exposure time ratio may be allowed to increase to ensure that image quality degradation due to dynamic range enhancement outweighs the benefit of enhancing the dynamic range. The values of $P_L$, $P_S$, $S_L$, $S_S$ and E may be tuned differently according to different applications and stored as factory presets. The exposure times $T_L$ and $T_S$ may be recorded for each exposure frame type, for use by the wide dynamic range fusion process and by the color fusion ISP stage. In the case that the red, green, blue, and laser mapping pulse energies are modulated for the purpose of white balance, the exposure times on the red and blue frames may be governed by the green frames which may be exclusively used to gather the wide dynamic range statistics.

In an implementation in which the imaging system is pulsing for luminance and chrominance illumination to generate a YCbCr image frame, the relative pulse energies may be held constant for a particular type of exposure frame. The wide dynamic range control may be applied for the luminance frames as a baseline with the option of also applying wide dynamic range independently on the chrominance frames. The histograms may be constructed on the raw black-corrected frame data as for the R-G-B-G scheme. Again, the exposure times for each frame type may be recorded for wide dynamic range fusion and for color fusion.

Figure 21:
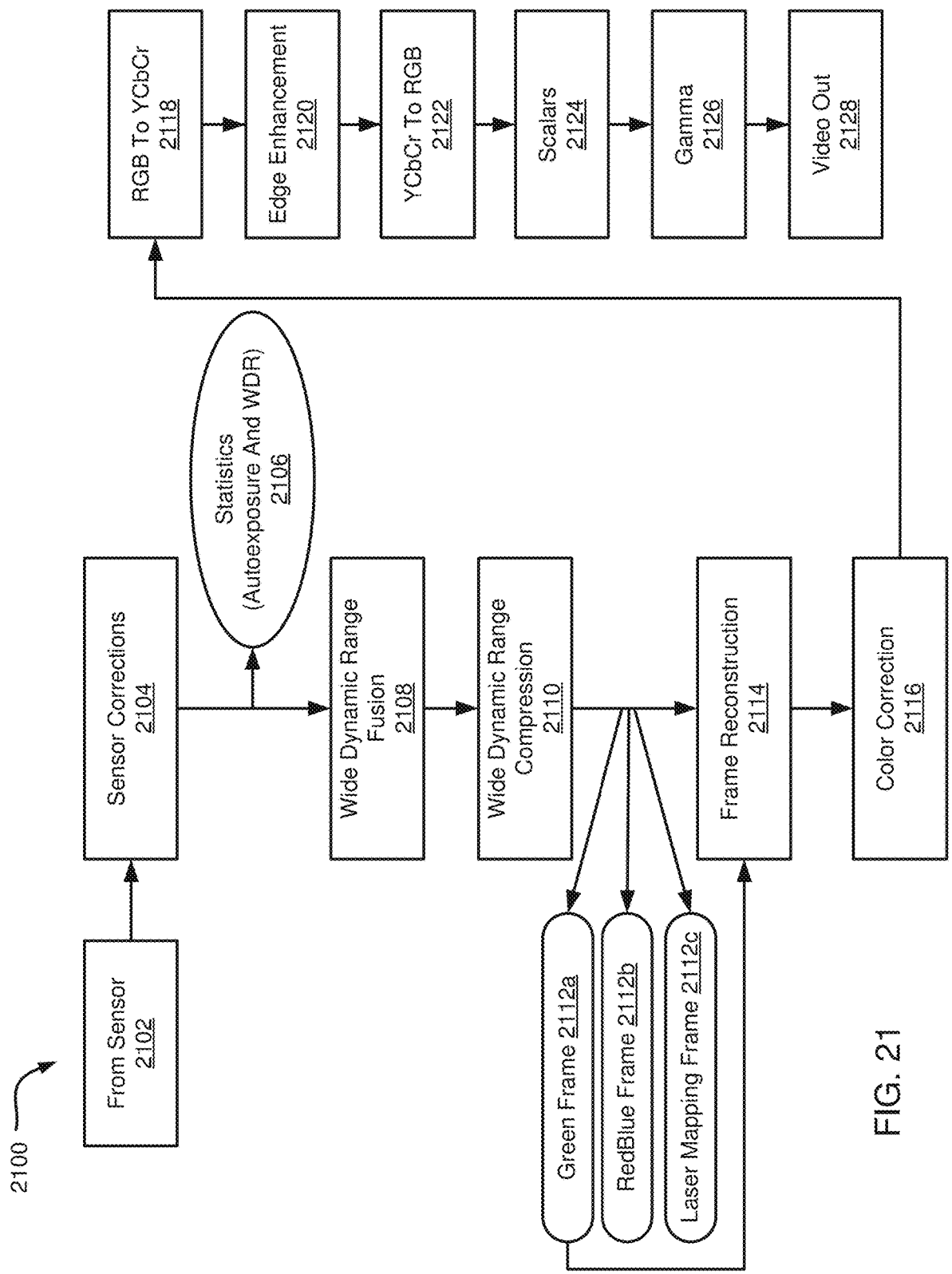
FIG. 21 is a schematic diagram of a process flow to be implemented by a controller or image signal processor for generating a video stream with RGB image frames and laser mapping data overlaid on the RGB image frame.

FIG. 21 is a schematic diagram of a process flow 2100 to be implemented by a controller and/or monochrome image signal processor (ISP) for generating a video stream having RGB images with laser mapping data overlaid thereon. The process flow 2100 results in images having increased dynamic range. The image signal processor (ISP) chain may be assembled for the purpose of generating sRGB image sequences from raw sensor data, yielded in the presence of the G-R-G-B-Laser Mapping light pulsing scheme. In the process flow 2100, the first stage is concerned with making corrections to account for any non-idealities in the sensor technology for which it is most appropriate to work in the raw data domain. At the next stage, multiple frames (for example, a green frame 2112a, a red-blue frame 2112b, and a laser mapping frame 2112c) are buffered because each final frame derives data from multiple raw frames. The frame reconstruction at 2114 proceeds by sampling data from a current frame and buffered frames (see 2112a, 2112b, and/or 2112c). The reconstruction process results in full color frames in linear RGB color space that includes laser mapping image data.

In an embodiment, the process flow 2100 is applied to checkerboard readings from a pixel array (see FIGS. 8-11). The checkerboard readings may be sensed in response to an R-G-B-G-Laser Mapping or Y-Cb-Y-Cr-Laser Mapping pulsing scheme. The process flow 2100 includes receiving data from an image sensor at 2102. Sensor correction calculations are performed at 2104. These sensor correction calculations can be used to determine statistics at 2106 such as autoexposure settings and wide dynamic range settings. The process flow 2100 continues and wide dynamic range fusion is processed at 2108. Wide dynamic range compression is processed at 2110. The wide dynamic range compression from 2110 can be fed to generate a green frame 2112a, a red-blue frame 2112, and/or a laser mapping frame 2112c. The process flow 2100 continues and frame reconstruction is processed at 2114 and then color correction is processed at 2116. The process flow 2100 continues and an RGB (red-green-blue) image is converted to a YCbCr image at 2118. Edge enhancement is processed at 2120 and then the YCbCr image is converted back to an RGB image at 2122. Scalars are processed at 2124 and gamma is processed at 2126. The video is then exported at 2128.

In an embodiment, the wide dynamic range fusion at 2108 is executed after dark frame subtraction such that the mean black offset has been adjusted to zero. In an embodiment, the aim of the wide dynamic range fusion 2108 is to combine data from two or more separate exposure frames into a single image frame prior to color fusion. This may be accomplished by separating the short exposure and long exposure components of the checkerboard pattern into separate buffers and filling in the gaps by interpolation. There may be only one general kernel required because every empty pixel sees the same local environment except for pixels near the edges of the image. A suitable convolution kernel for filling in the checkerboard pattern by simple linear interpolation is:

$$\begin{pmatrix} 0 & \frac{1}{4} & 0 \\ \frac{1}{4} & 0 & \frac{1}{4} \\ 0 & \frac{1}{4} & 0 \end{pmatrix}$$

Figure 22:
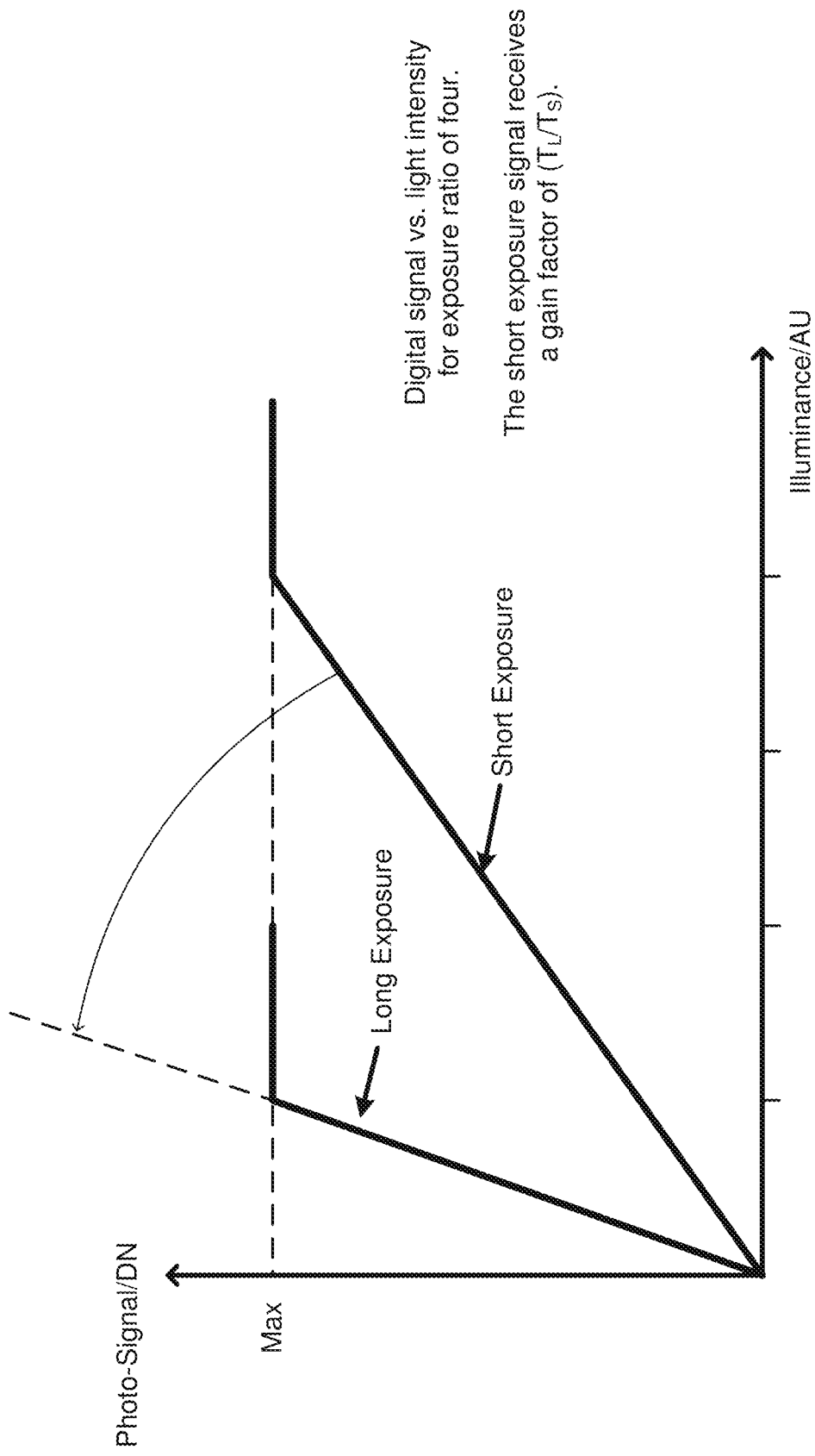
FIG. 22 is a line graph illustrating the illuminance-signal relationships for an exposure ration of four that yields greater dynamic range.
Figure 23:
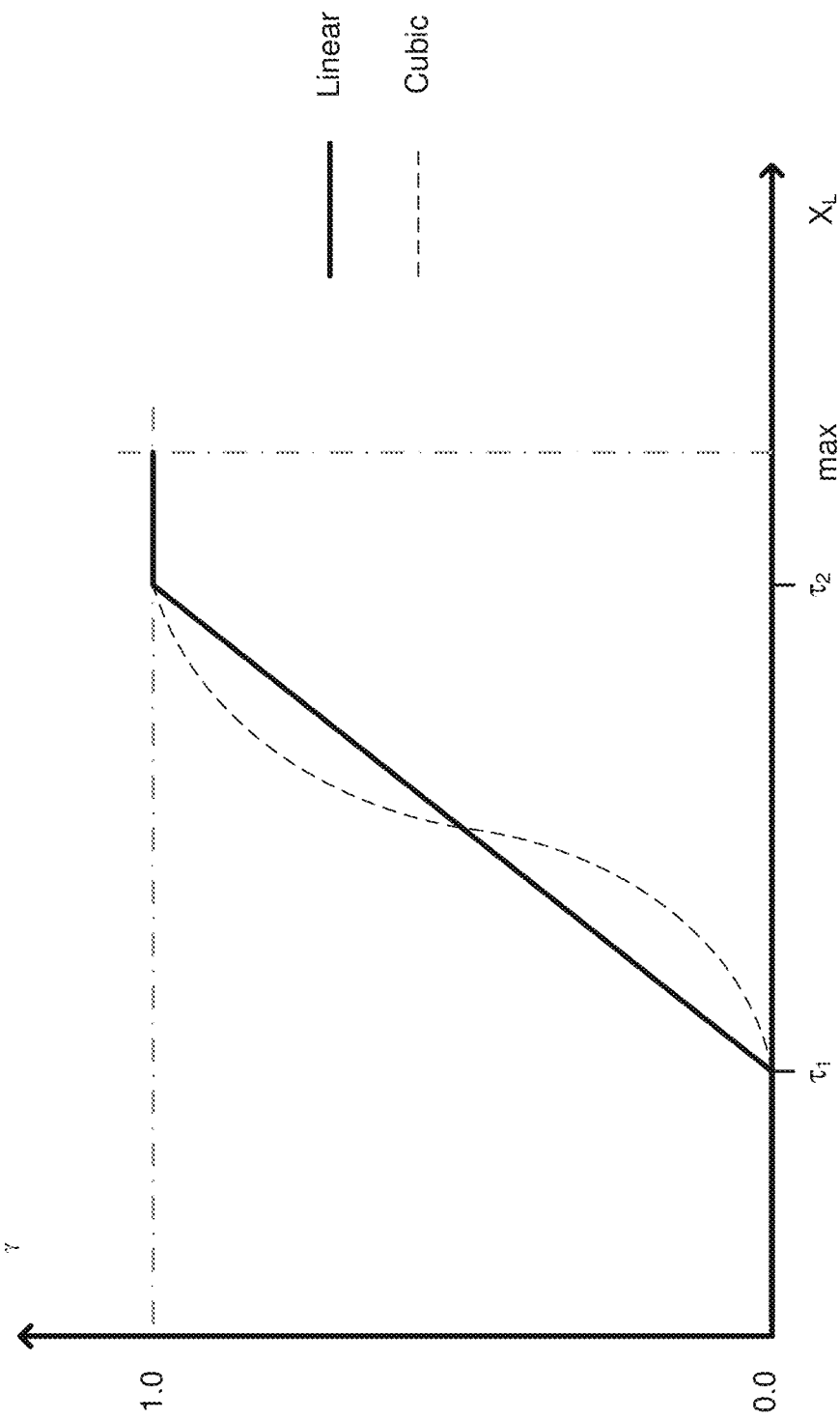
FIG. 23 is a line graph illustrating the dependence of fusion weighting on long exposure signal for an image sensor.

Following interpolation there may be two samples for each pixel location. FIG. 22 is a line graph illustrating the illuminance-signal relationships for an exposure ratio of four that yields 12 dB of additional dynamic range. A gain may be applied to the short exposure sample which may be equal to the exposure-time ratio, $T_L/T_S$. This requires the addition of one extra bit for each factor two of ratio. The fusion itself involves making a weighted sum of the two samples as follows:

$$x_f = \gamma \cdot \left(\frac{T_L}{T_S}\right) \cdot x_s + (1-\gamma)x_L$$

Where $x_S$ and $x_L$ may be the short exposure signals and the long exposure signals, respectively. The $\gamma$ factor may be a function of the long exposure signal, $x_L$, and may be set according to two thresholds, $\tau_1$ and $\tau_2$. Below $x_L$, $=\tau_1$, $\gamma=0.0$, above $\gamma=\tau_2$, $\gamma=1.0$. Between the thresholds, various functional forms may be employed. See FIG. 23 in which linear and cubic example behaviors of $\gamma$ between $\tau_1$ and $\tau_2$, may be drawn. The value of $\tau_2$ may be set to the maximum possible value of $x_L$ or something just below it. The purpose of the lower threshold, $\tau_1$, is to limit the influence of read noise from the short sample which has the gain factor $T_L/T_S$ applied. It can be set to a conservatively high constant to accommodate the maximum ratio E, but it may be more beneficial to have it vary linearly with $T_L/T_S$ as follows:

$$\tau_1 = \left(\frac{T_L}{T_S}\right) \cdot \eta$$

Figure 24:
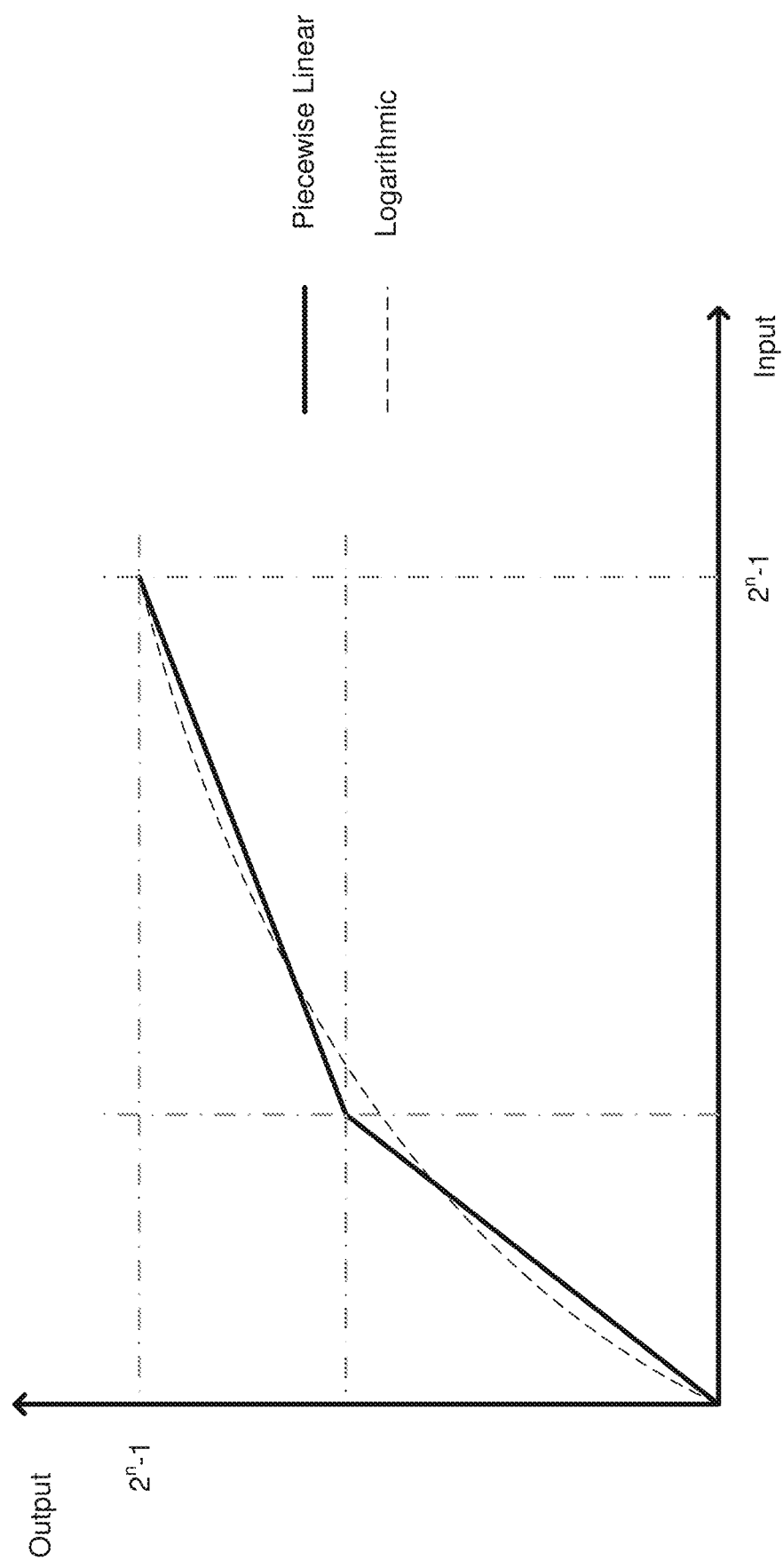
FIG. 24 is a line graph illustrating the transfer function for data compression for a piece-wise linear transfer function.

Following the stitching process, the image data occupies a greater number of bits of digital dynamic range than the original long exposure and short exposure samples. Therefore, the bit count of the image sensor needs to reduced back to the ISP pipeline width prior to the next stage. If the ISP pipeline width is n bits, the fused image has m bits where (m−n) is the base-2 logarithm of the exposure time ratio rounded up to the next integer. The data may be first linearly scaled such that the maximum possible value maps to exactly $2^m-1$. This can be accomplished by provision of a lookup table of multipliers for the set of allowed exposure time ratios that lie between one and two to get to the next exact power of two. This approach assumes the progression of allowed exposure time ratios within each power of 2-interval is consistent. To return to n bits, a piece-wise linear transfer function may be applied which emphasizes the data at the low end. This is illustrated in FIG. 24. This prevents interesting information at the low end being lost through compression. Alternatively, a smooth logarithmic transfer function can be applied to the data using a predefined lookup table. In this embodiment, the lookup table needs to have sufficient entries to cover the maximum fused linear bit count ($m_{max}$). The fused data, already scaled to an exact power of two is further up-shifted to $m_{max}$ bits before applying the LUT.

Figure 25:
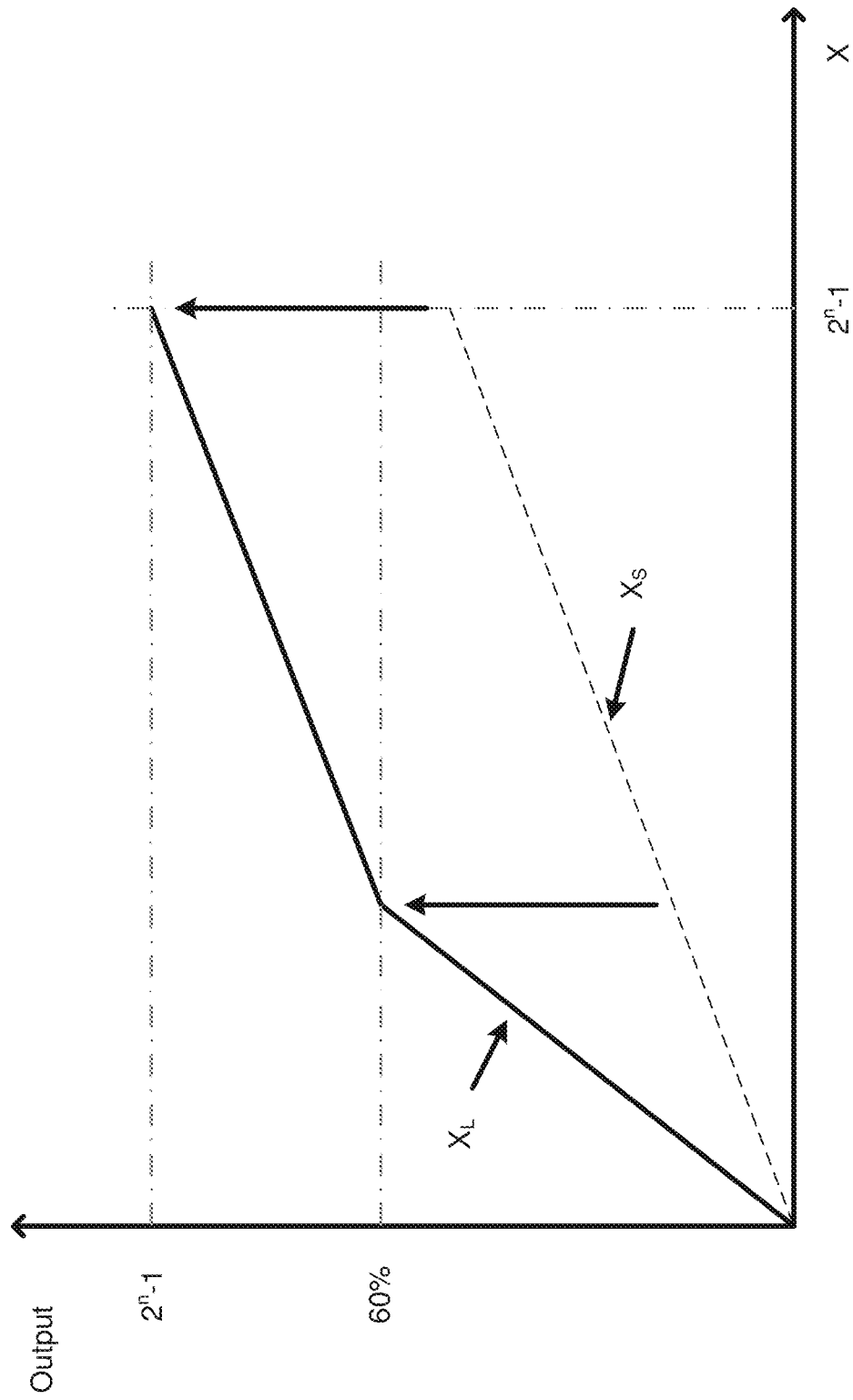
FIG. 25 is a line graph illustrating the simple stitching approach in which sections are mapped to long exposure samples and short exposure samples and crossover occurs at the maximum of $x_L$.

A simpler embodiment for fusion and compression is to divide the final dynamic range into two sections. Example sections may include the bottom 60% and the top 40%. The two sections are mapped to the long exposure samples and the short exposure samples respectively. In the input domain, the crossover occurs at the maximum value of $x_L$. This is illustrated in FIG. 25.

The provision of two or more exposure periods within the same frame within a pulsed illumination endoscopy system may be exploited for the purpose of reducing the number of captured frames per final full color image from three to two. This enables the benefit of suppressing color motion artifacts associated with the imaging system.

One property of the monochrome wide dynamic range pixel array is that pixels with a long integration time may integrate a superset of the light seen by the short integration time pixels. For regular wide dynamic range operation in the luminance frames, this may be desirable. For the chrominance frames it means that the pulsing may be controlled in conjunction with the exposure periods so as to provide $\lambda Y+Cb$ from the start of the long exposure and switch to $\delta Y+Cr$ at the point that the short pixels may be turned on. $\lambda$ and $\delta$ may be two tunable factors that may be used to bring all pulse energies to positive values.

During color reconstruction in the ISP, the short exposure pixels and the long exposure pixels may be separated into two buffers. The empty pixels may be filled in using linear interpolation. At this point, one buffer includes a full image of $\delta Y+Cr$ data and another buffer includes $\delta Y+Cr+\lambda Y+Cb$. The $\delta Y+Cr$ buffer may be subtracted from the $\delta Y+Cr+\lambda Y+Cb$ buffer to give $\lambda Y+Cb$. The appropriate proportion of luminance data from the Y frames may be subtracted out for each.

Figure 26:
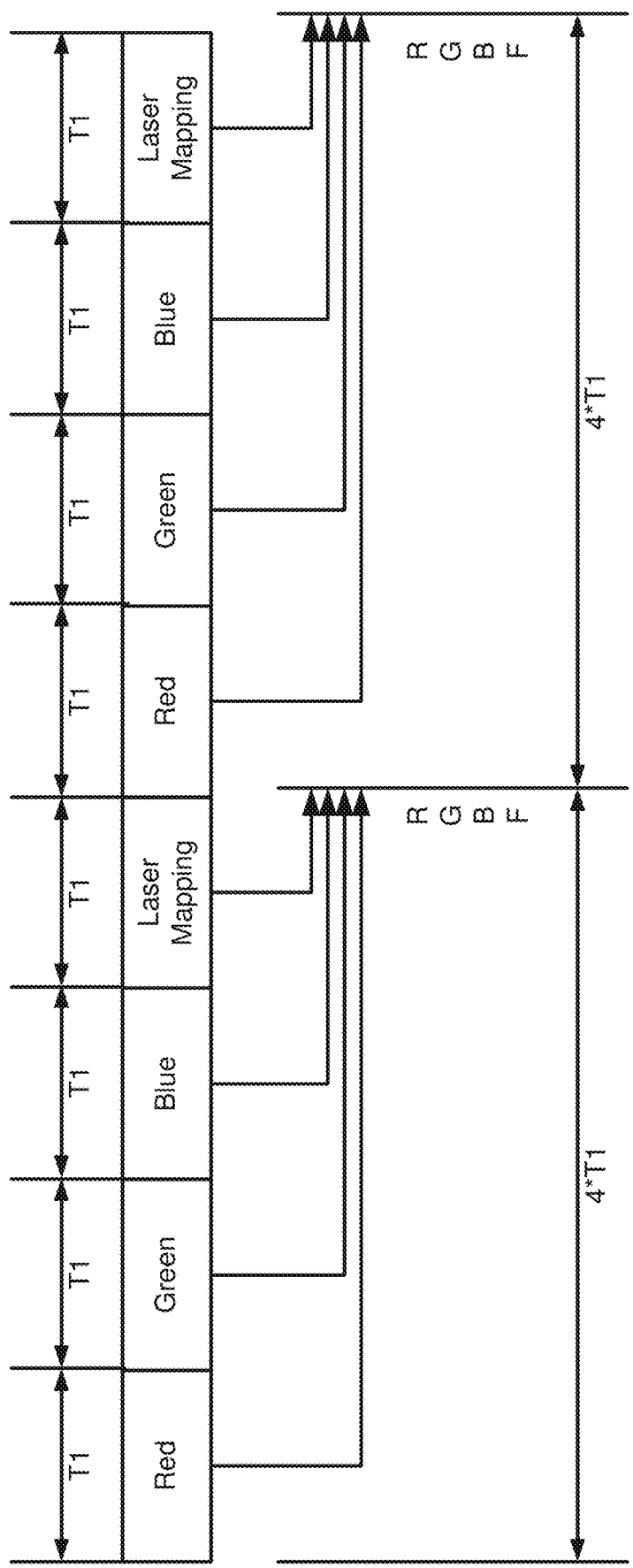
FIG. 26 is a schematic diagram of a pattern reconstruction process for generating an RGB image frame with laser mapping image data overlaid thereon.

FIG. 26 is a schematic diagram of a pattern reconstruction process. The example pattern illustrated in FIG. 26 includes Red, Green, Blue, and Laser Mapping pulses of light that each last a duration of T1. In various embodiments, the pulses of light may be of the same duration or of differing durations. The Red, Green, Blue, and Laser Mapping exposure frames are combined to generate an RGB image with laser mapping data overlaid thereon. A single image frame comprising a red exposure frame, a green exposure frame, a blue exposure frame, and a laser mapping exposure frame requires a time period of 4*T1 to be generated. The time durations shown in FIG. 26 are illustrative only and may vary for different implementations. In other embodiments, different pulsing schemes may be employed. For example, embodiments may be based on the timing of each color component or frame (T1) and the reconstructed frame having a period twice that of the incoming color frame (2×T1). Different frames within the sequence may have different frame periods and the average capture rate could be any multiple of the final frame rate.

In an embodiment, the dynamic range of the system is increased by varying the pixel sensitivities of pixels within the pixel array of the image sensor. Some pixels may sense reflected electromagnetic radiation at a first sensitivity level, other pixels may sense reflected electromagnetic radiation at a second sensitivity level, and so forth. The different pixel sensitivities may be combined to increase the dynamic range provided by the pixel configuration of the image sensor. In an embodiment, adjacent pixels are set at different sensitivities such that each cycle includes data produced by pixels that are more and less sensitive with respect to each other. The dynamic range is increased when a plurality of sensitivities are recorded in a single cycle of the pixel array. In an embodiment, wide dynamic range can be achieved by having multiple global TX, each TX firing only on a different set of pixels. For example, in global mode, a global TX1 signal is firing a set 1 of pixels, a global TX2 signal is firing a set 2 of pixel, a global TXn signal is firing a set n of pixels, and so forth.

Figure 27A:
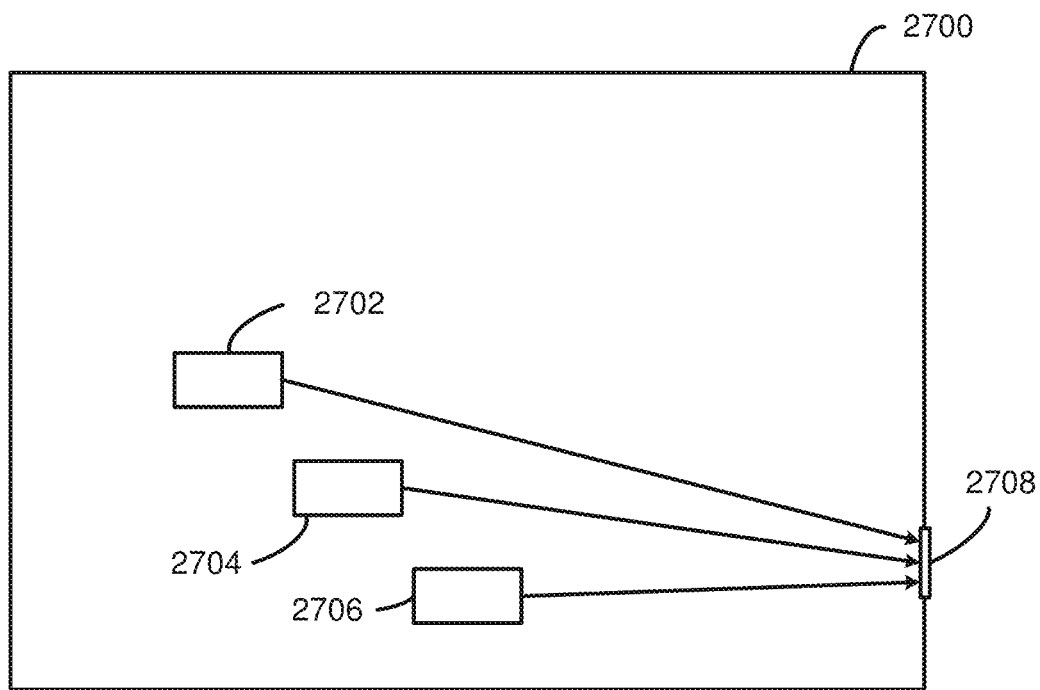
FIGS. 27A-27C illustrate a light source having a plurality of emitters.
Figure 27B:
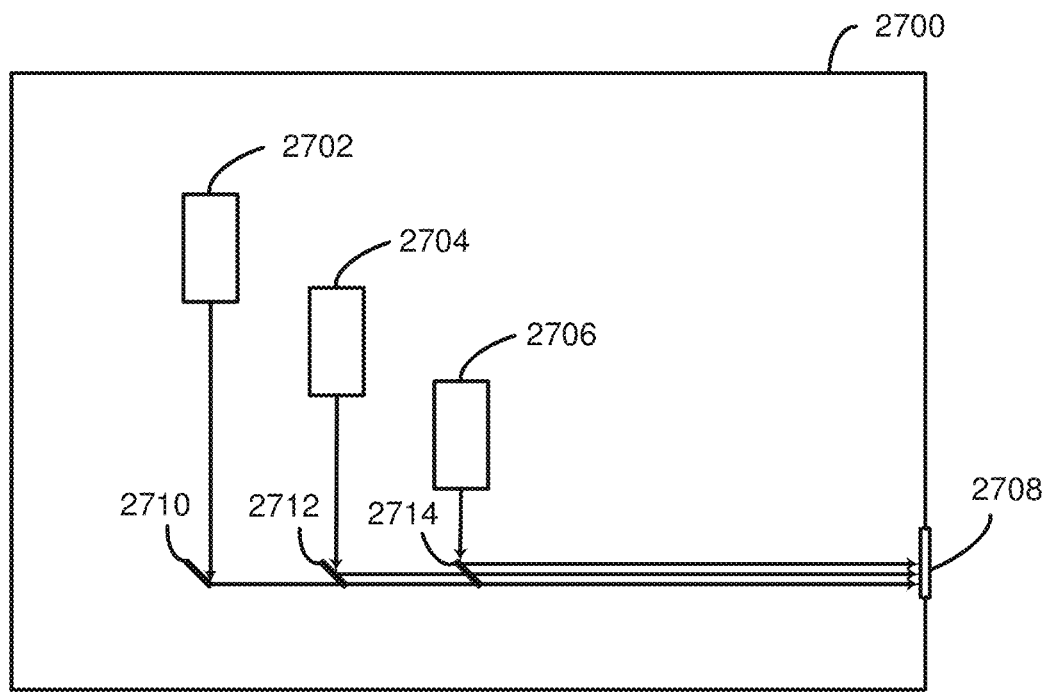
Figure 27C:
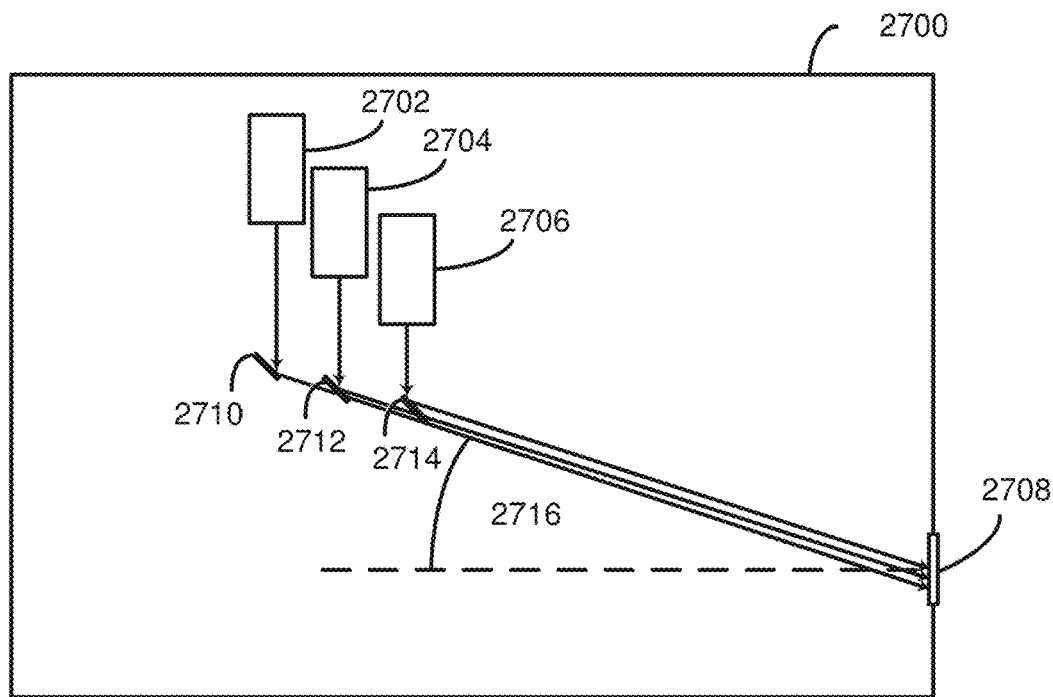

FIGS. 27A-27C each illustrate a light source 2700 having a plurality of emitters. The emitters include a first emitter 2702, a second emitter 2704, and a third emitter 2706. Additional emitters may be included, as discussed further below. The emitters 2702, 2704, and 2706 may include one or more laser emitters that emit light having different wavelengths. For example, the first emitter 2702 may emit a wavelength that is consistent with a blue laser, the second emitter 2704 may emit a wavelength that is consistent with a green laser, and the third emitter 2706 may emit a wavelength that is consistent with a red laser. For example, the first emitter 2702 may include one or more blue lasers, the second emitter 2704 may include one or more green lasers, and the third emitter 2706 may include one or more red lasers. The emitters 2702, 2704, 2706 emit laser beams toward a collection region 2708, which may be the location of a waveguide, lens, or other optical component for collecting and/or providing light to a waveguide, such as the jumper waveguide 206 or lumen waveguide 210 of FIG. 2.

In an implementation, the emitters 2702, 2704, and 2706 emit hyperspectral wavelengths of electromagnetic radiation. Certain hyperspectral wavelengths may pierce through tissue and enable a medical practitioner to "see through" tissues in the foreground to identify chemical processes, structures, compounds, biological processes, and so forth that are located behind the tissues in the foreground. The hyperspectral wavelengths may be specifically selected to identify a specific disease, tissue condition, biological process, chemical process, type of tissue, and so forth that is known to have a certain spectral response.

In an implementation where a patient has been administered a reagent or dye to aid in the identification of certain tissues, structures, chemical reactions, biological processes, and so forth, the emitters 2702, 2704, and 2706 may emit wavelength(s) for fluorescing the reagents or dyes. Such wavelength(s) may be determined based on the reagents or dyes administered to the patient. In such an embodiment, the emitters may need to be highly precise for emitting desired wavelength(s) to fluoresce or activate certain reagents or dyes.

In an implementation, the emitters 2702, 2704, and 2706 emit a laser mapping pattern for mapping a topology of a scene and/or for calculating dimensions and distances between objects in the scene. In an embodiment, the endoscopic imaging system is used in conjunction with multiple tools such as scalpels, retractors, forceps, and so forth. In such an embodiment, each of the emitters 2702, 2704, and 2706 may emit a laser mapping pattern such that a laser mapping pattern is projected on to each tool individually. In such an embodiment, the laser mapping data for each of the tools can be analyzed to identify distances between the tools and other objects in the scene.

In the embodiment of FIG. 27B, the emitters 2702, 2704, 2706 each deliver laser light to the collection region 2708 at different angles. The variation in angle can lead to variations where electromagnetic energy is located in an output waveguide. For example, if the light passes immediately into a fiber bundle (glass or plastic) at the collection region 2708, the varying angles may cause different amounts of light to enter different fibers. For example, the angle may result in intensity variations across the collection region 2708. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 2702, 2704, 2706 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 2708 is represented as a physical component in FIG. 27A, the collection region 2708 may simply be a region where light from the emitters 2702, 2704, and 2706 is delivered. In some cases, the collection region 2708 may include an optical component such as a diffuser, mixing rod, lens, or any other intervening optical component between the emitters 2702, 2704, 2706 and an output waveguide.

FIG. 27C illustrates an embodiment of a light source 2700 with emitters 2702, 2704, 2706 that provide light to the collection region 2708 at the same or substantially same angle. The light is provided at an angle substantially perpendicular to the collection region 2708. The light source 2700 includes a plurality of dichroic mirrors including a first dichroic mirror 2710, a second dichroic mirror 2712, and a third dichroic mirror 2714. The dichroic mirrors 2710, 2712, 2714 include mirrors that reflect a first wavelength of light but transmit (or are transparent to) a second wavelength of light. For example, the third dichroic mirror 2714 may reflect blue laser light provided by the third emitter, while being transparent to the red and green light provided by the first emitter 2702 and the second emitter 2704, respectively. The second dichroic mirror 2712 may be transparent to red light from the first emitter 2702, but reflective to green light from the second emitter 2704. If other colors or wavelengths are included dichroic mirrors may be selected to reflect light corresponding to at least one emitter and be transparent to other emitters. For example, the third dichroic mirror 2714 reflect the light form the third emitter 2706 but is to emitters "behind" it, such as the first emitter 2702 and the second emitter 2704. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 2708 at a substantially same angle.

Because the dichroic mirrors allow other wavelengths to transmit or pass through, each of the wavelengths may arrive at the collection region 2708 from a same angle and/or with the same center or focal point. Providing light from the same angle and/or same focal/center point can significantly improve reception and color mixing at the collection region 2708. For example, a specific fiber may receive the different colors in the same proportions they were transmitted/reflected by the emitters 2702, 2704, 2706 and mirrors 2710, 2712, 2714. Light mixing may be significantly improved at the collection region compared to the embodiment of FIG. 27B. In one embodiment, any optical components discussed herein may be used at the collection region 2708 to collect light prior to providing it to a fiber or fiber bundle.

FIG. 27C illustrates an embodiment of a light source 2700 with emitters 2702, 2704, 2706 that also provide light to the collection region 2708 at the same or substantially same angle. However, the light incident on the collection region 2708 is offset from being perpendicular. Angle 2716 indicates the angle offset from perpendicular. In one embodiment, the laser emitters 2702, 2704, 2706 may have cross sectional intensity profiles that are Gaussian. As discussed previously, improved distribution of light energy between fibers may be accomplished by creating a more flat or top-hat shaped intensity profile. In one embodiment, as the angle 2716 is increased, the intensity across the collection region 2708 approaches a top hat profile. For example, a top-hat profile may be approximated even with a non-flat output beam by increasing the angle 2716 until the profile is sufficiently flat. The top hat profile may also be accomplished using one or more lenses, diffusers, mixing rods, or any other intervening optical component between the emitters 2702, 2704, 2706 and an output waveguide, fiber, or fiber optic bundle.

Figure 28:
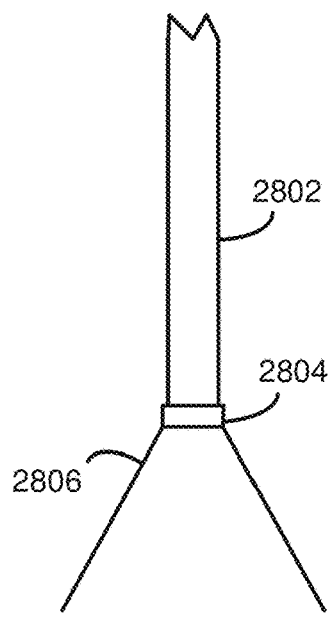
FIG. 28 illustrates a single optical fiber outputting via a diffuser at an output to illuminate a scene in a light deficient environment.

FIG. 28 is a schematic diagram illustrating a single optical fiber 2802 outputting via a diffuser 2804 at an output. In one embodiment, the optical fiber 2802 has a diameter of 500 microns, a numerical aperture of 0.65, and emits a light cone 2806 of about 70 or 80 degrees without a diffuser 2804. With the diffuser 2804, the light cone 2806 may have an angle of about 110 or 120 degrees. The light cone 2806 may be a majority of where all light goes and is evenly distributed. The diffuser 2804 may allow for more even distribution of electromagnetic energy of a scene observed by an image sensor.

In one embodiment, the lumen waveguide 210 includes a single plastic or glass optical fiber of about 500 microns. The plastic fiber may be low cost, but the width may allow the fiber to carry a sufficient amount of light to a scene, with coupling, diffusion, or other losses. For example, smaller fibers may not be able to carry as much light or power as a larger fiber. The lumen waveguide 210 may include a single or a plurality of optical fibers. The lumen waveguide 210 may receive light directly from the light source or via a jumper waveguide. A diffuser may be used to broaden the light output 206 for a desired field of view of the image sensor 214 or other optical components.

Although three emitters are shown in FIGS. 27A-27C, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums). The emitters may be configured to emit visible light such as red light, green light, and blue light, and may further be configured to emit hyperspectral emissions of electromagnetic radiation, fluorescence excitation wavelengths for fluorescing a reagent, and/or laser mapping patterns for calculating parameters and distances between objects in a scene.

Figure 29:
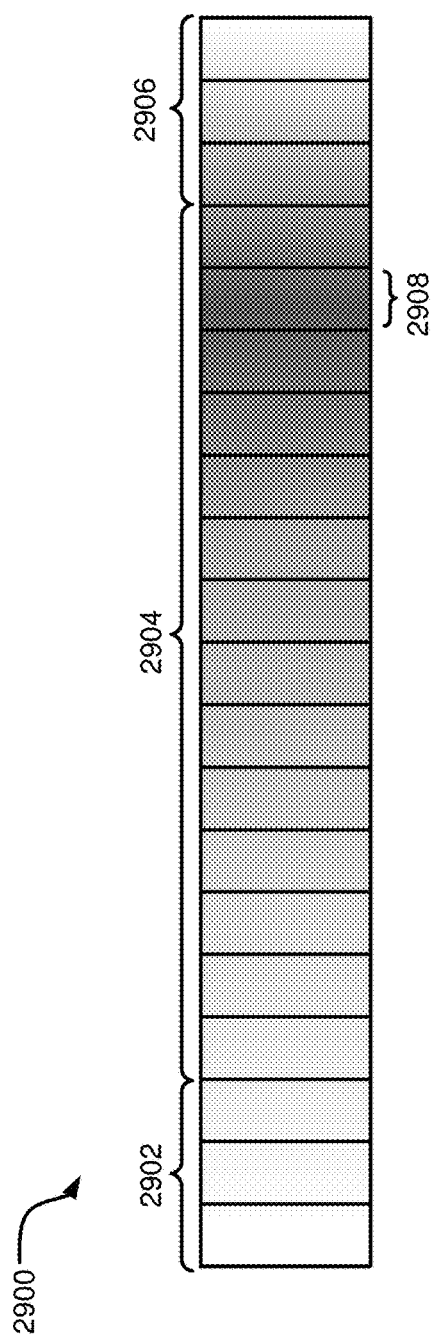
FIG. 29 illustrates a portion of the electromagnetic spectrum divided into a plurality of different sub-spectrums which may be emitted by emitters of a light source in accordance with the principles and teachings of the disclosure.

FIG. 29 illustrates a portion of the electromagnetic spectrum 2900 divided into twenty different sub-spectrums. The number of sub-spectrums is illustrative only. In at least one embodiment, the spectrum 2900 may be divided into hundreds of sub-spectrums, each with a small waveband. The spectrum may extend from the infrared spectrum 2902, through the visible spectrum 2904, and into the ultraviolet spectrum 2906. The sub-spectrums each have a waveband 2908 that covers a portion of the spectrum 2900. Each waveband may be defined by an upper wavelength and a lower wavelength.

Hyperspectral imaging includes imaging information from across the electromagnetic spectrum 2900. A hyperspectral pulse of electromagnetic radiation may include a plurality of sub-pulses spanning one or more portions of the electromagnetic spectrum 2900 or the entirety of the electromagnetic spectrum 2900. A hyperspectral pulse of electromagnetic radiation may include a single partition of wavelengths of electromagnetic radiation. A resulting hyperspectral exposure frame includes information sensed by the pixel array subsequent to a hyperspectral pulse of electromagnetic radiation. Therefore, a hyperspectral exposure frame may include data for any suitable partition of the electromagnetic spectrum 2900 and may include multiple exposure frames for multiple partitions of the electromagnetic spectrum 2900. In an embodiment, a hyperspectral exposure frame includes multiple hyperspectral exposure frames such that the combined hyperspectral exposure frame comprises data for the entirety of the electromagnetic spectrum 2900.

In one embodiment, at least one emitter (such as a laser emitter) is included in a light source (such as the light sources 202, 3000) for each sub-spectrum to provide complete and contiguous coverage of the whole spectrum 2900. For example, a light source for providing coverage of the illustrated sub-spectrums may include at least 20 different emitters, at least one for each sub-spectrum. In one embodiment, each emitter covers a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral and/or fluorescence imaging. The waveband widths may allow for selectively emitting the excitation wavelength(s) for one or more particular fluorescent reagents. Additionally, the waveband widths may allow for selectively emitting certain partitions of hyperspectral electromagnetic radiation for identifying specific structures, chemical processes, tissues, biological processes, and so forth. Because the wavelengths come from emitters which can be selectively activated, extreme flexibility for fluorescing one or more specific fluorescent reagents during an examination can be achieved. Additionally, extreme flexibility for identifying one or more objects or processes by way of hyperspectral imaging can be achieved. Thus, much more fluorescence and/or hyperspectral information may be achieved in less time and within a single examination which would have required multiple examinations, delays because of the administration of dyes or stains, or the like.

Figure 30:
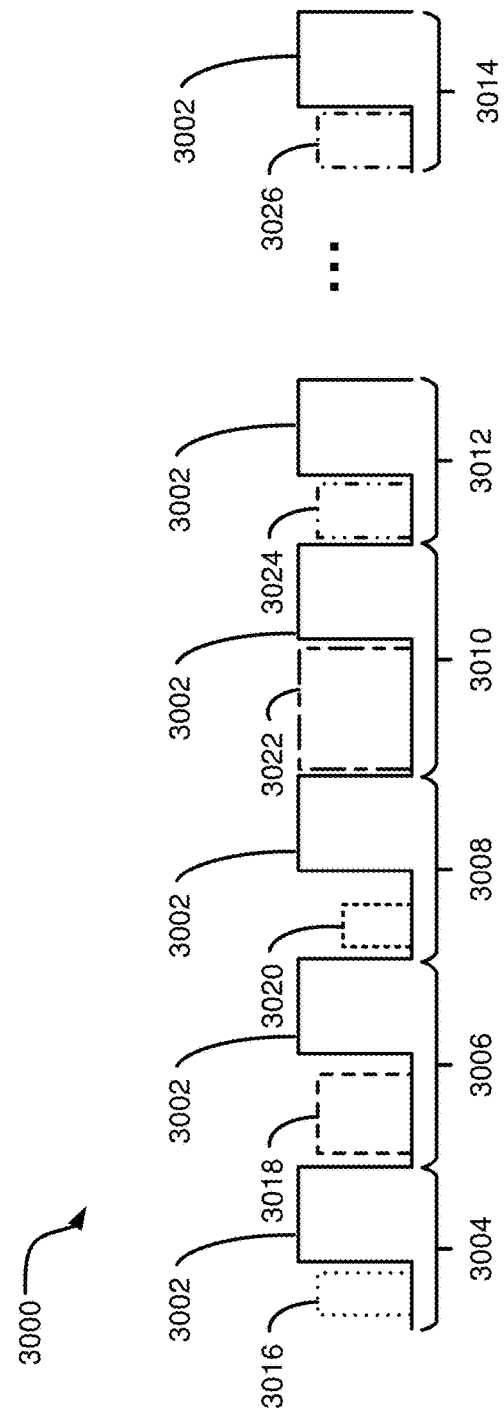
FIG. 30 is a schematic diagram illustrating a timing sequence for emission and readout for generating an image frame comprising a plurality of exposure frames resulting from differing partitions of pulsed light.

FIG. 30 is a schematic diagram illustrating a timing diagram 3000 for emission and readout for generating an image. The solid line represents readout (peaks 3002) and blanking periods (valleys) for capturing a series of exposure frames 3004-3014. The series of exposure frames 3004-3014 may include a repeating series of exposure frames which may be used for generating laser mapping, hyperspectral, and/or fluorescence data that may be overlaid on an RGB video stream. In an embodiment, a single image frame comprises information from multiple exposure frames, wherein one exposure frame includes red image data, another exposure frame includes green image data, and another exposure frame includes blue image data. Additionally, the single image frame may include one or more of hyperspectral image data, fluorescence image data, and laser mapping data. The multiple exposure frames are combined to produce the single image frame. The single image frame is an RGB image with hyperspectral imaging data. The series of exposure frames include a first exposure frame 3004, a second exposure frame 3006, a third exposure frame 3008, a fourth exposure frame 3010, a fifth exposure frame 3012, and an Nth exposure frame 3026.

Additionally, the hyperspectral image data, the fluorescence image data, and the laser mapping data can be used in combination to identify critical tissues or structures and further to measure the dimensions of those critical tissues or structures. For example, the hyperspectral image data may be provided to a corresponding system to identify certain critical structures in a body such as a nerve, ureter, blood vessel, cancerous tissue, and so forth. The location and identification of the critical structures may be received from the corresponding system and may further be used to generate topology of the critical structures using the laser mapping data. For example, a corresponding system determines the location of a cancerous tumor based on hyperspectral imaging data. Because the location of the cancerous tumor is known based on the hyperspectral imaging data, the topology and distances of the cancerous tumor may then be calculated based on laser mapping data. This example may also apply when a cancerous tumor or other structure is identified based on fluorescence imaging data.

In one embodiment, each exposure frame is generated based on at least one pulse of electromagnetic energy. The pulse of electromagnetic energy is reflected and detected by an image sensor and then read out in a subsequent readout (3002). Thus, each blanking period and readout results in an exposure frame for a specific spectrum of electromagnetic energy. For example, the first exposure frame 3004 may be generated based on a spectrum of a first one or more pulses 3016, a second exposure frame 3006 may be generated based on a spectrum of a second one or more pulses 3018, a third exposure frame 3008 may be generated based on a spectrum of a third one or more pulses 3020, a fourth exposure frame 3010 may be generated based on a spectrum of a fourth one or more pulses 3022, a fifth exposure frame 3012 may be generated based on a spectrum of a fifth one or more pulses 3024, and an Nth exposure frame 3026 may be generated based on a spectrum of an Nth one or more pulses 3026.

The pulses 3016-3026 may include energy from a single emitter or from a combination of two or more emitters. For example, the spectrum included in a single readout period or within the plurality of exposure frames 3004-3014 may be selected for a desired examination or detection of a specific tissue or condition. According to one embodiment, one or more pulses may include visible spectrum light for generating an RGB or black and white image while one or more additional pulses are emitted to sense a spectral response to a hyperspectral wavelength of electromagnetic radiation. For example, pulse 3016 may include red light, pulse 3018 may include blue light, and pulse 3020 may include green light while the remaining pulses 3022-3026 may include wavelengths and spectrums for detecting a specific tissue type, fluorescing a reagent, and/or mapping the topology of the scene. As a further example, pulses for a single readout period include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on a spectral response of the tissue and/or whether a fluorescent reagent is present at the tissue.

The plurality of frames 3004-3014 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a fluorescent reagent is provided to a patient, and the fluorescent reagent is configured to adhere to cancerous cells. The fluorescent reagent is known to fluoresce when radiated with a specific partition of electromagnetic radiation. The relaxation wavelength of the fluorescent reagent is also known. In the example implementation, the patient is imaged with an endoscopic imaging system as discussed herein. The endoscopic imaging system pulses partitions of red, green, and blue wavelengths of light to generate an RGB video stream of the interior of the patient's body. Additionally, the endoscopic imaging system pulses the excitation wavelength of electromagnetic radiation for the fluorescent reagent that was administered to the patient. In the example, the patient has cancerous cells and the fluorescent reagent has adhered to the cancerous cells. When the endoscopic imaging system pulses the excitation wavelength for the fluorescent reagent, the fluorescent reagent will fluoresce and emit a relaxation wavelength. If the cancerous cells are present in the scene being imaged by the endoscopic imaging system, then the fluorescent reagent will also be present in the scene and will emit its relaxation wavelength after fluorescing due to the emission of the excitation wavelength. The endoscopic imaging system senses the relaxation wavelength of the fluorescent reagent and thereby senses the presence of the fluorescent reagent in the scene. Because the fluorescent reagent is known to adhere to cancerous cells, the presence of the fluorescent reagent further indicates the presence of cancerous cells within the scene. The endoscopic imaging system thereby identifies the location of cancerous cells within the scene. The endoscopic imaging system may further emit a laser mapping pulsing scheme for generating a topology of the scene and calculating dimensions for objects within the scene. The location of the cancerous cells (as identified by the fluorescence imaging data) may be combined with the topology and dimensions information calculated based on the laser mapping data. Therefore, the precise location, size, dimensions, and topology of the cancerous cells may be identified. This information may be provided to a medical practitioner to aid in excising the cancerous cells. Additionally, this information may be provided to a robotic surgical system to enable the surgical system to excise the cancerous cells.

In a further example implementation, a patient is imaged with an endoscopic imaging system to identify quantitative diagnostic information about the patient's tissue pathology. In the example, the patient is suspected or known to suffer from a disease that can be tracked with hyperspectral imaging to observe the progression of the disease in the patient's tissue. The endoscopic imaging system pulses partitions of red, green, and blue wavelengths of light to generate an RGB video stream of the interior of the patient's body. Additionally, the endoscopic imaging system pulses one or more hyperspectral wavelengths of light that permit the system to "see through" some tissues and generate imaging of the tissue that is affected by the disease. The endoscopic imaging system senses the reflected hyperspectral electromagnetic radiation to generate hyperspectral imaging data of the diseased tissue, and thereby identifies the location of the diseased tissue within the patient's body. The endoscopic imaging system may further emit a laser mapping pulsing scheme for generating a topology of the scene and calculating dimensions of objects within the scene. The location of the diseased tissue (as identified by the hyperspectral imaging data) may be combined with the topology and dimensions information that is calculated with the laser mapping data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 31:
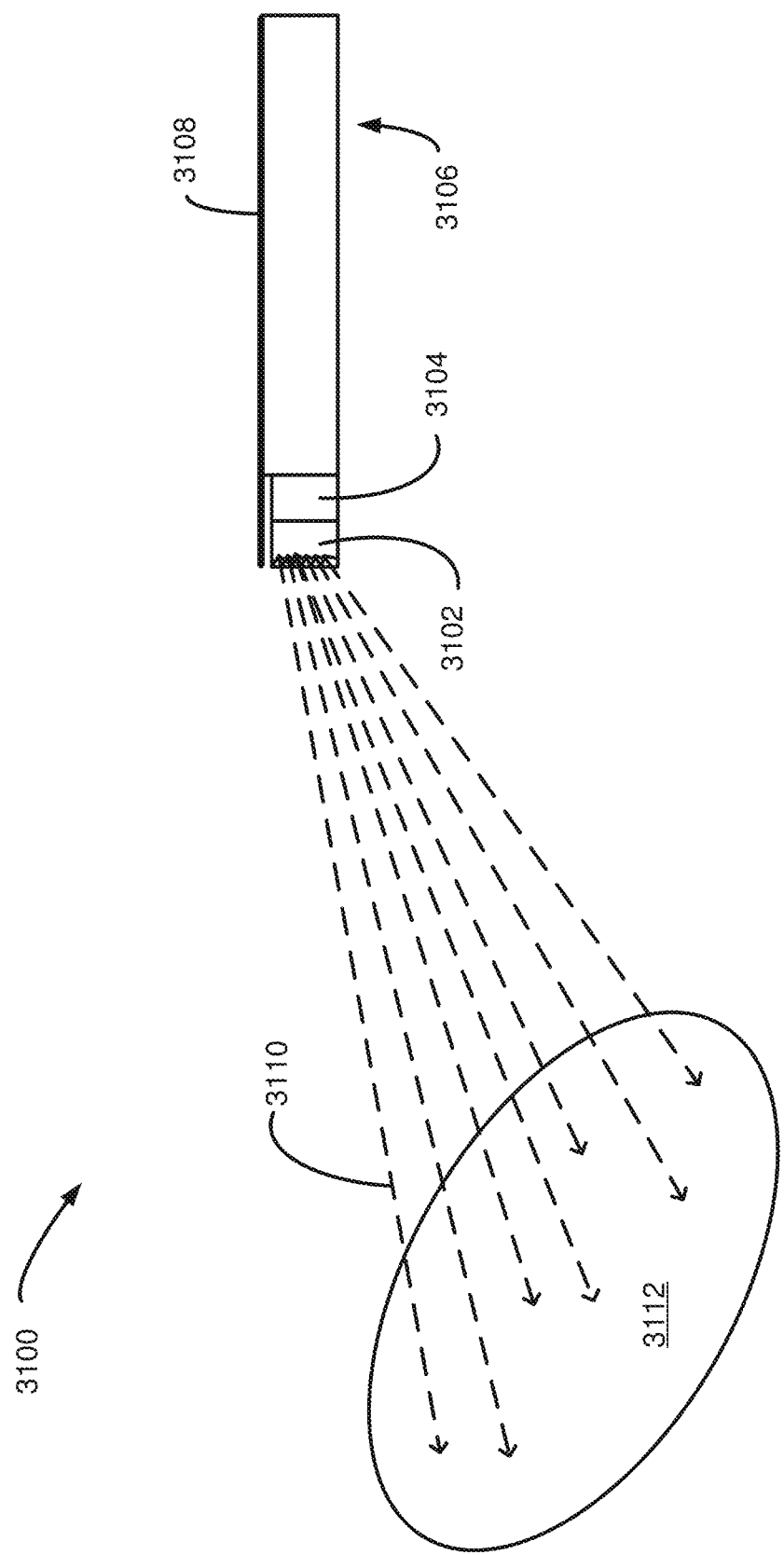
FIG. 31 illustrates an imaging system including a single cut filter for filtering wavelengths of electromagnetic radiation.

FIG. 31 is a schematic diagram of an imaging system 3100 having a single cut filter. The system 3100 includes an endoscope 3106 or other suitable imaging device having a light source 3108 for use in a light deficient environment. The endoscope 3106 includes an image sensor 3104 and a filter 3102 for filtering out unwanted wavelengths of light or other electromagnetic radiation before reaching the image sensor 3104. The light source 3108 transmits light that may illuminate the surface 3112 in a light deficient environment such as a body cavity. The light 3110 is reflected off the surface 3112 and passes through the filter 3102 before hitting the image sensor 3104.

The filter 3102 may be used in an implementation where a fluorescent reagent or dye has been administered. In such an embodiment, the light source 3108 emits the excitation wavelength for fluorescing the fluorescent reagent or dye. Commonly, the relaxation wavelength emitted by the fluorescent reagent or dye will be of a different wavelength than the excitation wavelength. The filter 3102 may be selected to filter out the excitation wavelength and permit only the relaxation wavelength to pass through the filter and be sensed by the image sensor 3104.

In one embodiment, the filter 3102 is configured to filter out an excitation wavelength of electromagnetic radiation that causes a reagent or dye to fluoresce such that only the expected relaxation wavelength of the fluoresced reagent or dye is permitted to pass through the filter 3102 and reach the image sensor 3104. In an embodiment, the filter 3102 filters out at least a fluorescent reagent excitation wavelength between 770 nm and 790 nm. In an embodiment, the filter 3102 filters out at least a fluorescent reagent excitation wavelength between 795 nm and 815 nm. In an embodiment, the filter 3102 filters out at least a fluorescent reagent excitation wavelength between 770 nm and 790 nm and between 795 nm and 815 nm. In these embodiments, the filter 3102 filters out the excitation wavelength of the reagent and permits only the relaxation wavelength of the fluoresced reagent to be read by the image sensor 3104. The image sensor 3104 may be a wavelength-agnostic image sensor and the filter 3102 may be configured to permit the image sensor 3104 to only receive the relaxation wavelength of the fluoresced reagent and not receive the emitted excitation wavelength for the reagent. The data determined by the image sensor 3104 may then indicate a presence of a critical body structure, tissue, biological process, or chemical process as determined by a location of the reagent or dye.

The filter 3102 may further be used in an implementation where a fluorescent reagent or dye has not been administered. The filter 3102 may be selected to permit wavelengths corresponding to a desired spectral response to pass through and be read by the image sensor 3104. The image sensor 3104 may be a monochromatic image sensor such that pixels of the captured image that exceed a threshold or fall below a threshold may be characterized as corresponding to a certain spectral response or fluorescence emission. The spectral response or fluorescence emission, as determined by the pixels captured by the image sensor 3104, may indicate the presence of a certain body tissue or structure, a certain condition, a certain chemical process, and so forth.

Figure 32:
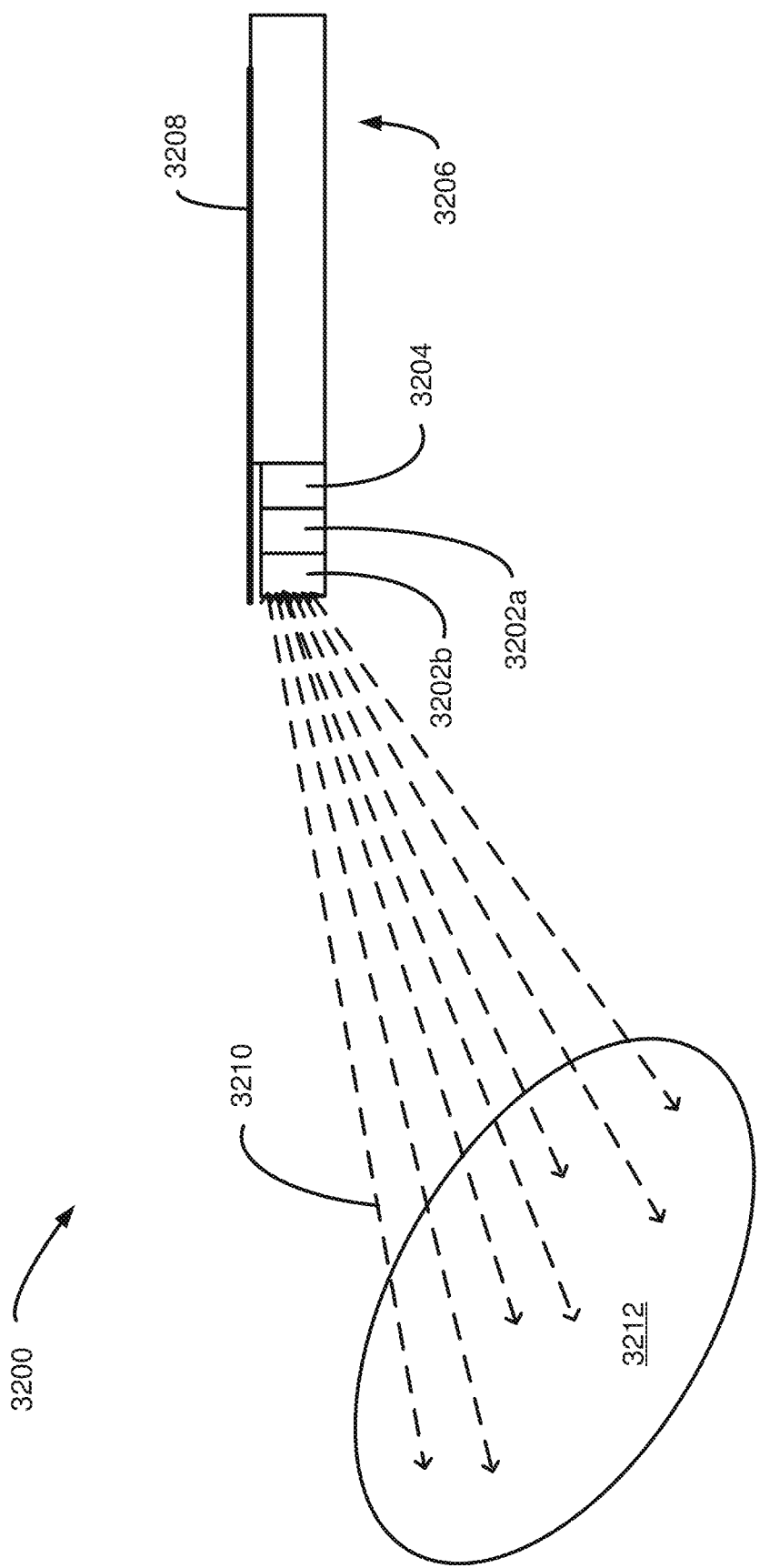
FIG. 32 illustrates an imaging system comprising a multiple cut filter for filtering wavelengths of electromagnetic radiation.

FIG. 32 is a schematic diagram of an imaging system 3200 having multiple cut filters. The system 3200 includes an endoscope 3206 or other suitable imaging device having a light source 3208 for use in a light deficient environment. The endoscope 3206 includes an image sensor 3204 and two filters 3202a, 3202b. It should be appreciated that in alternative embodiments, the system 3200 may include any number of filters, and the number of filters and the type of filters may be selected for a certain purpose e.g., for gathering imaging information of a particular body tissue, body condition, chemical process, and so forth. The filters 3202a, 3202b are configured for preventing unwanted wavelengths of light or other electromagnetic radiation from being sensed by the image sensor 3204. The filters 3202a, 3202b may be configured to filter out unwanted wavelengths from white light or other electromagnetic radiation that may be emitted by the light source 3208.

Further to the disclosure with respect to FIG. 31, the filters 3202a, 3202b may be used in an implementation where a fluorescent reagent or dye has been administered. The filters 3202a, 3202b may be configured for blocking an emitted excitation wavelength for the reagent or dye and permitting the image sensor 3204 to only read the relaxation wavelength of the reagent or dye. Further, the filters 3202a, 3202b may be used in an implementation where a fluorescent reagent or dye has not been administered. In such an implementation, the filters 3202a, 3202b may be selected to permit wavelengths corresponding to a desired spectral response to pass through and be read by the image sensor 3204.

The multiple filters 3202a, 3202b may each be configured for filtering out a different range of wavelengths of the electromagnetic spectrum. For example, one filter may be configured for filtering out wavelengths longer than a desired wavelength range and the additional filter may be configured for filtering out wavelengths shorter than the desired wavelength range. The combination of the two or more filters may result in only a certain wavelength or band of wavelengths being read by the image sensor 3204.

In an embodiment, the filters 3202a, 3202b are customized such that electromagnetic radiation between 513 nm and 545 nm contacts the image sensor 3204. In an embodiment, the filters 3202a, 3202b are customized such that electromagnetic radiation between 565 nm and 585 nm contacts the image sensor 3204. In an embodiment, the filters 3202a, 3202b are customized such that electromagnetic radiation between 900 nm and 1000 nm contacts the image sensor 3204. In an embodiment, the filters 3202a, 3202b are customized such that electromagnetic radiation between 425 nm and 475 nm contacts the image sensor 3204. In an embodiment, the filters 3202a, 3202b are customized such that electromagnetic radiation between 520 nm and 545 nm contacts the image sensor 3204. In an embodiment, the filters 3202a, 3202b are customized such that electromagnetic radiation between 625 nm and 645 nm contacts the image sensor 3204. In an embodiment, the filters 3202a, 3202b are customized such that electromagnetic radiation between 760 nm and 795 nm contacts the image sensor 3204. In an embodiment, the filters 3202a, 3202b are customized such that electromagnetic radiation between 795 nm and 815 nm contacts the image sensor 3204. In an embodiment, the filters 3202a, 3202b are customized such that electromagnetic radiation between 370 nm and 420 nm contacts the image sensor 3204. In an embodiment, the filters 3202a, 3202b are customized such that electromagnetic radiation between 600 nm and 670 nm contacts the image sensor 3204. In an embodiment, the filters 3202a, 3202b are configured for permitting only a certain fluorescence relaxation emission to pass through the filters 3202a, 3202b and contact the image sensor 3204.

In an embodiment, the system 3200 includes multiple image sensors 3204 and may particularly include two image sensors for use in generating a three-dimensional image. The image sensor(s) 3204 may be color/wavelength agnostic and configured for reading any wavelength of electromagnetic radiation that is reflected off the surface 3212. In an embodiment, the image sensors 3204 are each color dependent or wavelength dependent and configured for reading electromagnetic radiation of a particular wavelength that is reflected off the surface 3212 and back to the image sensors 3204. Alternatively, the image sensor 3204 may include a single image sensor with a plurality of different pixel sensors configured for reading different wavelengths or colors of light, such as a Bayer filter color filter array. Alternatively, the image sensor 3204 may include one or more color agnostic image sensors that may be configured for reading different wavelengths of electromagnetic radiation according to a pulsing schedule such as those illustrated in FIGS. 5-7E and 15-16, for example.

FIG. 33 is a schematic diagram illustrating a system 3300 for mapping a surface and/or tracking an object in a light deficient environment through laser mapping imaging. In an embodiment, an endoscope 3302 in a light deficient environment pulses a grid array 3306 (may be referred to as a laser map pattern) on a surface 3304. The grid array 3306 includes vertical hashing 3308 and horizontal hashing 3310 in one embodiment as illustrated in FIG. 33. It should be appreciated the grid array 3306 may include any suitable array for mapping a surface 3304, including, for example, a raster grid of discrete points, an occupancy grid map, a dot array, and so forth. Additionally, the endoscope 3302 may pulse multiple grid arrays 3306 and may, for example, pulse one or more individual grid arrays on each of a plurality of objects or structures within the light deficient environment.

In an embodiment, the system 3300 pulses a grid array 3306 that may be used for mapping a three-dimensional topology of a surface and/or tracking a location of an object such as a tool or another device in a light deficient environment. In an embodiment, the system 3300 provides data to a third-party system or computer algorithm for determining surface dimensions and configurations by way of light detection and ranging (LIDAR) mapping. The system 3300 may pulse any suitable wavelength of light or electromagnetic radiation in the grid array 3306, including, for example, ultraviolet light, visible, light, and/or infrared or near infrared light. The surface 3304 and/or objects within the environment may be mapped and tracked at very high resolution and with very high accuracy and precision.

In an embodiment, the system 3300 includes an imaging device having a tube, one or more image sensors, and a lens assembly having an optical element corresponding to the one or more image sensors. The system 3300 may include a light engine having an emitter generating one or more pulses of electromagnetic radiation and a lumen transmitting the one or more pulses of electromagnetic radiation to a distal tip of an endoscope within a light deficient environment such as a body cavity. In an embodiment, at least a portion of the one or more pulses of electromagnetic radiation includes a laser map pattern that is emitted onto a surface within the light deficient environment, such as a surface of body tissue and/or a surface of tools or other devices within the body cavity. The endoscope 3302 may include a two-dimensional, three-dimensional, or n-dimensional camera for mapping and/or tracking the surface, dimensions, and configurations within the light deficient environment.

In an embodiment, the system 3300 includes a processor for determining a distance of an endoscope or tool from an object such as the surface 3304. The processor may further determine an angle between the endoscope or tool and the object. The processor may further determine surface area information about the object, including for example, the size of surgical tools, the size of structures, the size of anatomical structures, location information, and other positional data and metrics. The system 3300 may include one or more image sensors that provide image data that is output to a control system for determining a distance of an endoscope or tool to an object such as the surface 3304. The image sensors may output information to a control system for determining an angle between the endoscope or tool to the object. Additionally, the image sensors may output information to a control system for determining surface area information about the object, the size of surgical tools, size of structures, size of anatomical structures, location information, and other positional data and metrics.

In an embodiment, the grid array 3306 is pulsed by an emitter of the endoscope 3302 at a sufficient speed such that the grid array 3306 is not visible to a user. In various implementations, it may be distracting to a user to see the grid array 3306 during an endoscopic imaging procedure and/or endoscopic surgical procedure. The grid array 3306 may be pulsed for sufficiently brief periods such that the grid array 3306 cannot be detected by a human eye. In an alternative embodiment, the endoscope 3302 pulses the grid array 3306 at a sufficient recurring frequency such that the grid array 3306 may be viewed by a user. In such an embodiment, the grid array 3306 may be overlaid on an image of the surface 3304 on a display. The grid array 3306 may be overlaid on a black-and-white or RGB image of the surface 3304 such that the grid array 3306 may be visible by a user during use of the system 3300. A user of the system 3300 may indicate whether the grid array 3306 should be overlaid on an image of the surface 3304 and/or whether the grid array 3306 should be visible to the user. The system 3300 may include a display that provides real-time measurements of a distance from the endoscope 3302 to the surface 3304 or another object within the light deficient environment. The display may further provide real-time surface area information about the surface 3304 and/or any objects, structures, or tools within the light deficient environment. The accuracy of the measurements may be accurate to less than one millimeter.

In an embodiment, the system 3300 pulses a plurality of grid arrays 3306. In an embodiment, each of the plurality of grid arrays 3306 corresponds to a tool or other device present within the light deficient environment. The precise locations and parameters of each of the tools and other devices may be tracked by pulsing and sensing the plurality of grid arrays 3306. The information generated by sensing the reflected grid arrays 3306 can be assessed to identify relative locations of the tools and other devices within the light deficient environment.

The endoscope 3302 may pulse electromagnetic radiation according to a pulsing schedule such as those illustrated herein that may further include pulsing of the grid array 3306 along with pulsing Red, Green, and Blue light for generating an RGB image and further generating a grid array 3306 that may be overlaid on the RGB image and/or used for mapping and tracking the surface 3304 and objects within the light deficient environment. The grid array 3306 may additionally be pulsed in conjunction with hyperspectral or fluorescent excitation wavelengths of electromagnetic radiation. The data from each of the RGB imaging, the laser mapping imaging, the hyperspectral imaging, and the fluorescence imaging may be combined to identify the locations, dimensions, and surface topology of critical structures in a body.

In an embodiment, the endoscope 3302 includes one or more color agnostic image sensors. In an embodiment, the endoscope 3302 includes two color agnostic image sensors for generating a three-dimensional image or map of the light deficient environment. The image sensors may generate an RGB image of the light deficient environment according to a pulsing schedule as disclosed herein. Additionally, the image sensors may determine data for mapping the light deficient environment and tracking one or more objects within the light deficient environment based on data determined when the grid array 3306 is pulsed. Additionally, the image sensors may determine spectral or hyperspectral data along with fluorescence imaging data according to a pulsing schedule that may be modified by a user to suit the particular needs of an imaging procedure. In an embodiment, a pulsing schedule includes Red, Green, and Blue pulses along with pulsing of a grid array 3306 and/or pulsing for generating hyperspectral image data and/or fluorescence image data. In various implementations, the pulsing schedule may include any suitable combination of pulses of electromagnetic radiation according to the needs of a user. The recurring frequency of the different wavelengths of electromagnetic radiation may be determined based on, for example, the energy of a certain pulse, the needs of the user, whether certain data (for example, hyperspectral data and/or fluorescence imaging data) needs to be continuously updated or may be updated less frequently, and so forth.

The pulsing schedule may be modified in any suitable manner, and certain pulses of electromagnetic radiation may be repeated at any suitable frequency, according to the needs of a user or computer-implemented program for a certain imaging procedure. For example, in an embodiment where surface tracking data generated based on the grid array 3306 is provided to a computer-implemented program for use in, for example, a robotic surgical procedure, the grid array 3306 may be pulsed more frequently than if the surface tracking data is provided to a user who is visualizing the scene during the imaging procedure. In such an embodiment where the surface tracking data is used for a robotic surgical procedure, the surface tracking data may need to be updated more frequently or may need to be exceedingly accurate such that the computer-implemented program may execute the robotic surgical procedure with precision and accuracy.

In an embodiment, the system 3300 is configured to generate an occupancy grid map comprising an array of cells divided into grids. The system 3300 is configured to store height values for each of the respective grid cells to determine a surface mapping of a three-dimensional environment in a light deficient environment.

Figure 34A:
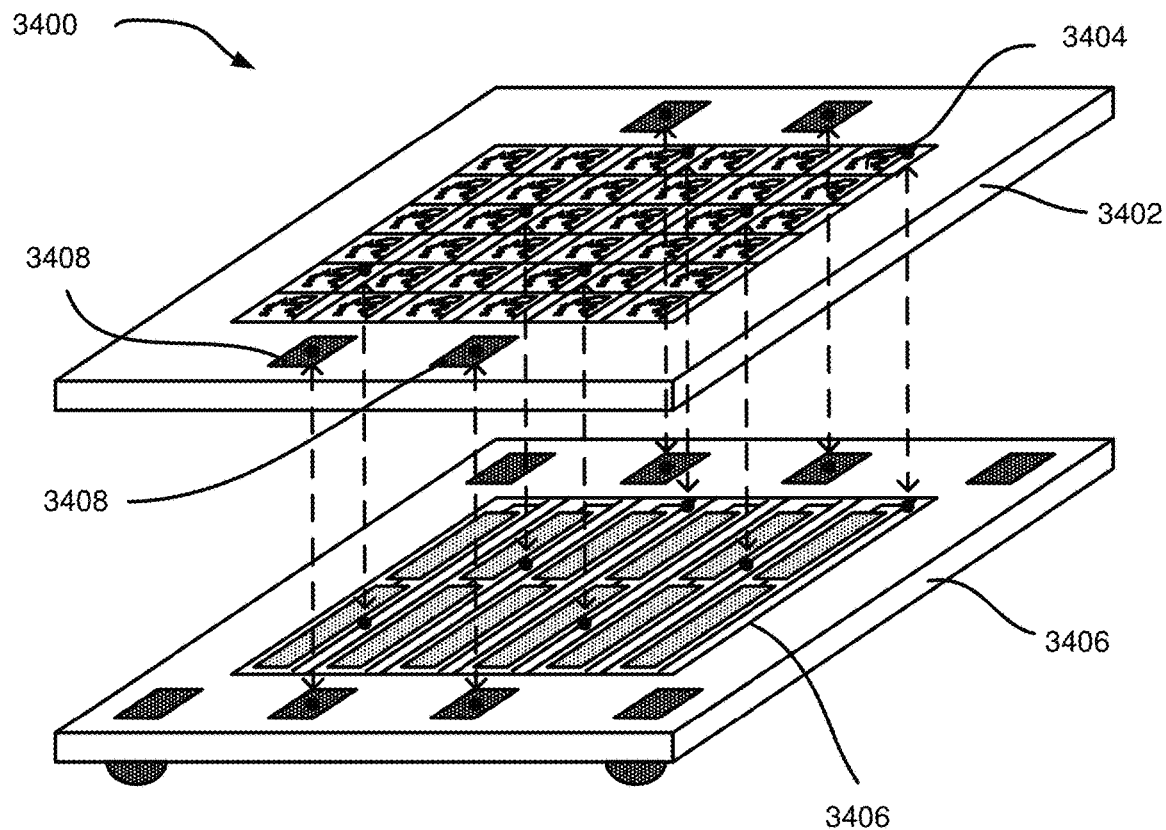
FIGS. 34A and 34B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 34B:
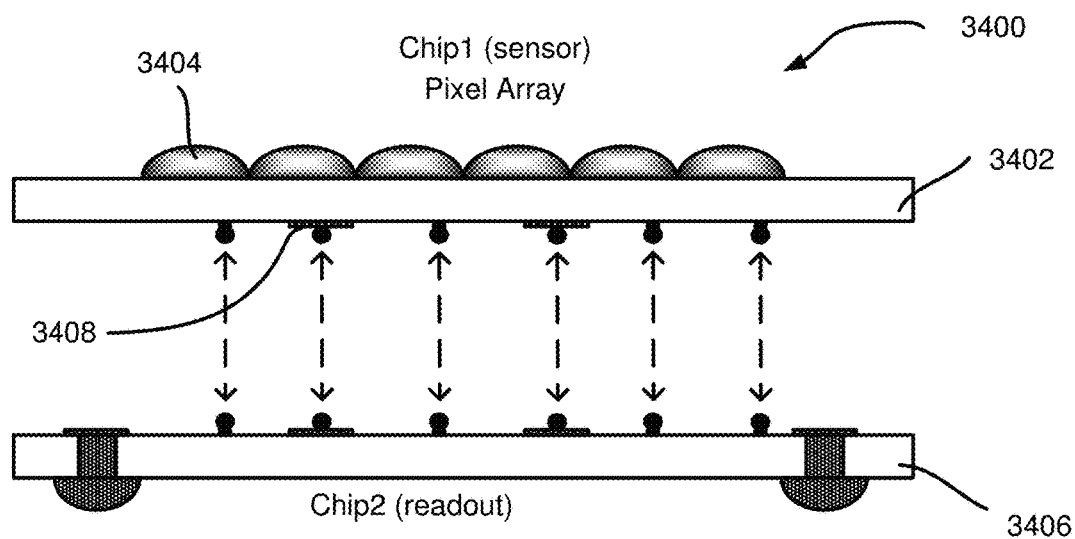

FIGS. 34A and 34B illustrate a perspective view and a side view, respectively, of an implementation of an imaging sensor 3400 built on a plurality of substrates. As illustrated, a plurality of pixel columns 3404 forming the pixel array are located on the first substrate 3402 and a plurality of circuit columns 3408 are located on a second substrate 3406. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 3402 of the two substrates/chips may be processed using an image CMOS process. The first substrate/chip 3402 may be comprised either of a pixel array exclusively or a pixel array surrounded by limited circuitry. The second or subsequent substrate/chip 3406 may be processed using any process and does not have to be from an image CMOS process. The second substrate/chip 3406 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 3402 may be stacked with the second or subsequent substrate/chip 3406 using any three-dimensional technique. The second substrate/chip 3406 may support most, or a majority, of the circuitry that would have otherwise been implemented in the first image CMOS chip 3402 (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wire bonds, bump and/or TSV (Through Silicon Via).

Figure 35A:
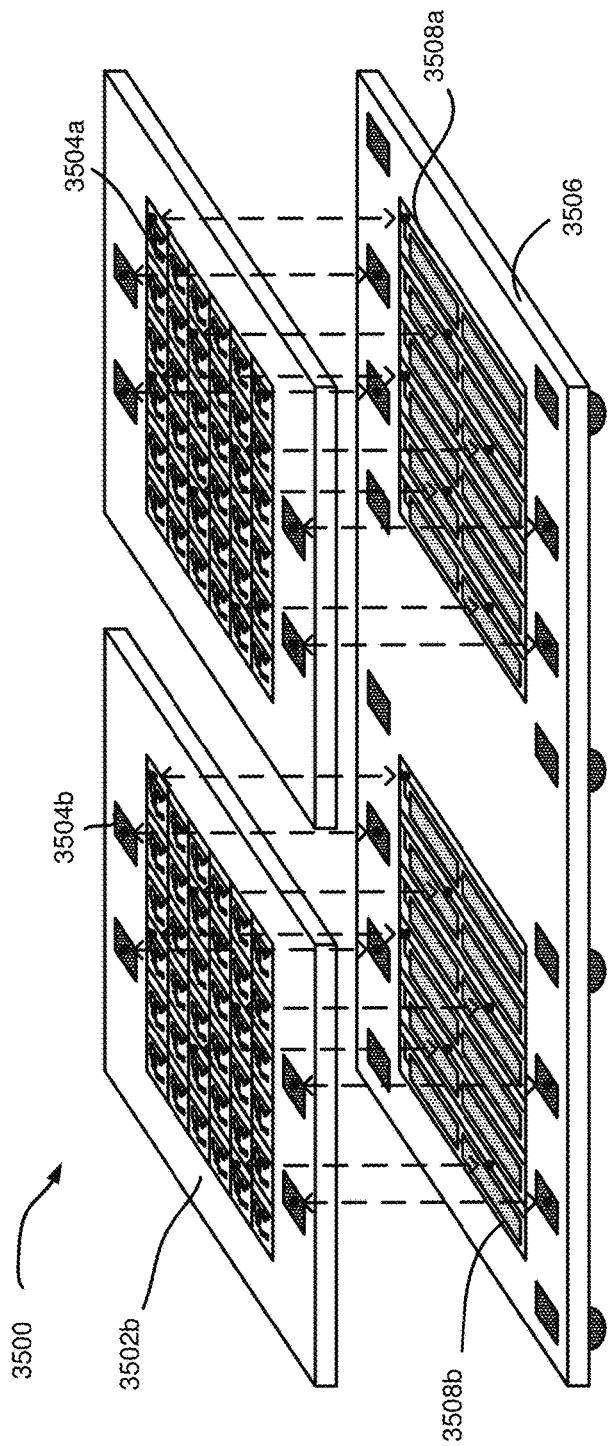
FIGS. 35A and 35B illustrate a perspective view and a side view, respectively, of an implementation of an imaging sensor having a plurality of pixel arrays for producing a three-dimensional image, wherein the plurality of pixel arrays and the image sensor are built on a plurality of substrates.
Figure 35B:
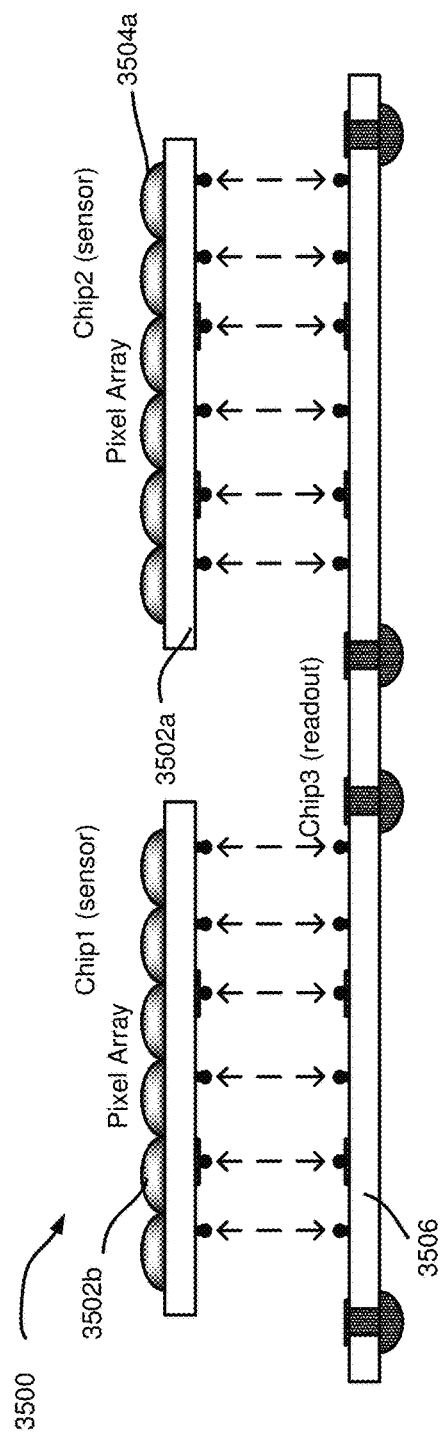

FIGS. 35A and 35B illustrate a perspective view and a side view, respectively, of an implementation of an imaging sensor 3500 having a plurality of pixel arrays for producing a three-dimensional image. The three-dimensional image sensor may be built on a plurality of substrates and may comprise the plurality of pixel arrays and other associated circuitry, wherein a plurality of pixel columns 3504a forming the first pixel array and a plurality of pixel columns 3504b forming a second pixel array are located on respective substrates 3502a and 3502b, respectively, and a plurality of circuit columns 3508a and 3508b are located on a separate substrate 3506. Also illustrated are the electrical connections and communications between columns of pixels to associated or corresponding column of circuitry.

The plurality of pixel arrays may sense information simultaneously and the information from the plurality of pixel arrays may be combined to generate a three-dimensional image. In an embodiment, an endoscopic imaging system includes two or more pixel arrays that can be deployed to generate three-dimensional imaging. The endoscopic imaging system may include an emitter for emitting pulses of electromagnetic radiation during a blanking period of the pixel arrays. The pixel arrays may be synced such that the optical black pixels are read (i.e., the blanking period occurs) at the same time for the two or more pixel arrays. The emitter may emit pulses of electromagnetic radiation for charging each of the two or more pixel arrays. The two or more pixel arrays may read their respective charged pixels at the same time such that the readout periods for the two or more pixel arrays occur at the same time or at approximately the same time. In an embodiment, the endoscopic imaging system includes multiple emitters that are each individual synced with one or more pixel arrays of a plurality of pixel arrays. Information from a plurality of pixel arrays may be combined to generate three-dimensional image frames and video streams.

Figure 36A:
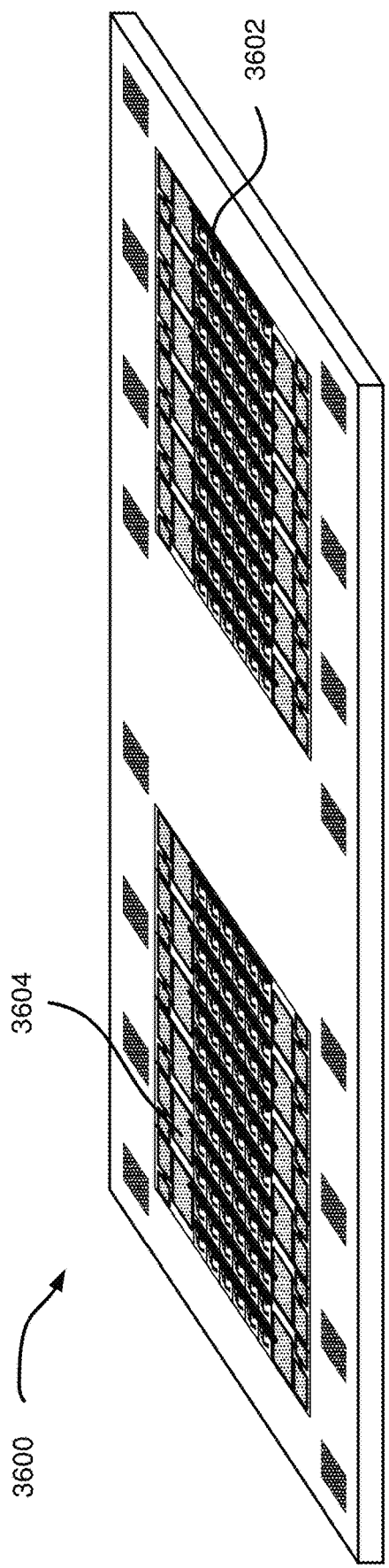
FIGS. 36A and 36B illustrate an implementation having a plurality of pixel arrays for producing a three-dimensional image in accordance with the principles and teachings of the disclosure.
Figure 36B:
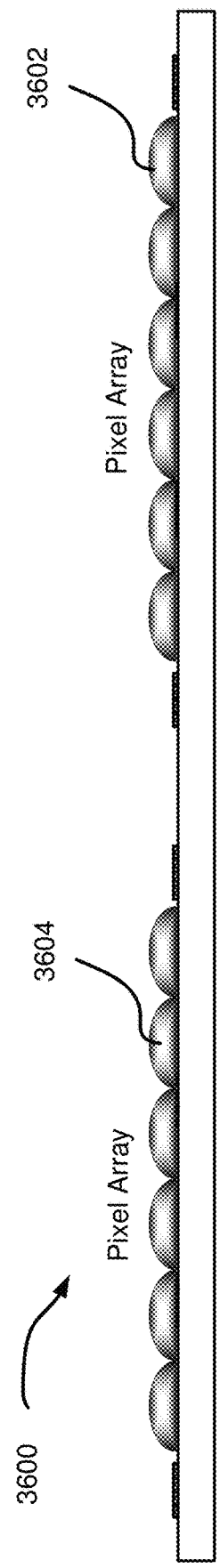

FIGS. 36A and 36B illustrate a perspective view and a side view, respectively, of an implementation of a monolithic sensor 3600 having a plurality of pixel arrays for producing a three-dimensional image in accordance with the teachings and principles of the disclosure. Such an implementation may be desirable for three-dimensional image capture, wherein the two-pixel arrays 3602 and 3604 may be offset during use. In another implementation, a first pixel array 3602 and a second pixel array 3604 may be dedicated to receiving a predetermined range of wave lengths of electromagnetic radiation, wherein the first pixel array is dedicated to a different range of wavelength electromagnetic radiation than the second pixel array.

It will be appreciated that the teachings and principles of the disclosure may be used in a reusable device platform, a limited use device platform, a re-posable use device platform, or a single use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single use/disposable device platform a device is provided sterile to the operating room and used only once before being disposed of.

Examples

The following examples pertain to preferred features of further embodiments:

Example 1 is a system for imaging in a light deficient environment. The system includes an emitter for emitting pulses of electromagnetic radiation and an image sensor comprising a pixel array for sensing reflected electromagnetic radiation, wherein the pixel array comprises a plurality of pixels each configurable as a short exposure pixel or a long exposure pixel. The system includes a controller comprising a processor in electrical communication with the image sensor and the emitter. The system is such that at least a portion of the pulses of electromagnetic radiation emitted by the emitter comprises a laser mapping pattern.

Example 2 is a system as in Example 1, wherein the pixel array comprises a plurality of short exposure pixels and a plurality of long exposure pixels arranged in a checkerboard pattern such that a short exposure pixel is located adjacent to a long exposure pixel.

Example 3 is a system as in any of Examples 1-2, wherein: each of the plurality of pixels of the pixel array comprises a transfer gate transistor; each transfer gate transistor is in electrical communication with a TX signal; and the TX signal provides a global operation for the transfer gate transistors of the plurality of pixels of the pixel array.

Example 4 is a system as in any of Examples 1-3, wherein: the TX signal comprises a TX1 signal and a TX2 signal; at least two pixels of the plurality of pixels of the pixel array share a floating diffusion in a horizontal direction in a two-way pixel share; the TX1 signal communicates with transfer gate transistors of pixels located on a first side of the two-way pixel share on odd rows and with transfer gate transistors of pixels located on a second side of the two-way pixel share on even rows; and the TX2 signal communicates with transfer gate transistors of pixels located on the second side of the two-way pixel share on odd rows and with transfer gate transistors of pixels located on the first side of the two-way pixel share on even rows.

Example 5 is a system as in any of Examples 1-4, wherein the image sensor performs horizontal binning during a charge period of the pixel array.

Example 6 is a system as in any of Examples 1-5, wherein a pixel grouping of the pixel array shares a floating diffusion, wherein the pixel grouping comprises two pixels or four pixels.

Example 7 is a system as in any of Examples 1-6, wherein the pixel array is disposed on a first substrate of the image sensor and supporting circuitry for the pixel array is disposed remotely on a second substrate of the image sensor.

Example 8 is a system as in any of Examples 1-7, wherein the image sensor is configured to generate a plurality of exposure frames, wherein each of the plurality of exposure frames corresponds to a pulse of electromagnetic radiation emitted by the emitter.

Example 9 is a system as in any of Examples 1-8, wherein the pixel array of the image sensor senses reflected electromagnetic radiation to generate the plurality of exposure frames during a readout period of the pixel array, wherein the readout period is a duration of time when active pixels in the pixel array are read.

Example 10 is a system as in any of Examples 1-9, wherein at least a portion of the plurality of exposure frames are combined to form an image frame.

Example 11 is a system as in any of Examples 1-10, wherein the emitter pulses the laser mapping pattern at a duration and frequency such that the laser mapping pattern is not visible to a user of the system.

Example 12 is a system as in any of Examples 1-11, wherein at least a portion of the pulses of electromagnetic radiation emitted by the emitter comprises a green wavelength of electromagnetic radiation, a red wavelength of electromagnetic radiation, and a blue wavelength of electromagnetic radiation.

Example 13 is a system as in any of Examples 1-12, wherein the emitter is configured to emit, during a pulse duration, a plurality of sub-pulses of electromagnetic radiation having a sub-duration shorter than the pulse duration.

Example 14 is a system as in any of Examples 1-13, wherein one or more of the pulses of electromagnetic radiation emitted by the emitter comprise electromagnetic radiation emitted at two or more wavelengths simultaneously as a single pulse or a single sub-pulse.

Example 15 is a system as in any of Examples 1-14, wherein at least one pulse of the pulses of electromagnetic radiation emitted by the emitter results in an exposure frame created by the image sensor, wherein the system further comprises a display for displaying two or more exposure frames as an image frame.

Example 16 is a system as in any of Examples 1-15, wherein at least a portion of the pulses of electromagnetic radiation emitted by the emitter is an excitation wavelength for fluorescing a reagent, and wherein pulsing the excitation wavelength results in the image sensor generating a fluorescence exposure frame indicating a location of the reagent within a scene.

Example 17 is a system as in any of Examples 1-16, wherein the controller is configured to provide the fluorescence exposure frame to a corresponding fluorescence system that determines a location of a critical tissue structure based on the fluorescence exposure frame.

Example 18 is a system as in any of Examples 1-17, wherein the controller is further configured to: receive the location of the critical tissue structure from the corresponding fluorescence system; generate an overlay frame comprising the location of the critical tissue structure; and combine the overlay frame with a color image frame depicting the scene to indicate the location of the critical tissue structure within the scene.

Example 19 is a system as in any of Examples 1-18, wherein the image sensor is configured to sense reflected electromagnetic radiation resulting from the laser mapping pattern to generate a topology exposure frame, and wherein the controller is further configured to: provide the topology exposure frame to a corresponding laser mapping system that determines a topology of the scene and/or dimensions of one or more objects within the scene; provide the location of the critical tissue structure to the corresponding laser mapping system; and receive a topology and/or dimension of the critical tissue structure from the corresponding laser mapping system.

Example 20 is a system as in any of Examples 1-19, wherein the critical tissue structure is one or more of a nerve, a ureter, a blood vessel, an artery, a blood flow, cancerous tissue, or a tumor.

Example 21 is a system as in any of Examples 1-20, wherein the controller is configured to synchronize timing of the pulses of electromagnetic radiation during a blanking period of the image sensor, wherein the blanking period corresponds to a time between a readout of a last row of active pixels in the pixel array and a beginning of a next subsequent readout of active pixels in the pixel array.

Example 22 is a system as in any of Examples 1-21, wherein the controller is configured to adjust a sequence of the pulses of electromagnetic radiation emitted by the emitter based on a threshold, wherein the threshold determines proper illumination of a scene in a light deficient environment.

Example 23 is a system as in any of Examples 1-22, wherein two or more pulses of electromagnetic radiation emitted by the emitter result in two or more instances of reflected electromagnetic radiation that are sensed by the pixel array to generate two or more exposure frames that are combined to form an image frame.

Example 24 is a system as in any of Examples 1-23, wherein the image sensor is configured to generate a topology exposure frame by sensing reflected electromagnetic radiation resulting from the emitter pulsing the laser mapping pattern, wherein the topology exposure frame comprises information for determining real time measurements comprising one or more of: a distance from an endoscope to an object; an angle between an endoscope and the object; or surface topology information about the object.

Example 25 is a system as in any of Examples 1-24, wherein the topology exposure frame comprises information for determining the real time measurements to an accuracy of less than 10 centimeters.

Example 26 is a system as in any of Examples 1-25, wherein the topology exposure frame comprises information for determining the real time measurements to an accuracy of less than one millimeter.

Example 27 is a system as in any of Examples 1-26, further comprising a plurality of tools, wherein at least a portion of the pulses of electromagnetic radiation emitted by the emitter comprises a tool-specific laser mapping pattern for each of the plurality of tools.

Example 28 is a system as in any of Examples 1-27, wherein the laser mapping pattern emitted by the emitter comprises a first output and a second output that are independent from one another, wherein the first output is for light illumination and the second output is for tool tracking.

Example 29 is a system as in any of Examples 1-28, wherein the image sensor comprises a first image sensor and a second image sensor such that the image sensor can generate a three-dimensional image.

Example 30 is a system as in any of Examples 1-29, wherein the emitter is configured to emit a sequence of pulses of electromagnetic radiation repeatedly sufficient for generating a video stream comprising a plurality of image frames, wherein each image frame in the video stream comprises data from a plurality of exposure frames wherein each of the exposure frames corresponds to a pulse of electromagnetic radiation.

Example 31 is a means for performing functions of any of the Examples 1-30.

Example 32 is a method of performing any of the functions of the system of Examples 1-30.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
an emitter that emits a plurality of pulses of electromagnetic radiation according to a pulse cycle, wherein the emitter comprises a mapping source that pulses electromagnetic radiation in a mapping pattern;
an image sensor comprising a pixel array that detects electromagnetic radiation, wherein the pixel array comprises a plurality of pixels each configurable as a short exposure pixel or a long exposure pixel;
a controller comprising a processor in electrical communication with the image sensor and the emitter;
wherein the mapping source emits the mapping pattern with each pulse of a plurality of pulses by the mapping source.

2. The system of claim 1, wherein the pixel array comprises a plurality of short exposure pixels and a plurality of long exposure pixels arranged in a checkerboard pattern such that a short exposure pixel is located adjacent to a long exposure pixel.

3. The system of claim 1, wherein:
each of the plurality of pixels of the pixel array comprises a transfer gate transistor;
each transfer gate transistor is in electrical communication with a TX signal; and
the TX signal provides a global operation for the transfer gate transistors of the plurality of pixels of the pixel array.

4. The system of claim 3, wherein:
the TX signal comprises a TX1 signal and a TX2 signal;
at least two pixels of the plurality of pixels of the pixel array share a floating diffusion in a horizontal direction in a two-way pixel share;
the TX1 signal communicates with transfer gate transistors of pixels located on a first side of the two-way pixel share on odd rows and with transfer gate transistors of pixels located on a second side of the two-way pixel share on even rows; and
the TX2 signal communicates with transfer gate transistors of pixels located on the second side of the two-way pixel share on odd rows and with transfer gate transistors of pixels located on the first side of the two-way pixel share on even rows.

5. The system of claim 1, wherein the image sensor performs horizontal binning during a charge period of the pixel array.

6. The system of claim 1, wherein a pixel grouping of the pixel array shares a floating diffusion, wherein the pixel grouping comprises two pixels or four pixels.

7. The system of claim 1, wherein the pixel array is disposed on a first substrate of the image sensor and supporting circuitry for the pixel array is disposed remotely on a second substrate of the image sensor.

8. The system of claim 1, wherein the image sensor outputs a plurality of exposure frames according to a sensor cycle that is synchronized with the pulse cycle, and wherein each of the plurality of exposure frames corresponds to at least one pulse of the plurality of pulses emitted by the emitter.

9. The system of claim 8, wherein the pixel array accumulates the electromagnetic radiation during a blanking period and reads out the accumulated electromagnetic radiation during a readout period.

10. The system of claim 8, wherein at least a portion of the plurality of exposure frames are combined to form an image frame.

11. The system of claim 1, wherein the electromagnetic radiation in the mapping pattern is not visible to a user of the system.

12. The system of claim 1, wherein the emitter further comprises a visible source that pulses electromagnetic radiation within a visible waveband of the electromagnetic spectrum.

13. The system of claim 1, wherein the emitter is configured to emit, during a pulse duration, a plurality of sub-pulses of electromagnetic radiation having a sub-duration shorter than the pulse duration.

14. The system of claim 1, wherein one or more of the plurality of pulses of electromagnetic radiation emitted by the emitter comprise electromagnetic radiation emitted at two or more wavelengths simultaneously as a single pulse or a single sub-pulse.

15. The system of claim 1, wherein the image sensor detects the electromagnetic radiation and reads out a plurality of exposure frames according to a sensor cycle, and wherein the sensor cycle is synchronized with the pulse cycle.

16. The system of claim 1, wherein the emitter further comprises a fluorescence source that pulses an excitation wavelength for fluorescing a reagent, and wherein the image sensor detects a relaxation wavelength of the reagent and outputs a fluorescence exposure frame in response to the emitter actuating the fluorescence source.

17. The system of claim 16, wherein the controller is configured to provide the fluorescence exposure frame to a corresponding fluorescence system that determines a location of a tissue structure based on the fluorescence exposure frame.

18. The system of claim 17, wherein the controller is further configured to:
   receive the location of the tissue structure from the corresponding fluorescence system;
   generate an overlay frame comprising the location of the tissue structure; and
   combine the overlay frame with a color image frame depicting the scene to indicate the location of the tissue structure within the scene.

19. The system of claim 18, wherein the image sensor outputs a mapping exposure frame in response to the emitter actuating the mapping source, and wherein the mapping exposure frame comprises information for calculating a topographical map of the scene, and wherein the controller is further configured to:
   provide the mapping exposure frame to a corresponding mapping system that calculates one or more of the topographical map of the scene, a distance between two or more objects within the scene, or a dimension of an object within the scene based on the mapping exposure frame;
   provide the location of the tissue structure to the corresponding mapping system.

20. The system of claim 19, wherein the tissue structure is one or more of a nerve, a ureter, a blood vessel, an artery, a blood flow, cancerous tissue, or a tumor.

21. The system of claim 1, wherein the image sensor detects the electromagnetic radiation and reads out a plurality of exposure frames according to a sensor cycle, and wherein the controller synchronizes operations of the emitter and the image sensor by providing the pulse cycle to the emitter and providing the sensor cycle to the image sensor.

22. The system of claim 1, wherein the controller is configured to adjust a sequence of the pulses of electromagnetic radiation emitted by the emitter based on a threshold, wherein the threshold determines proper illumination of a scene in a light deficient environment.

23. The system of claim 1, wherein two or more pulses of electromagnetic radiation emitted by the emitter result in two or more instances of reflected electromagnetic radiation that are sensed by the pixel array to generate two or more exposure frames that are combined to form an image frame.

24. The system of claim 1, wherein the image sensor is configured to generate a mapping exposure frame in response to the emitter actuating the mapping source, and wherein the mapping exposure frame comprises information for determining real time measurements comprising one or more of:
   a distance from an endoscope to an object;
   an angle between an endoscope and the object; or
   surface topology information about the object.

25. The system of claim 24, wherein the mapping exposure frame comprises information for determining the real time measurements to an accuracy of less than 10 centimeters.

26. The system of claim 24, wherein the mapping exposure frame comprises information for determining the real time measurements to an accuracy of less than one millimeter.

27. The system of claim 1, further comprising a plurality of tools, wherein at least a portion of the pulses of electromagnetic radiation emitted by the emitter comprises a tool-specific laser mapping pattern for each of the plurality of tools.

28. The system of claim 1, wherein the electromagnetic radiation in the mapping pattern comprises a first output and a second output that are independent from one another, wherein the first output is for light illumination and the second output is for tool tracking.

29. The system of claim 1, wherein the image sensor comprises a first image sensor and a second image sensor such that the image sensor can output data for generating a three-dimensional image.

30. The system of claim 1, wherein the emitter pulses according to the pulse cycle at a rate sufficient for generating a video stream comprising color visualization data and mapping data.

* * * * *